US007744534B2

(12) United States Patent
Chalana et al.

(10) Patent No.: US 7,744,534 B2
(45) Date of Patent: *Jun. 29, 2010

(54) 3D ULTRASOUND-BASED INSTRUMENT FOR NON-INVASIVE MEASUREMENT OF AMNIOTIC FLUID VOLUME

(75) Inventors: Vikram Chalana, Mill Creek, WA (US); Gerald McMorrow, Kirkland, WA (US); Stephen James Dudycha, Bothell, WA (US)

(73) Assignee: Verathon Inc., Bothell, WA (US)

( * ) Notice: Subject to any disclaimer, the term of this patent is extended or adjusted under 35 U.S.C. 154(b) by 912 days.

This patent is subject to a terminal disclaimer.

(21) Appl. No.: 11/362,368

(22) Filed: Feb. 24, 2006

(65) Prior Publication Data
US 2006/0235301 A1 Oct. 19, 2006

Related U.S. Application Data

(63) Continuation of application No. PCT/US2005/43836, filed on Dec. 6, 2005, and a continuation-in-part of application No. 11/295,043, filed on Dec. 6, 2005, application No. 11/362,368, and a continuation of application No. PCT/US2005/31755, filed on Sep. 9, (Continued)

(60) Provisional application No. 60/760,677, filed on Jan. 20, 2006, provisional application No. 60/633,485, filed on Dec. 6, 2004, provisional application No. 60/566,823, filed on Apr. 30, 2004, provisional application No. 60/423,881, filed on Nov. 5, 2002, provisional application No. 60/400,624, filed on Aug. 2, 2002, provisional application No. 60/608,426, filed on Sep. 9, 2004, provisional application No. 60/605,391, filed on Aug. 27, 2004, provisional application No. 60/609,184, filed on Sep. 10, 2004, provisional application No. 60/470,525, filed on May 12, 2003.

(51) Int. Cl.
*A61B 8/08* (2006.01)
(52) U.S. Cl. .............. 600/437; 600/407; 600/438; 600/439; 600/443; 600/447; 382/128; 382/130; 382/131
(58) Field of Classification Search ................. 600/407, 600/437, 438, 439, 443, 447, 449
See application file for complete search history.

(56) References Cited

U.S. PATENT DOCUMENTS 4,431,007 A    2/1984  Amazeen et al.

(Continued)

FOREIGN PATENT DOCUMENTS

| JP | 2000-126178 | 9/2000 |
| JP | 2000-126181 | 9/2000 |
| JP | 2000-126182 | 9/2000 |

OTHER PUBLICATIONS

Grover et al., "Three-Dimensional Amniotic Fluid Volume," *Obstetrics & Gynecology* (Dec. 1997) 1007-1010, 90:6; Elsevier Science, Inc., University of California Los Angeles.

(Continued)

*Primary Examiner*—Brian Casler
*Assistant Examiner*—Baisakhi Roy
(74) *Attorney, Agent, or Firm*—Black Lowe & Graham

(57) ABSTRACT

A hand-held 3D ultrasound instrument is disclosed which is used to non-invasively and automatically measure amniotic fluid volume in the uterus requiring a minimum of operator intervention. Using a 2D image-processing algorithm, the instrument gives automatic feedback to the user about where to acquire the 3D image set. The user acquires one or more 3D data sets covering all of the amniotic fluid in the uterus and this data is then processed using an optimized 3D algorithm to output the total amniotic fluid volume corrected for any fetal head brain volume contributions.

20 Claims, 31 Drawing Sheets

Related U.S. Application Data 2005, which is a continuation of application No. PCT/US2005/30799, filed on Aug. 29, 2005, and a continuation-in-part of application No. 11/119,355, filed on Apr. 29, 2005, now Pat. No. 7,520,857, and a continuation-in-part of application No. 10/701,955, filed on Nov. 5, 2003, now Pat. No. 7,087,022, which is a continuation-in-part of application No. 10/443,126, filed on May 20, 2003, now Pat. No. 7,041,059, application No. 11/362,368, which is a continuation of application No. PCT/US03/24368, filed on Aug. 1, 2003, application No. 11/362,368, which is a continuation of application No. PCT/US03/14785, filed on May 9, 2003, which is a continuation of application No. 10/165,556, filed on Jun. 7, 2002, now Pat. No. 6,676,605, application No. 11/362,368, which is a continuation of application No. 10/633,186, filed on Jul. 31, 2003, now Pat. No. 7,004,904, and a continuation of application No. 10/443,126, filed on May 20, 2003, now Pat. No. 7,041,059.

(56) References Cited

U.S. PATENT DOCUMENTS

| | | | |
|---|---|---|---|
| 5,060,515 | A | 10/1991 | Kanda et al. |
| 5,235,985 | A | 8/1993 | McMorrow et al. |
| 5,575,286 | A | 11/1996 | Weng et al. |
| 6,309,353 | B1 | 10/2001 | Cheng et al. |
| 6,400,848 | B1* | 6/2002 | Gallagher ............... 382/254 |
| 6,575,907 | B1* | 6/2003 | Soferman et al. ........... 600/438 |
| 6,688,177 | B2 | 2/2004 | Wiesauer |
| 6,695,780 | B1 | 2/2004 | Nahum et al. |
| 6,939,301 | B2* | 9/2005 | Abdelhak ................ 600/437 |
| 7,041,059 | B2* | 5/2006 | Chalana et al. ............ 600/437 |
| 7,087,022 | B2* | 8/2006 | Chalana et al. ............ 600/449 |
| 2002/0133075 | A1 | 9/2002 | Abdelhak |
| 2003/0174872 | A1 | 9/2003 | Chalana et al. |
| 2006/0235301 | A1* | 10/2006 | Chalana et al. ............ 600/443 |
| 2008/0146932 | A1* | 6/2008 | Chalana et al. ............ 600/447 |

OTHER PUBLICATIONS

Mann et al., "Novel Technique for Assessing Amniotic Fluid Volume: Use of a Three-Dimensional Bladder Scanner," *J. of Maternal Fetal Med.* (2000) 9:308-310, Torrance, California.

Ross, "Amniotic Fluid vol. Determination," *Letter to the Editor*, 169 (2:1), *Am. J. Obstet. Gynecol.*, Aug. 1993.

Cheng et al., "Boundary Extraction Method for Three Dimensional Ultrasonic Echo Imaging Using Fuzzy Reasoning and Relaxation Techniques," (1994) 1610-1614 IEEE, Tokyo, Japan.

Rutherford et al., "The Four-Quadrant Assessment of Amniotic Fluid Volume: An Adjunct to Antepartum Fetal Heart Rate Testing," (1987) 353-356 70:3 (Part 1) *Obstetrics & Gynecology*.

Chamberlain et al., "Ultrasound Evaluation of Amniotic Fluid vol. II. The Relationship of Increased Amniotic Fluid Vol. to Perinatal Outcome," (Oct. 1, 1984) 250-254 *Am. J. Ob. Gyn.*, Canada.

Phelan et al., "Amniotic Fluid Volume Assessment with the Four-Quadrant Technique at 36-42 Weeks' Gestation," (Jul. 1987) 540-42, 32:7 Dept. Ob. Gyn., UCLA, California.

Chamberlain, Paul, "Amniotic Fluid Volume: Ultrasound Assessment and Clinical Significance," (Oct. 1985) 163-167, Seminars in Perinatology 9:4, Grune & Stratton, Inc., Galway, Ireland.

Crowley et al., "The Value of Ultrasound Measurement of Amniotic Fluid Volume In The Management of Prolonged Pregnancies," (May 1984) 444-448 vol. 91, British Journal of Obstetrics and Gynaecology.

Stangenberg et al., "Amniotic Fluid Volumes In Pregnant Diabetics During the Last Trimester: A Comparative Study Using Ultrasound and PAH Dilution," *Acta Obstet Gynecol Scand* (1982) 61:313-316, Stockholm, Sweden.

Manning et al, "Qualitative Amniotic Fluid Volume Determination By Ultrasound: Antepartum Detection of Intrauterine Growth Retardation," Thirty-Sixth Annual Meeting of The Society of Obstetricians and Gynaecologists of Canada, Jasper, Alberta, Canada, Jun. 10-14, 1980. (Feb. 1, 1981), 254-258, *Am. J. Obstet. Gynecol.*, C.V. Mosby Co., Canada.

Weissman et al, "Sonographic Measurement of Amniotic Fluid Volume In the First Trimester of Pregnancy," (Jun. 23, 1996) American Institute of Ultrasound in Medicine, *J Ultrasound Med.*, 15:771-774.

Sagiv et al, "Application of a Semiautomatic Boundary Detection Algorithm for the Assessment of Amniotic Fluid Quantity from Ultrasound Images," (1999) *Ultrasound in Med. & Biol.*, 25:4 515-526 *World Federation for Ultrasound in Medicine*, Elsevier Science, Inc., Tel Aviv University, Israel.

Magann et al., "Measurement of Amniotic Fluid Volume: Accuracy of Ultrasonography Techniques," (Dec. 1992) 1533-1537, *Am. J. Obstet. Gynecol.*, Jackson, Mississippi, and Augusta, Georgia.

Myles et al., "Four-Quadrant Assessment of Amniotic Fluid Volume: Distribution's Role in Predicting Fetal Outcome," (1992) 769-774, 80:5, *Ob. & Gyn.*, The American College of Obstetricians and Gynecologists.

Moore, MD, Thomas R., "Superiority of the Four-Quadrant Sum Over the Single-Deepest-Pocket Technique in Ultrasonographic Identification of Abnormal Amniotic Fluid Vols.," 762-767, 163:3, U. of California, San Diego.

Jeng et al., "Amniotic Fluid Index Measurement with the Four-Quadrant Technique During Pregnancy," (1990) 35:7, 674-677, *J. Reproductive Medicine*, The Journal of Reproductive Medicine, Inc.

Schiff et al., "Standardized Measurement of Amniotic Fluid Volume By Correlation of Sonography With Dye Dilution Technique," (1990) 44-46, 76:1 Department of Obstetrics and Gynecology; Tel Aviv, Israel.

Gramellini et al., "Sonographic Assessment of Amniotic Fluid Volume Between 11 and 24 Weeks of Gestation: Construction of Reference Intervals Related to Gestational Age," (2001) *Ultrasound Obstet. Gynecol.*, 17:410-415, Parma, Italy.

Magann et al., "Ultrasound Estimation of Amniotic Fluid Volume Using the Largest Vertical Pocket Containing Umbilical Cord: Measure To or Through Cord?," (2002) *Ultrasound Obstet. Gynecol.*, 20:464-467; Australia, Mississippi and South Carolina.

Magann et al., "Ultrasound Estimate of Amniotic Fluid Volume: Color Doppler Overdiagnosis of Oligohydraminos," (2001) 98:1, 71-74, *Obstetrics & Gynecology*, Elsevier Science, Inc., South Carolina and Mississippi.

Schrimmer et al., "Sonographic Evaluation of Amniotic Fluid Volume," (2002) 45:4, 1026-1038, *Clinical Obstetrics and Gynecology*, Lippincott Williams & Wilkins, Inc., University of California, San Diego.

Sahin et al., "Estimation of the Amniotic Fluid Volume Using the Cavalieri Method on Ultrasound Images," (2003) 82:25-30, *Int'l. J. of Gynecol. And Obstet.*, Elsevier Science, Inc., Samsun, Turkey.

* cited by examiner

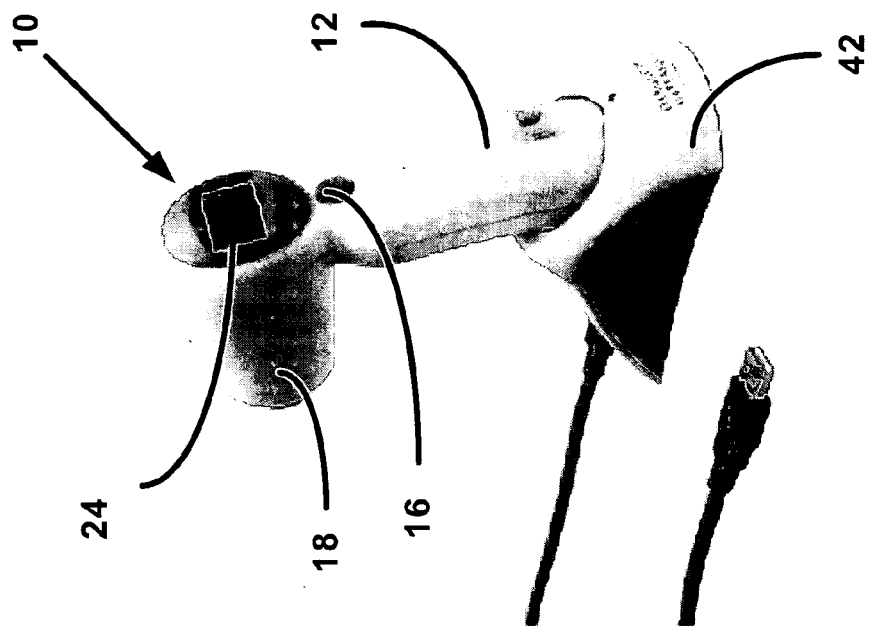
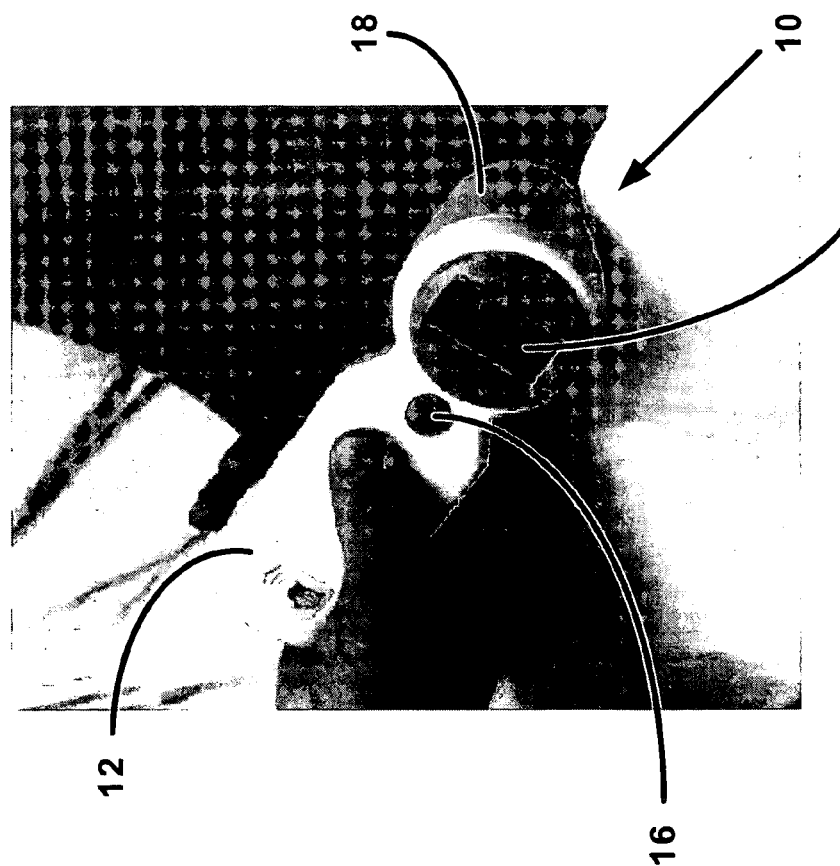
FIG. 2B
FIG. 2A

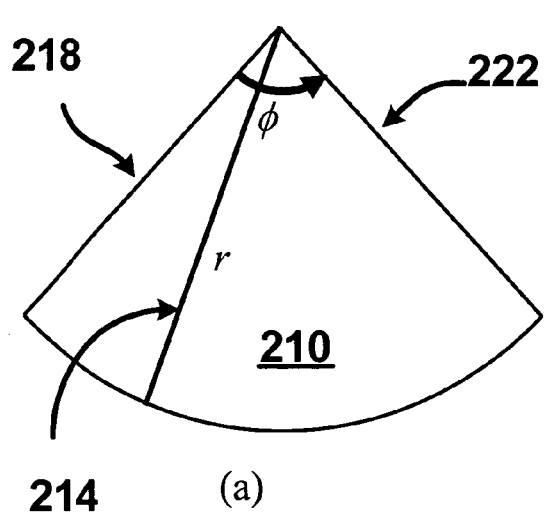 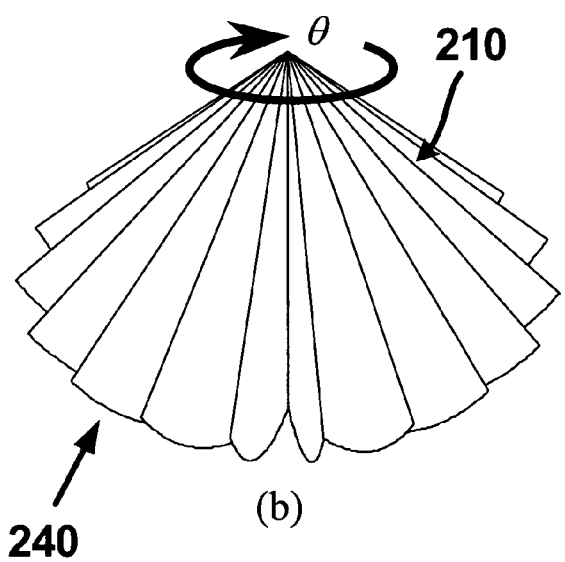
FIG. 5A     FIG. 5B

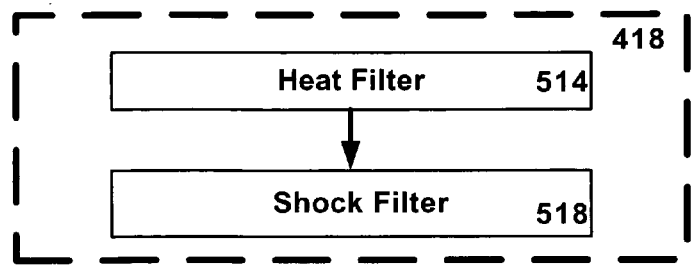
FIG. 8A
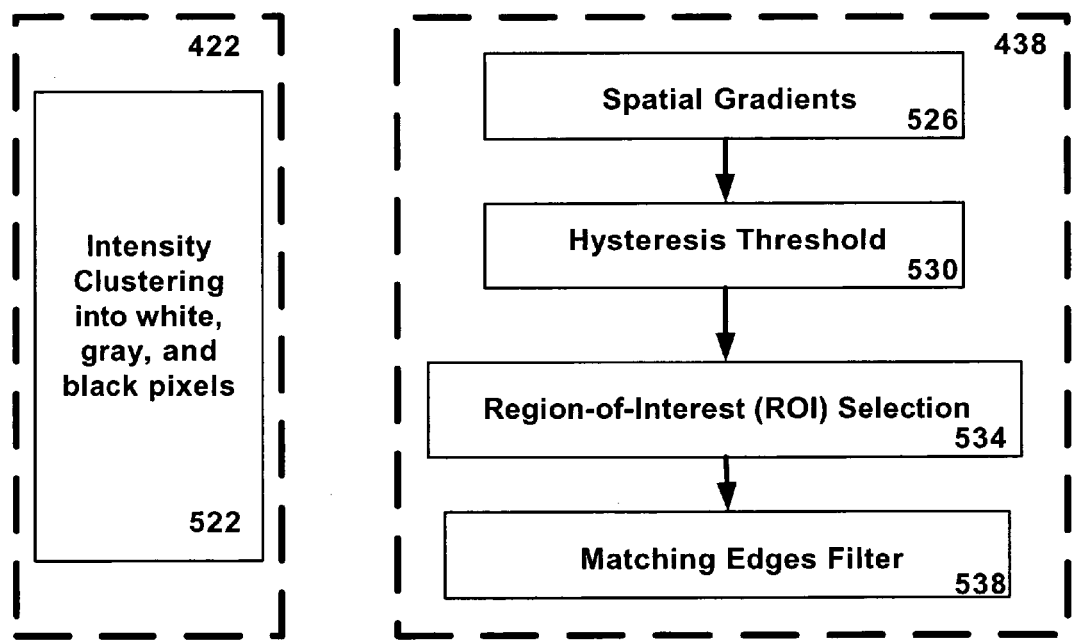
FIG. 8B     FIG. 8C

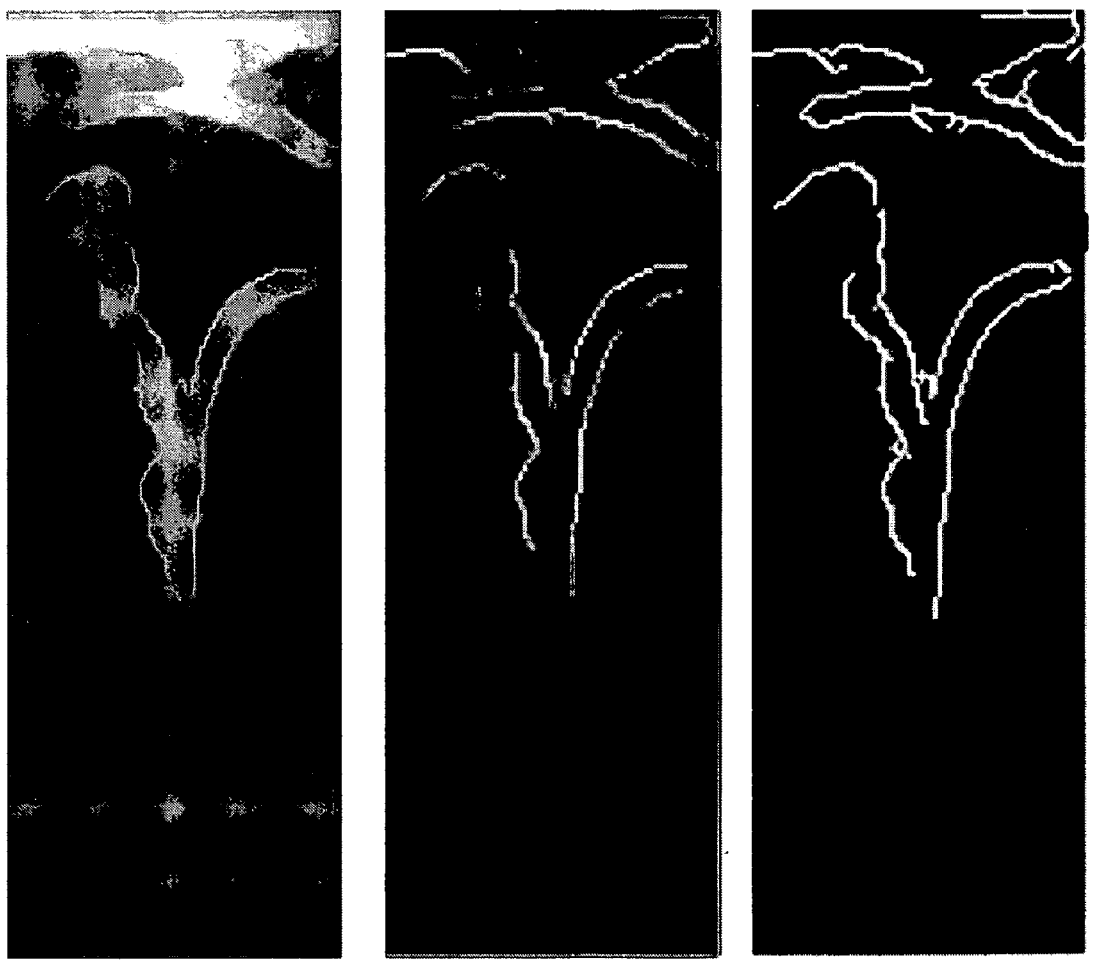

US 7,744,534 B2

3D ULTRASOUND-BASED INSTRUMENT FOR NON-INVASIVE MEASUREMENT OF AMNIOTIC FLUID VOLUME

PRIORITY CLAIM

This U.S. patent application Ser. No. 11/362,368 filed Feb. 24, 2006 claims priority to U.S. provisional patent application Ser. No. 60/760,677 filed Jan. 20, 2006.

This U.S. patent application Ser. No. 11/362,368 filed Feb. 24, 2006 is a continuation of PCT application serial number PCT/US05/043836 filed Dec. 6, 2005 and to U.S. patent application Ser. No. 11/295,043 filed Dec. 6, 2005 that claims priority to U.S. provisional patent application Ser. No. 60/633,485 filed Dec. 6, 2004.

This U.S. patent application Ser. No. 11/362,368 filed Feb. 24, 2006 is a continuation of PCT application serial number PCT/US05/30799 filed Aug. 29, 2005 which claims priority to U.S. patent application Ser. No. 11/213,284 filed Aug. 26, 2005 that claims priority to U.S. provisional patent application Ser. No. 60/608,426 filed Sep. 9, 2004 and 60/605,391 filed Aug. 27, 2004.

This U.S. patent application Ser. No. 11/362,368 filed Feb. 24, 2006 is a continuation of PCT application serial number PCT/US05/31755 filed Sep. 9, 2005 which claims priority to U.S. patent application Ser. No. 11/222,360 filed Sep. 8, 2005 that claims priority to U.S. provisional patent application Ser. No. 60/609,184 filed Sep. 10, 2004.

This U.S. patent application Ser. No. 11/362,368 filed Feb. 24, 2006 is a continuation of U.S. patent application Ser. No. 11/119,355 filed Apr. 29, 2005 now U.S. Pat. No. 7,520,857 that claims priority to U.S. provisional patent application Ser. No. 60/566,823 filed Apr. 30, 2004. This U.S. patent application Ser. No. 11/362,368 filed Feb. 24, 2006 is a continuation-in-part of U.S. patent application Ser. No. 10/701,955 filed Nov. 5, 2003, now U.S. Pat. No. 7,087,022 which in turn claims priority to and is a continuation-in-part of U.S. patent application Ser. No. 10/443,126 filed May 20, 2003.

This U.S. patent application Ser. No. 11/362,368 filed Feb. 24, 2006 is a continuation of and claims priority to PCT application serial number PCT/US03/24368 filed Aug. 1, 2003, which claims priority to U.S. provisional patent application Ser. No. 60/423,881 filed Nov. 5, 2002 and U.S. provisional patent application Ser. No. 60/400,624 filed Aug. 2, 2002.

This U.S. patent application Ser. No. 11/362,368 filed Feb. 24, 2006 is also a continuation of and claims priority to PCT Application Serial No. PCT/US03/14785 filed May 9, 2003, which is a continuation of U.S. patent application Ser. No. 10/165,556 filed Jun. 7, 2002 now U.S. Pat. No. 6,676,605.

This U.S. patent application Ser. No. 11/362,368 filed Feb. 24, 2006 is also a continuation of and claims priority to U.S. patent application Ser. No. 10/633,186 filed Jul. 31, 2003 now U.S. Pat. No. 7,004,904 which claims priority to U.S. provisional patent application Ser. No. 60/470,525 filed May 12, 2003 and U.S. provisional patent application Ser. No. 60/423,881 filed Nov. 5, 2002, and to U.S. patent application Ser. No. 10/443,126 filed May 20, 2003 now U.S. Pat. No. 7,041,059 which claims priority to U.S. provisional patent application Ser. No. 60/423,881 filed Nov. 5, 2002 and to U.S. provisional application 60/400,624 filed Aug. 2, 2002. All of the above applications are incorporated by reference in their entirety as if fully set forth herein.

FIELD OF THE INVENTION

This invention pertains to the field of obstetrics, particularly to ultrasound-based non-invasive obstetric measurements.

BACKGROUND OF THE INVENTION

Measurement of the amount of Amniotic Fluid (AF) volume is critical for assessing the kidney and lung function of a fetus and also for assessing the placental function of the mother. Amniotic fluid volume is also a key measure to diagnose conditions such as polyhydramnios (too much AF) and oligohydramnios (too little AF). Polyhydramnios and oligohydramnios are diagnosed in about 7-8% of all pregnancies and these conditions are of concern because they may lead to birth defects or to delivery complications. The amniotic fluid volume is also one of the important components of the fetal biophysical profile, a major indicator of fetal well-being.

The currently practiced and accepted method of quantitatively estimating the AF volume is from two-dimensional (2D) ultrasound images. The most commonly used measure is known as the use of the amniotic fluid index (AFI). AFI is the sum of vertical lengths of the largest AF pockets in each of the 4 quadrants. The four quadrants are defined by the umbilicus (the navel) and the linea nigra (the vertical mid-line of the abdomen). The transducer head is placed on the maternal abdomen along the longitudinal axis with the patient in the supine position. This measure was first proposed by Phelan et al (Phelan J P, Smith C V, Broussard P, Small M., "Amniotic fluid volume assessment with the four-quadrant technique at 36-42 weeks' gestation," J Reprod Med July; 32(7): 540-2, 1987) and then recorded for a large normal population over time by Moore and Cayle (Moore T R, Cayle J E. "The amniotic fluid index in normal human pregnancy," Am J Obstet Gynecol May; 162(5): 1168-73, 1990).

Even though the AFI measure is routinely used, studies have shown a very poor correlation of the AFI with the true AF volume (Sepulveda W, Flack N J, Fisk N M., "Direct volume measurement at midtrimester amnioinfusion in relation to ultrasonographic indexes of amniotic fluid volume," Am J Obstet Gynecol April; 170(4): 1160-3, 1994). The correlation coefficient was found to be as low as 0.55, even for experienced sonographers. The use of vertical diameter only and the use of only one pocket in each quadrant are two reasons why the AFI is not a very good measure of AF Volume (AFV).

Some of the other methods that have been used to estimate AF volume include:

Dye dilution technique. This is an invasive method where a dye is injected into the AF during amniocentesis and the final concentration of dye is measured from a sample of AF removed after several minutes. This technique is the accepted gold standard for AF volume measurement; however, it is an invasive and cumbersome method and is not routinely used.

Subjective interpretation from ultrasound images. This technique is obviously dependent on observer experience and has not been found to be very good or consistent at diagnosing oligo- or poly-hydramnios.

Vertical length of the largest single cord-free pocket. This is an earlier variation of the AFI where the diameter of only one pocket is measured to estimate the AF volume.

Two-diameter areas of the largest AF pockets in the four quadrants. This is similar to the AFI; however, in this case, two diameters are measured instead of only one for the largest pocket. This two diameter area has been recently shown to be better than AFI or the single pocket measurement in identifying oligohydramnios (Magann E F, Perry K G Jr, Chauhan S P, Anfanger P J, Whitworth N S, Morrison J C., "The accuracy of ultrasound evaluation of amniotic fluid volume in singleton pregnancies: the effect of operator experience and ultrasound interpretative technique," J Clin Ultrasound, June; 25(5):249-53, 1997).

The measurement of various anatomical structures using computational constructs are described, for example, in U.S. Pat. No. 6,346,124 to Geiser, et al. (Autonomous Boundary Detection System For Echocardiographic Images). Similarly, the measurement of bladder structures are covered in U.S. Pat. No. 6,213,949 to Ganguly, et al. (System For Estimating Bladder Volume) and U.S. Pat. No. 5,235,985 to McMorrow, et al., (Automatic Bladder Scanning Apparatus). The measurement of fetal head structures is described in U.S. Pat. No. 5,605,155 to Chalana, et al., (Ultrasound System For Automatically Measuring Fetal Head Size). The measurement of fetal weight is described in U.S. Pat. No. 6,375,616 to Soferman, et al. (Automatic Fetal Weight Determination).

Pertaining to ultrasound-based determination of amniotic fluid volumes, Segiv et al. (in Segiv C, Akselrod S, Tepper R., "Application of a semiautomatic boundary detection algorithm for the assessment of amniotic fluid quantity from ultrasound images." Ultrasound Med Biol, May; 25(4): 515-26, 1999) describe a method for amniotic fluid segmentation from 2D images. However, the Segiv et al. method is interactive in nature and the identification of amniotic fluid volume is very observer dependent. Moreover, the system described is not a dedicated device for amniotic fluid volume assessment.

Grover et al. (Grover J, Mentakis E A, Ross M G, "Three-dimensional method for determination of amniotic fluid volume in intrauterine pockets." Obstet Gynecol, December; 90(6): 1007-10, 1997) describe the use of a urinary bladder volume instrument for amniotic fluid volume measurement. The Grover et al. method makes use of the bladder volume instrument without any modifications and uses shape and other anatomical assumptions specific to the bladder that do not generalize to amniotic fluid pockets. Amniotic fluid pockets having shapes not consistent with the Grover et al. bladder model introduces analytical errors. Moreover, the bladder volume instrument does not allow for the possibility of more than one amniotic fluid pocket in one image scan. Therefore, the amniotic fluid volume measurements made by the Grover et al. system may not be correct or accurate.

None of the currently used methods for AF volume estimation are ideal. Therefore, there is a need for better, non-invasive, and easier ways to accurately measure amniotic fluid volume.

SUMMARY OF THE INVENTION

The preferred form of the invention is a three dimensional (3D) ultrasound-based system and method using a hand-held 3D ultrasound device to acquire at least one 3D data set of a uterus and having a plurality of automated processes optimized to robustly locate and measure the volume of amniotic fluid in the uterus without resorting to pre-conceived models of the shapes of amniotic fluid pockets in ultrasound images. The automated process uses a plurality of algorithms in a sequence that includes steps for image enhancement, segmentation, and polishing.

A hand-held 3D ultrasound device is used to image the uterus trans-abdominally. The user moves the device around on the maternal abdomen and, using 2D image processing to locate the amniotic fluid areas, the device gives feedback to the user about where to acquire the 3D image data sets. The user acquires one or more 3D image data sets covering all of the amniotic fluid in the uterus and the data sets are then stored in the device or transferred to a host computer.

The 3D ultrasound device is configured to acquire the 3D image data sets in two formats. The first format is a collection of two-dimensional scanplanes, each scanplane being separated from the other and representing a portion of the uterus being scanned. Each scanplane is formed from one-dimensional ultrasound A-lines confined within the limits of the 2D scanplane. The 3D data sets is then represented as a 3D array of 2D scanplanes. The 3D array of 2D scanplanes is an assembly of scanplanes, and may be assembled into a translational array, a wedge array, or a rotatational array.

Alternatively, the 3D ultrasound device is configured to acquire the 3D image data sets from one-dimensional ultrasound A-lines distributed in 3D space of the uterus to form a 3D scancone of 3D-distributed scanline. The 3D scancone is not an assembly of 2D scanplanes.

The 3D image datasets, either as discrete scanplanes or 3D distributed scanlines, are then subjected to image enhancement and analysis processes. The processes are either implemented on the device itself or is implemented on the host computer. Alternatively, the processes can also be implemented on a server or other computer to which the 3D ultrasound data sets are transferred.

In a preferred image enhancement process, each 2D image in the 3D dataset is first enhanced using non-linear filters by an image pre-filtering step. The image pre-filtering step includes an image-smoothing step to reduce image noise followed by an image-sharpening step to obtain maximum contrast between organ wall boundaries.

A second process includes subjecting the resulting image of the first process to a location method to identify initial edge points between amniotic fluid and other fetal or maternal structures. The location method automatically determines the leading and trailing regions of wall locations along an A-mode one-dimensional scan line.

A third process includes subjecting the image of the first process to an intensity-based segmentation process where dark pixels (representing fluid) are automatically separated from bright pixels (representing tissue and other structures).

In a fourth process, the images resulting from the second and third step are combined to result in a single image representing likely amniotic fluid regions.

In a fifth process, the combined image is cleaned to make the output image smooth and to remove extraneous structures such as the fetal head and the fetal bladder.

In a sixth process, boundary line contours are placed on each 2D image. Thereafter, the method then calculates the total 3D volume of amniotic fluid in the uterus.

In cases in which uteruses are too large to fit in a single 3D array of 2D scanplanes or a single 3D scancone of 3D distributed scanlines, especially as occurs during the second and third trimester of pregnancy, preferred alternate embodiments of the invention allow for acquiring at least two 3D data sets, preferably four, each 3D data set having at least a partial ultrasonic view of the uterus, each partial view obtained from a different anatomical site of the patient.

In one embodiment a 3D array of 2D scanplanes is assembled such that the 3D array presents a composite image of the uterus that displays the amniotic fluid regions to provide the basis for calculation of amniotic fluid volumes. In a preferred alternate embodiment, the user acquires the 3D data sets in quarter sections of the uterus when the patient is in a supine position. In this 4-quadrant supine procedure, four image cones of data are acquired near the midpoint of each uterine quadrant at substantially equally spaced intervals between quadrant centers. Image processing as outlined above is conducted for each quadrant image, segmenting on the darker pixels or voxels associated with amniotic fluid. Correcting algorithms are applied to compensate for any quadrant-to-quadrant image cone overlap by registering and fixing one quadrant's image to another. The result is a fixed 3D mosaic image of the uterus and the amniotic fluid volumes or regions in the uterus from the four separate image cones.

Similarly, in another preferred alternate embodiment, the user acquires one or more 3D image data sets of quarter sections of the uterus when the patient is in a lateral position. In this multi-image cone lateral procedure, each image cones of data are acquired along a lateral line of substantially equally spaced intervals. Each image cone are subjected to the image processing as outlined above, with emphasis given to segmenting on the darker pixels or voxels associated with amniotic fluid. Scanplanes showing common pixel or voxel overlaps are registered into a common coordinate system along the lateral line. Correcting algorithms are applied to compensate for any image cone overlap along the lateral line. The result is a fixed 3D mosaic image of the uterus and the amniotic fluid volumes or regions in the uterus from the four separate image cones.

In yet other preferred embodiments, at least two 3D scan-cone of 3D distributed scanlines are acquired at different anatomical sites, image processed, registered and fused into a 3D mosaic image composite. Amniotic fluid volumes are then calculated.

The system and method further provides an automatic method to detect and correct for any contribution the fetal head provides to the amniotic fluid volume.

BRIEF DESCRIPTION OF THE DRAWINGS

FIG. 2A is a is depiction of the hand-held transceiver in use for scanning a patient;

FIG. 2B is a perspective view of the hand-held transceiver device sitting in a communication cradle;

FIG. 5A a graphical representation of a plurality of scan lines forming a single scan plane;

FIG. 5B is a graphical representation of a plurality of scanplanes forming a three-dimensional array having a substantially conic shape;

FIG. 8A depicts the sub-algorithms of Image Enhancement;

FIG. 8B depicts the sub-algorithms of Intensity-Based Segmentation;

FIG. 8C depicts the sub-algorithms of Edge-Based Segmentation;

FIG. 26 is a pixel difference kernel for obtaining X and Y derivatives to determine pixel gradient magnitudes for edge-based segmentation; and FIG. 27 is a 3-panel image set showing the progressive demarcation or edge detection of organ wall interfaces arising from edge-based segmentation algorithms.

DETAILED DESCRIPTION OF THE PREFERRED EMBODIMENT

Figure 1:
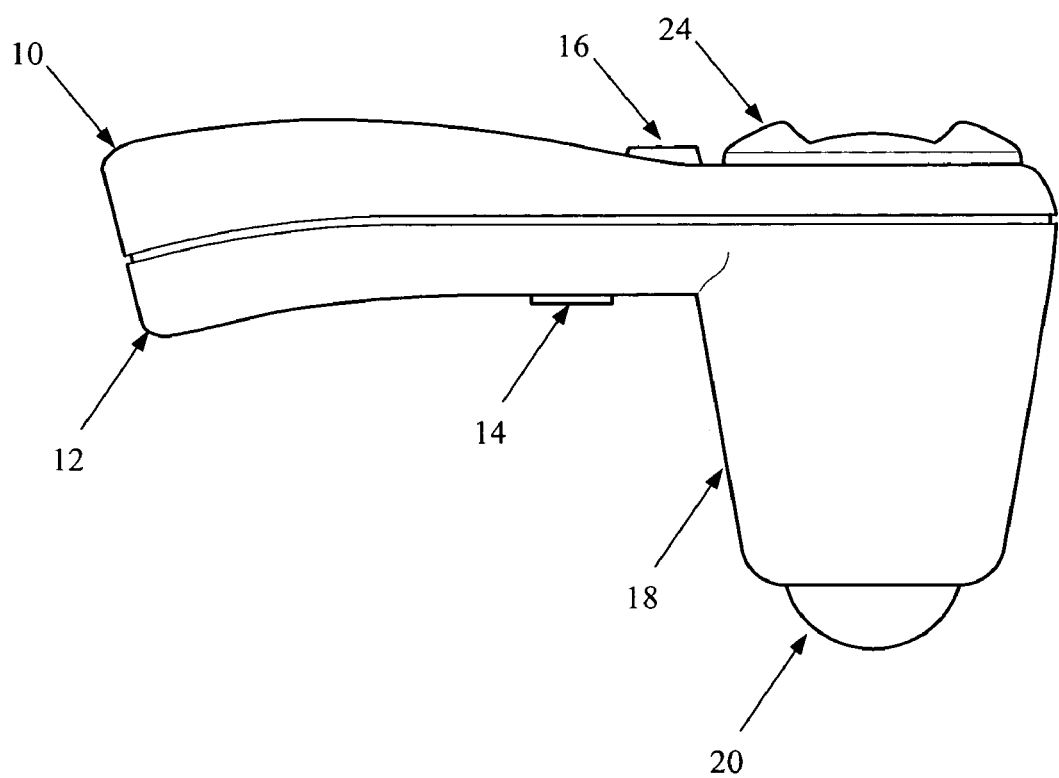
FIG. 1 is a side view of a microprocessor-controlled, hand-held ultrasound transceiver.

The preferred portable embodiment of the ultrasound transceiver of the amniotic fluid volume measuring system are shown in FIGS. 1-4. The transceiver 10 includes a handle 12 having a trigger 14 and a top button 16, a transceiver housing 18 attached to the handle 12, and a transceiver dome 20. A display 24 for user interaction is attached to the transceiver housing 18 at an end opposite the transceiver dome 20. Housed within the transceiver 10 is a single element transducer (not shown) that converts ultrasound waves to electrical signals. The transceiver 10 is held in position against the body of a patient by a user for image acquisition and signal processing. In operation, the transceiver 10 transmits a radio frequency ultrasound signal at substantially 3.7 MHz to the body and then receives a returning echo signal. To accommodate different patients having a variable range of obesity, the transceiver 10 can be adjusted to transmit a range of probing ultrasound energy from approximately 2 MHz to approximately 10 MHz radio frequencies.

The top button 16 selects for different acquisition volumes. The transceiver is controlled by a microprocessor and software associated with the microprocessor and a digital signal processor of a computer system. As used in this invention, the term "computer system" broadly comprises any microprocessor-based or other computer system capable of executing operating instructions and manipulating data, and is not limited to a traditional desktop or notebook computer. The display 24 presents alphanumeric or graphic data indicating the proper or optimal positioning of the transceiver 10 for initiating a series of scans. The transceiver 10 is configured to initiate the series of scans to obtain and present 3D images as either a 3D array of 2D scanplanes or as a single 3D scancone of 3D distributed scanlines. A suitable transceiver is the DCD372 made by Diagnostic Ultrasound. In alternate embodiments, the two- or three-dimensional image of a scan plane may be presented in the display 24.

Although the preferred ultrasound transceiver is described above, other transceivers may also be used. For example, the transceiver need not be battery-operated or otherwise portable, need not have a top-mounted display 24, and may include many other features or differences. The display 24 may be a liquid crystal display (LCD), a light emitting diode (LED), a cathode ray tube (CRT), or any suitable display capable of presenting alphanumeric data or graphic images.

FIG. 2A is a photograph of the hand-held transceiver 10 for scanning a patient. The transceiver 10 is then positioned over the patient's abdomen by a user holding the handle 12 to place the transceiver housing 18 against the patient's abdomen. The top button 16 is centrally located on the handle 12. Once optimally positioned over the abdomen for scanning, the transceiver 10 transmits an ultrasound signal at substantially 3.7 MHz into the uterus. The transceiver 10 receives a return ultrasound echo signal emanating from the uterus and presents it on the display 24.

FIG. 2B is a perspective view of the hand-held transceiver device sitting in a communication cradle. The transceiver 10 sits in a communication cradle 42 via the handle 12. This cradle can be connected to a standard USB port of any personal computer, enabling all the data on the device to be transferred to the computer and enabling new programs to be transferred into the device from the computer.

Figure 2C:
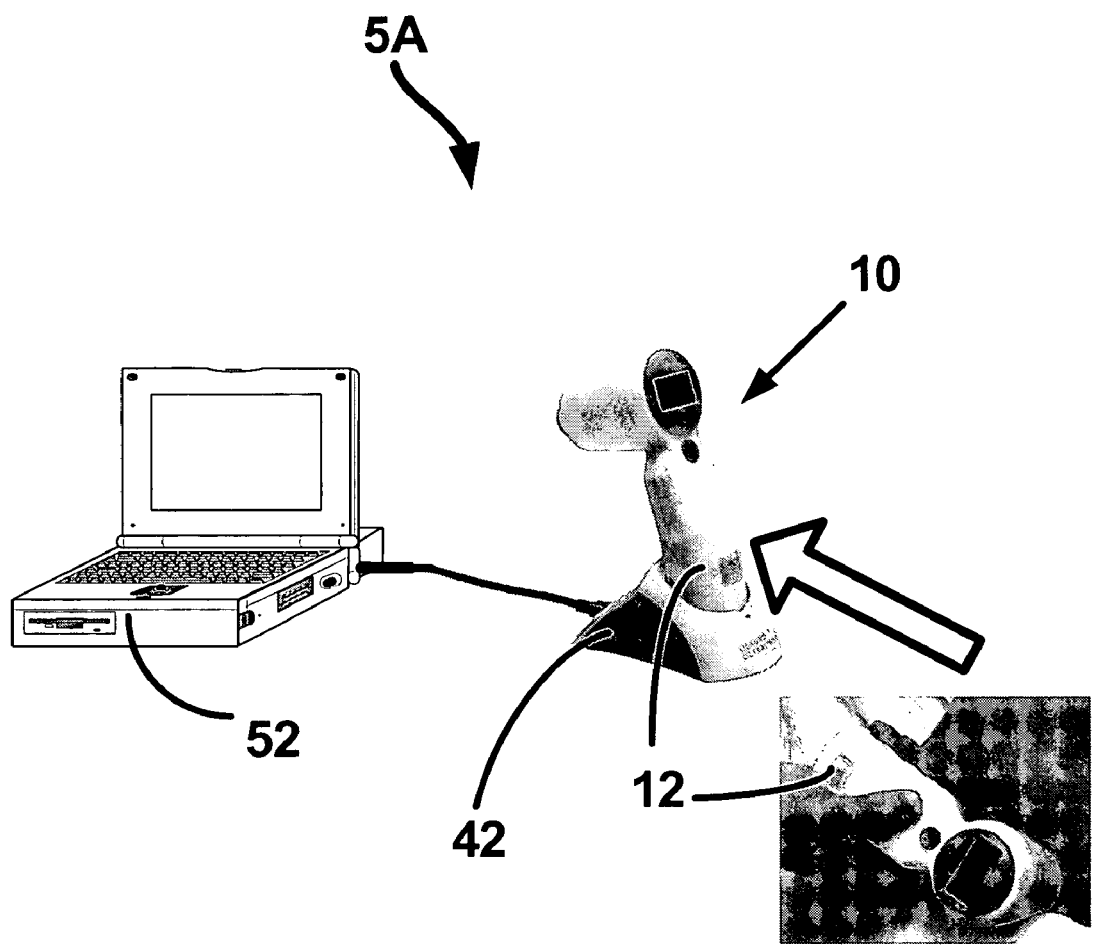
FIG. 2C is a perspective view of an amniotic fluid volume measuring system.

FIG. 2C is a perspective view of an amniotic fluid volume measuring system 5A. The system 5A includes the transceiver 10 cradled in the cradle 42 that is in signal communication with a computer 52. The transceiver 10 sits in a communication cradle 42 via the handle 12. This cradle can be connected to a standard USB port of any personal computer 52, enabling all the data on the transceiver 10 to be transferred to the computer for analysis and determination of amniotic fluid volume.

Figure 3:
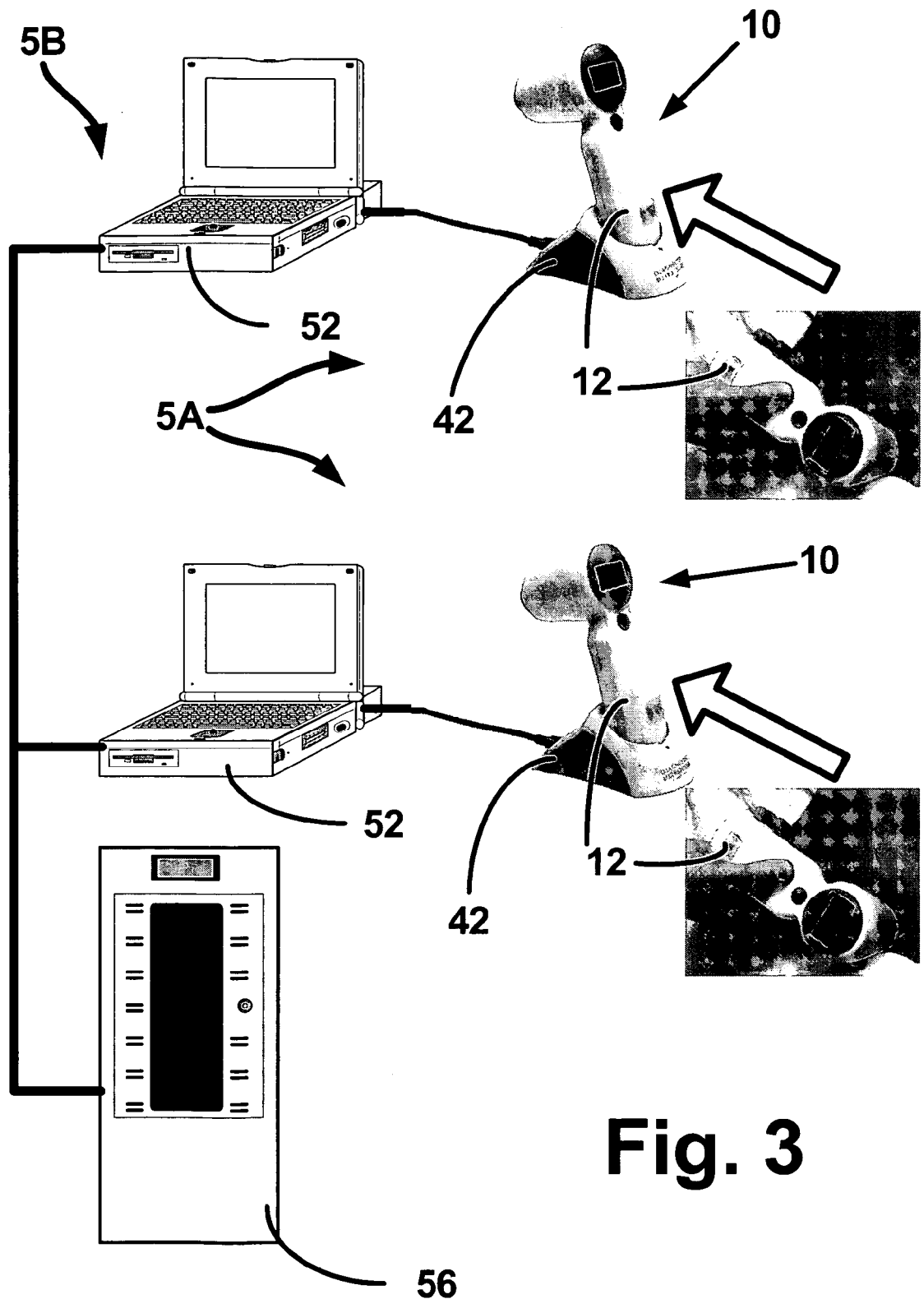
FIG. 3 is an alternate embodiment of an amniotic fluid volume measuring system in schematic view of a plurality of transceivers in connection with a server.

FIG. 3 depicts an alternate embodiment of an amniotic fluid volume measuring system 5B in a schematic view. The system 5B includes a plurality systems 5A in signal communication with a server 56. As illustrated each transceiver 10 is in signal connection with the server 56 through connections via a plurality of computers 52. FIG. 3, by example, depicts each transceiver 10 being used to send probing ultrasound radiation to a uterus of a patient and to subsequently retrieve ultrasound echoes returning from the uterus, convert the ultrasound echoes into digital echo signals, store the digital echo signals, and process the digital echo signals by algorithms of the invention. A user holds the transceiver 10 by the handle 12 to send probing ultrasound signals and to receive incoming ultrasound echoes. The transceiver 10 is placed in the communication cradle 42 that is in signal communication with a computer 52, and operates as an amniotic fluid volume measuring system. Two amniotic fluid volume-measuring systems are depicted as representative though fewer or more systems may be used. As used in this invention, a "server" can be any computer software or hardware that responds to requests or issues commands to or from a client. Likewise, the server may be accessible by one or more client computers via the Internet, or may be in communication over a LAN or other network.

Each amniotic fluid volume measuring systems includes the transceiver 10 for acquiring data from a patient. The transceiver 10 is placed in the cradle 52 to establish signal communication with the computer 52. Signal communication as illustrated is by a wired connection from the cradle 42 to the computer 52. Signal communication between the transceiver 10 and the computer 52 may also be by wireless means, for example, infrared signals or radio frequency signals. The wireless means of signal communication may occur between the cradle 42 and the computer 52, the transceiver 10 and the computer 52, or the transceiver 10 and the cradle 42.

A preferred first embodiment of the amniotic fluid volume measuring system includes each transceiver 10 being separately used on a patient and sending signals proportionate to the received and acquired ultrasound echoes to the computer 52 for storage. Residing in each computer 52 are imaging programs having instructions to prepare and analyze a plurality of one dimensional (1D) images from the stored signals and transforms the plurality of 1D images into the plurality of 2D scanplanes. The imaging programs also present 3D renderings from the plurality of 2D scanplanes. Also residing in each computer 52 are instructions to perform the additional ultrasound image enhancement procedures, including instructions to implement the image processing algorithms.

A preferred second embodiment of the amniotic fluid volume measuring system is similar to the first embodiment, but the imaging programs and the instructions to perform the additional ultrasound enhancement procedures are located on the server 56. Each computer 52 from each amniotic fluid volume measuring system receives the acquired signals from the transceiver 10 via the cradle 51 and stores the signals in the memory of the computer 52. The computer 52 subsequently retrieves the imaging programs and the instructions to perform the additional ultrasound enhancement procedures from the server 56. Thereafter, each computer 52 prepares the 1D images, 2D images, 3D renderings, and enhanced images from the retrieved imaging and ultrasound enhancement procedures. Results from the data analysis procedures are sent to the server 56 for storage.

A preferred third embodiment of the amniotic fluid volume measuring system is similar to the first and second embodiments, but the imaging programs and the instructions to perform the additional ultrasound enhancement procedures are located on the server 56 and executed on the server 56. Each computer 52 from each amniotic fluid volume measuring system receives the acquired signals from the transceiver 10 and via the cradle 51 sends the acquired signals in the memory of the computer 52. The computer 52 subsequently sends the stored signals to the server 56. In the server 56, the imaging programs and the instructions to perform the additional ultrasound enhancement procedures are executed to prepare the 1D images, 2D images, 3D renderings, and enhanced images from the server 56 stored signals. Results from the data analysis procedures are kept on the server 56, or alternatively, sent to the computer 52.

Figure 4:
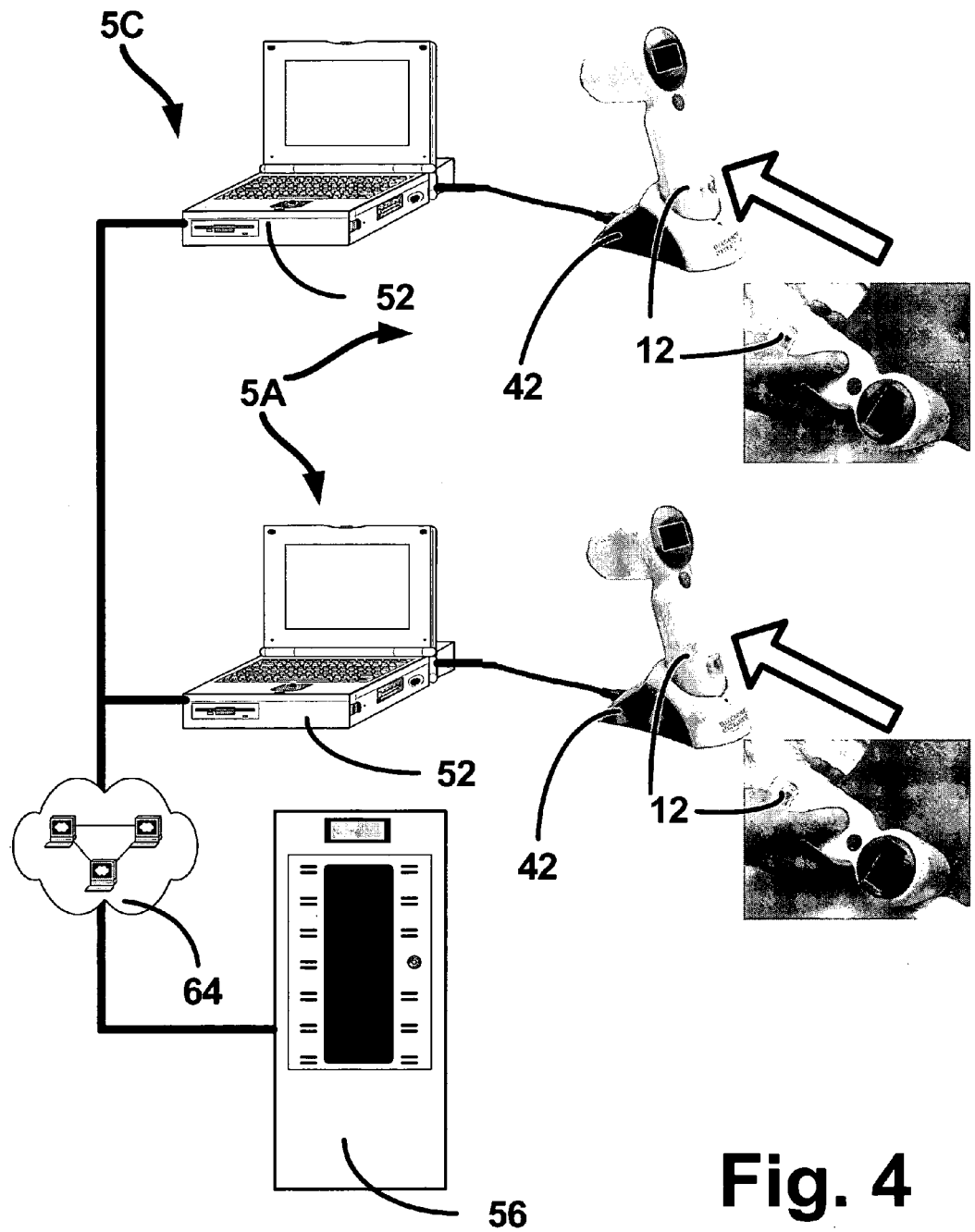
FIG. 4 is another alternate embodiment of an amniotic fluid volume measuring system in a schematic view of a plurality of transceivers in connection with a server over a network.

FIG. 4 is another embodiment of an amniotic volume fluid measuring system 5C presented in schematic view. The system 5C includes a plurality of amniotic fluid measuring systems 5A connected to a server 56 over the Internet or other network 64. FIG. 4 represents any of the first, second, or third embodiments of the invention advantageously deployed to other servers and computer systems through connections via the network.

FIG. 5A a graphical representation of a plurality of scan lines forming a single scan plane. FIG. 5A illustrates how ultrasound signals are used to make analyzable images, more specifically how a series of one-dimensional (1D) scanlines are used to produce a two-dimensional (2D) image. The 1D and 2D operational aspects of the single element transducer housed in the transceiver 10 is seen as it rotates mechanically about an angle $\phi$. A scanline 214 of length r migrates between a first limiting position 218 and a second limiting position 222 as determined by the value of the angle $\phi$, creating a fan-like 2D scanplane 210. In one preferred form, the transceiver 10 operates substantially at 3.7 MHz frequency and creates an approximately 18 cm deep scan line 214 and migrates within the angle $\phi$ having an angle of approximately 0.027 radians. A first motor tilts the transducer approximately 60° clockwise and then counterclockwise forming the fan-like 2D scanplane presenting an approximate 120° 2D sector image. A plurality of scanlines, each scanline substantially equivalent to scanline 214 is recorded, between the first limiting position 218 and the second limiting position 222 formed by the unique tilt angle $\phi$. The plurality of scanlines between the two extremes forms a scanplane 210. In the preferred embodiment, each scanplane contains 77 scan lines, although the number of lines can vary within the scope of this invention. The tilt angle $\phi$ sweeps through angles approximately between −60° and +60° for a total arc of approximately 120°.

FIG. 5B is a graphical representation of a plurality of scanplanes forming a three-dimensional array (3D) 240 having a substantially conic shape. FIG. 5B illustrates how a 3D rendering is obtained from the plurality of 2D scanplanes. Within each scanplane 210 are the plurality of scanlines, each scanline equivalent to the scanline 214 and sharing a common rotational angle $\theta$. In the preferred embodiment, each scanplane contains 77 scan lines, although the number of lines can vary within the scope of this invention. Each 2D sector image scanplane 210 with tilt angle $\phi$ and range r (equivalent to the scanline 214) collectively forms a 3D conic array 240 with rotation angle $\theta$. After gathering the 2D sector image, a second motor rotates the transducer between 3.75° or 7.5° to gather the next 120° sector image. This process is repeated until the transducer is rotated through 180°, resulting in the cone-shaped 3D conic array 240 data set with 24 planes rotationally assembled in the preferred embodiment. The conic array could have fewer or more planes rotationally assembled. For example, preferred alternate embodiments of the conic array could include at least two scanplanes, or a range of scanplanes from 2 to 48 scanplanes. The upper range of the scanplanes can be greater than 48 scanplanes. The tilt angle $\phi$ indicates the tilt of the scanline from the centerline in 2D sector image, and the rotation angle $\theta$, identifies the particular rotation plane the sector image lies in. Therefore, any point in this 3D data set can be isolated using coordinates expressed as three parameters, $P(r,\phi,\theta)$.

As the scanlines are transmitted and received, the returning echoes are interpreted as analog electrical signals by a transducer, converted to digital signals by an analog-to-digital converter, and conveyed to the digital signal processor of the computer system for storage and analysis to determine the locations of the amniotic fluid walls. The computer system is representationally depicted in FIGS. 3 and 4 and includes a microprocessor, random access memory (RAM), or other memory for storing processing instructions and data generated by the transceiver 10.

Figure 5C:
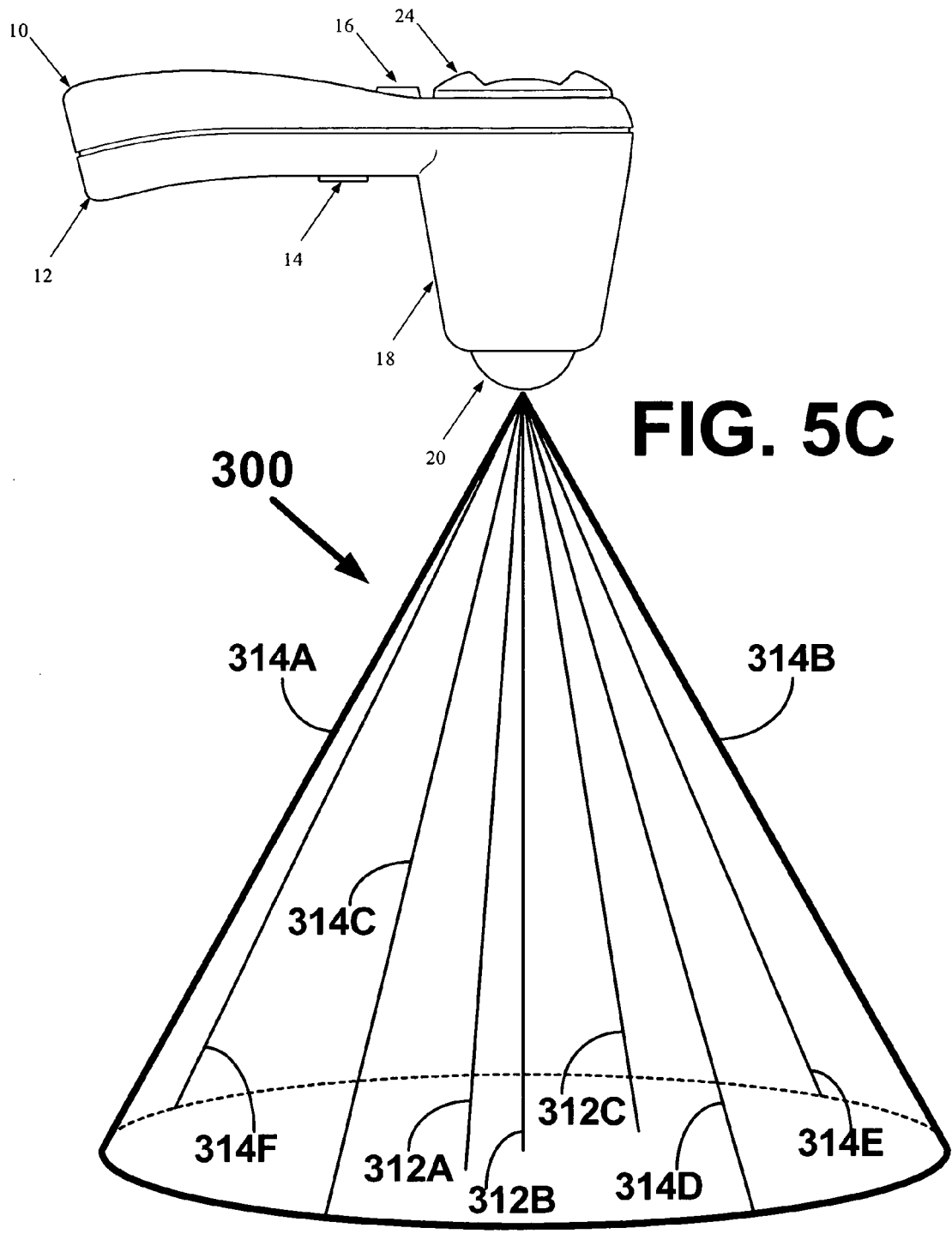
FIG. 5C is a graphical representation of a plurality of 3D distributed scanlines emanating from the transceiver forming a scancone.

FIG. 5C is a graphical representation of a plurality of 3D-distributed scanlines emanating from the transceiver 10 forming a scancone 300. The scancone 300 is formed by a plurality of 3D distributed scanlines that comprises a plurality of internal and peripheral scanlines. The scanlines are one-dimensional ultrasound A-lines that emanate from the transceiver 10 at different coordinate directions, that taken as an aggregate, from a conic shape. The 3D-distributed A-lines (scanlines) are not necessarily confined within a scanplane, but instead are directed to sweep throughout the internal and along the periphery of the scancone 300. The 3D-distributed scanlines not only would occupy a given scanplane in a 3D array of 2D scanplanes, but also the inter-scanplane spaces, from the conic axis to and including the conic periphery. The transceiver 10 shows the same illustrated features from FIG. 1, but is configured to distribute the ultrasound A-lines throughout 3D space in different coordinate directions to form the scancone 300.

The internal scanlines are represented by scanlines 312A-C. The number and location of the internal scanlines emanating from the transceiver 10 is the number of internal scanlines needed to be distributed within the scancone 300, at different positional coordinates, to sufficiently visualize structures or images within the scancone 300. The internal scanlines are not peripheral scanlines. The peripheral scanlines are represented by scanlines 314A-F and occupy the conic periphery, thus representing the peripheral limits of the scancone 300.

Figure 6:
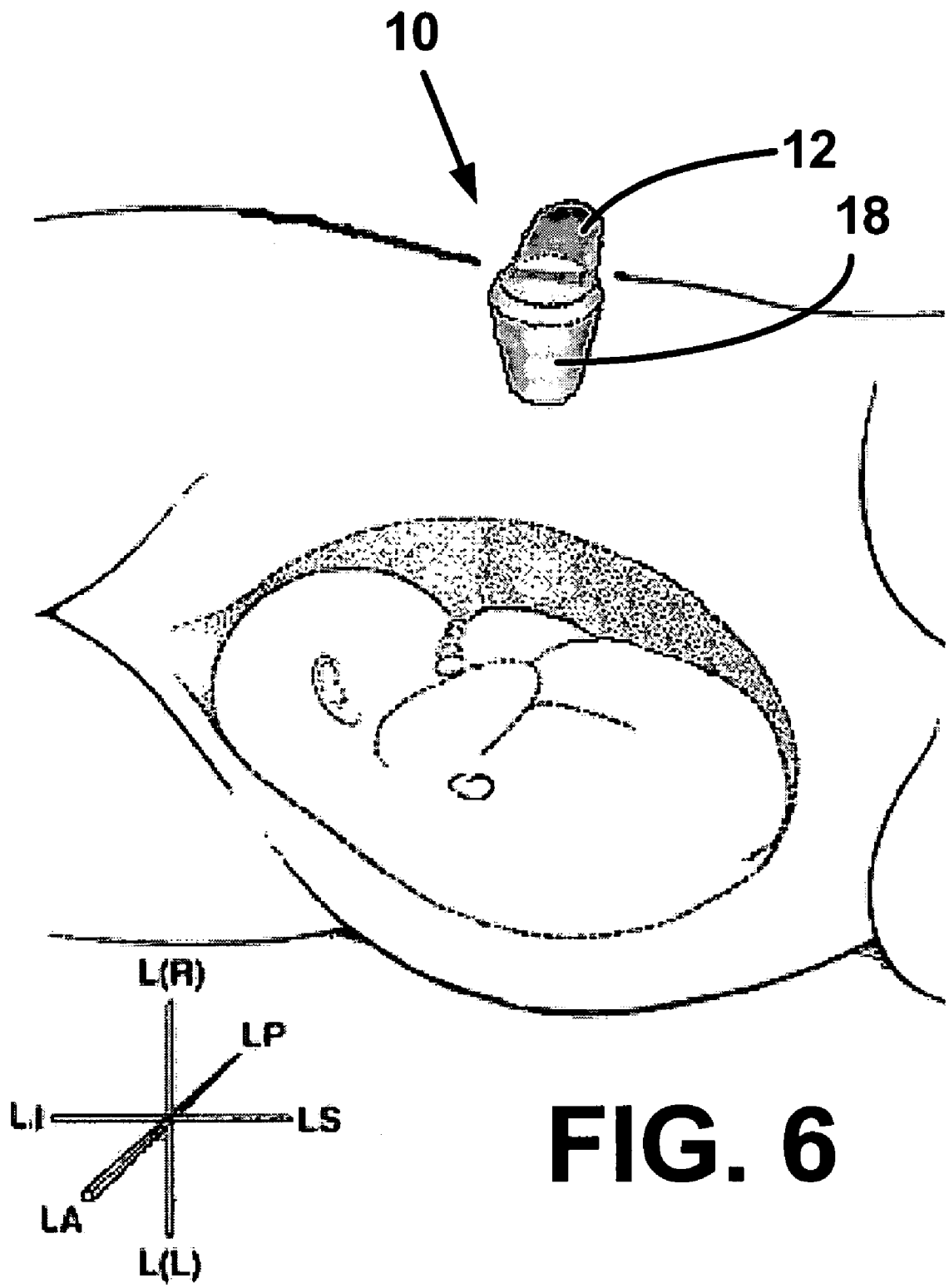
FIG. 6 is a depiction of the hand-held transceiver placed laterally on a patient trans-abdominally to transmit ultrasound and receive ultrasound echoes for processing to determine amniotic fluid volumes.

FIG. 6 is a depiction of the hand-held transceiver placed on a patient trans-abdominally to transmit probing ultrasound and receive ultrasound echoes for processing to determine amniotic fluid volumes. The transceiver 10 is held by the handle 12 to position over a patient to measure the volume of amniotic fluid in an amniotic sac over a baby. A plurality of axes for describing the orientation of the baby, the amniotic sac, and mother is illustrated. The plurality of axes includes a vertical axis depicted on the line L(R)-L(L) for left and right orientations, a horizontal axis LI-LS for inferior and superior orientations, and a depth axis LA-LP for anterior and posterior orientations.

FIG. 6 is representative of a preferred data acquisition protocol used for amniotic fluid volume determination. In this protocol, the transceiver 10 is the hand-held 3D ultrasound device (for example, model DCD372 from Diagnostic Ultrasound) and is used to image the uterus trans-abdominally. Initially during the targeting phase, the patient is in a supine position and the device is operated in a 2D continuous acquisition mode. A 2D continuous mode is where the data is continuously acquired in 2D and presented as a scanplane similar to the scanplane 210 on the display 24 while an operator physically moves the transceiver 10. An operator moves the transceiver 10 around on the maternal abdomen and the presses the trigger 14 of the transceiver 10 and continuously acquires real-time feedback presented in 2D on the display 24. Amniotic fluid, where present, visually appears as dark regions along with an alphanumeric indication of amniotic fluid area (for example, in $cm^2$) on the display 24. Based on this real-time information in terms of the relative position of the transceiver 10 to the fetus, the operator decides which side of the uterus has more amniotic fluid by the presentation on the display 24. The side having more amniotic fluid presents as regions having larger darker regions on the display 24. Accordingly, the side displaying a large dark region registers greater alphanumeric area while the side with less fluid shows displays smaller dark regions and proportionately registers smaller alphanumeric area on the display 24. While amniotic fluid is present throughout the uterus, its distribution in the uterus depends upon where and how the fetus is positioned within the uterus. There is usually less amniotic fluid around the fetus's spine and back and more amniotic fluid in front of its abdomen and around the limbs.

Based on fetal position information acquired from data gathered under continuous acquisition mode, the patient is placed in a lateral recumbent position such that the fetus is displaced towards the ground creating a large pocket of amniotic fluid close to abdominal surface where the transceiver 10 can be placed as shown in FIG. 6. For example, if large fluid pockets are found on the right side of the patient, the patient is asked to turn with the left side down and if large fluid pockets are found on the left side, the patient is asked to turn with the right side down.

After the patient has been placed in the desired position, the transceiver 10 is again operated in the 2D continuous acquisition mode and is moved around on the lateral surface of the patient's abdomen. The operator finds the location that shows the largest amniotic fluid area based on acquiring the largest dark region imaged and the largest alphanumeric value displayed on the display 24. At the lateral abdominal location providing the largest dark region, the transceiver 10 is held in a fixed position, the trigger 14 is released to acquire a 3D image comprising a set of arrayed scanplanes. The 3D image presents a rotational array of the scanplanes 210 similar to the 3D array 240.

In a preferred alternate data acquisition protocol, the operator can reposition the transceiver 10 to different abdominal locations to acquire new 3D images comprised of different scanplane arrays similar to the 3D array 240. Multiple scan cones obtained from different positions provide the operator the ability to image the entire amniotic fluid region from different view points. In the case of a single image cone being too small to accommodate a large AFV measurement, obtaining multiple 3D array 240 image cones ensures that the total volume of large AFV regions is determined. Multiple 3D images may also be acquired by pressing the top bottom 16 to select multiple conic arrays similar to the 3D array 240.

Depending on the position of the fetus relative to the location of the transceiver 10, a single image scan may present an underestimated volume of AFV due to amniotic fluid pockets that remain hidden behind the limbs of the fetus. The hidden amniotic fluid pockets present as unquantifiable shadow-regions.

To guard against underestimating AFV, repeated positioning the transceiver 10 and rescanning can be done to obtain more than one ultrasound view to maximize detection of amniotic fluid pockets. Repositioning and rescanning provides multiple views as a plurality of the 3D arrays 240 images cones. Acquiring multiple images cones improves the probability of obtaining initial estimates of AFV that otherwise could remain undetected and un-quantified in a single scan.

In an alternative scan protocol, the user determines and scans at only one location on the entire abdomen that shows the maximum amniotic fluid area while the patient is the supine position. As before, when the user presses the top button 16, 2D scanplane images equivalent to the scanplane 210 are continuously acquired and the amniotic fluid area on every image is automatically computed. The user selects one location that shows the maximum amniotic fluid area. At this location, as the user releases the scan button, a full 3D data cone is acquired and stored in the device's memory.

Figure 7:
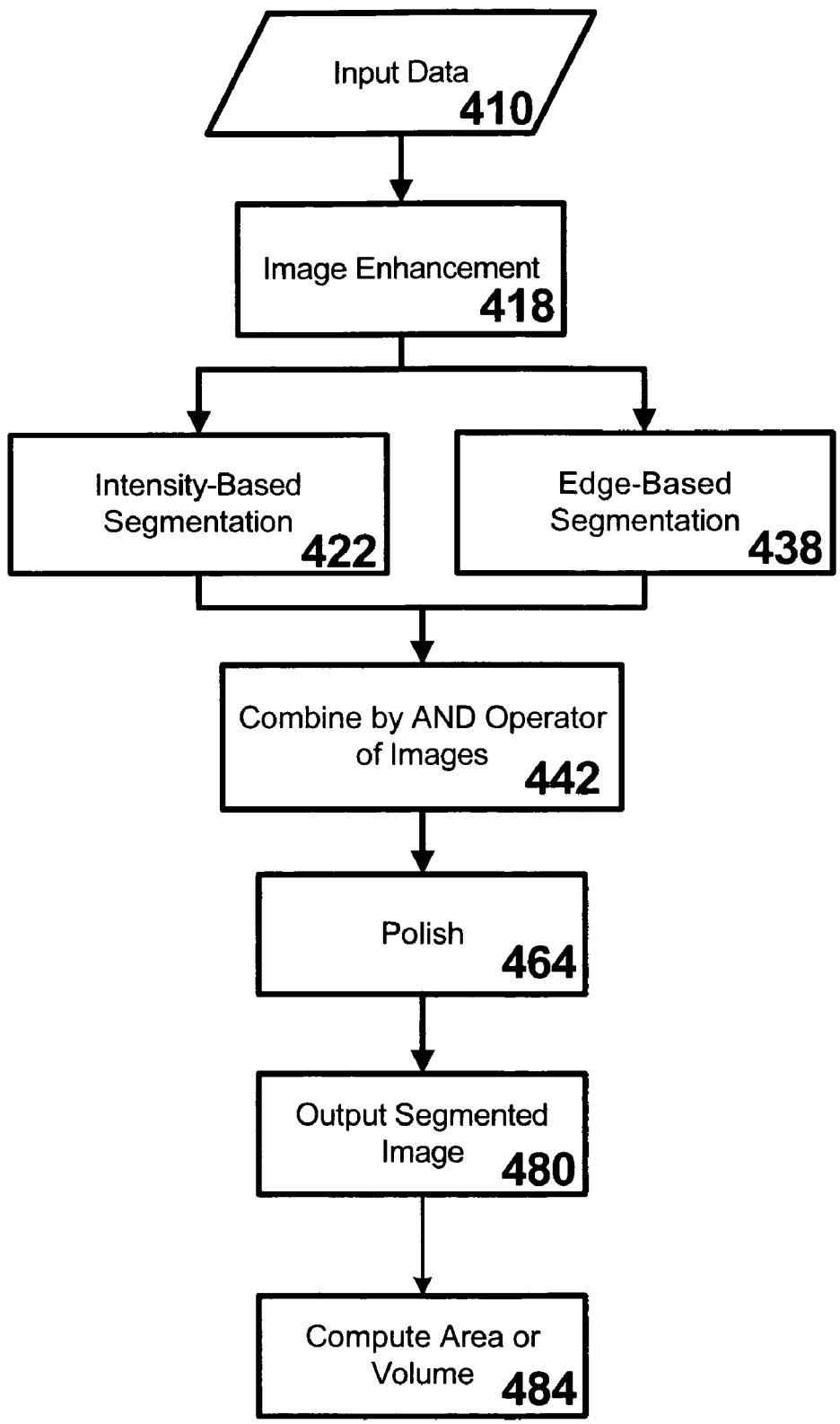
FIG. 7 shows a block diagram overview of the two-dimensional and three-dimensional Input, Image Enhancement, Intensity-Based Segmentation, Edge-Based Segmentation, Combine, Polish, Output, and Compute algorithms to visualize and determine the volume or area of amniotic fluid.

FIG. 7 shows a block diagram overview the image enhancement, segmentation, and polishing algorithms of the amniotic fluid volume measuring system. The enhancement, segmentation, and polishing algorithms are applied to each scanplane 210 or to the entire scan cone 240 to automatically obtain amniotic fluid regions. For scanplanes substantially equivalent to scanplane 210, the algorithms are expressed in two-dimensional terms and use formulas to convert scanplane pixels (picture elements) into area units. For the scan cones substantially equivalent to the 3D conic array 240, the algorithms are expressed in three-dimensional terms and use formulas to convert voxels (volume elements) into volume units.

The algorithms expressed in 2D terms are used during the targeting phase where the operator trans-abdominally positions and repositions the transceiver 10 to obtain real-time feedback about the amniotic fluid area in each scanplane. The algorithms expressed in 3D terms are used to obtain the total amniotic fluid volume computed from the voxels contained within the calculated amniotic fluid regions in the 3D conic array 240.

FIG. 7 represents an overview of a preferred method of the invention and includes a sequence of algorithms, many of which have sub-algorithms described in more specific detail in FIGS. 8A-F. FIG. 7 begins with inputting data of an unprocessed image at step 410. After unprocessed image data 410 is entered (e.g., read from memory, scanned, or otherwise acquired), it is automatically subjected to an image enhancement algorithm 418 that reduces the noise in the data (including speckle noise) using one or more equations while preserving the salient edges on the image using one or more additional equations. Next, the enhanced images are segmented by two different methods whose results are eventually combined. A first segmentation method applies an intensity-based segmentation algorithm 422 that determines all pixels that are potentially fluid pixels based on their intensities. A second segmentation method applies an edge-based segmentation algorithm 438 that relies on detecting the fluid and tissue interfaces. The images obtained by the first segmentation algorithm 422 and the images obtained by the second segmentation algorithm 438 are brought together via a combination algorithm 442 to provide a substantially segmented image. The segmented image obtained from the combination algorithm 442 are then subjected to a polishing algorithm 464 in which the segmented image is cleaned-up by filling gaps with pixels and removing unlikely regions. The image obtained from the polishing algorithm 464 is outputted 480 for calculation of areas and volumes of segmented regions-of-interest. Finally the area or the volume of the segmented region-of-interest is computed 484 by multiplying pixels by a first resolution factor to obtain area, or voxels by a second resolution factor to obtain volume. For example, for pixels having a size of 0.8 mm by 0.8 mm, the first resolution or conversion factor for pixel area is equivalent to 0.64 mm², and the second resolution or conversion factor for voxel volume is equivalent to 0.512 mm³. Different unit lengths for pixels and voxels may be assigned, with a proportional change in pixel area and voxel volume conversion factors.

The enhancement, segmentation and polishing algorithms depicted in FIG. 7 for measuring amniotic fluid areas or volumes are not limited to scanplanes assembled into rotational arrays equivalent to the 3D array 240. As additional examples, the enhancement, segmentation and polishing algorithms depicted in FIG. 7 apply to translation arrays and wedge arrays. Translation arrays are substantially rectilinear image plane slices from incrementally repositioned ultrasound transceivers that are configured to acquire ultrasound rectilinear scanplanes separated by regular or irregular rectilinear spaces. The translation arrays can be made from transceivers configured to advance incrementally, or may be hand-positioned incrementally by an operator. The operator obtains a wedge array from ultrasound transceivers configured to acquire wedge-shaped scanplanes separated by regular or irregular angular spaces, and either mechanistically advanced or hand-tilted incrementally. Any number of scanplanes can be either translationally assembled or wedge-assembled ranges, but preferably in ranges greater than 2 scanplanes.

Other preferred embodiments of the enhancement, segmentation and polishing algorithms depicted in FIG. 7 may be applied to images formed by line arrays, either spiral distributed or reconstructed random-lines. The line arrays are defined using points identified by the coordinates expressed by the three parameters, $P(r,\phi,\theta)$, where the values or r, $\phi$, and $\theta$ can vary.

The enhancement, segmentation and polishing algorithms depicted in FIG. 7 are not limited to ultrasound applications but may be employed in other imaging technologies utilizing scanplane arrays or individual scanplanes. For example, biological-based and non-biological-based images acquired using infrared, visible light, ultraviolet light, microwave, x-ray computed tomography, magnetic resonance, gamma rays, and positron emission are images suitable for the algorithms depicted in FIG. 7. Furthermore, the algorithms depicted in FIG. 7 can be applied to facsimile transmitted images and documents.

FIGS. 8A-E depict expanded details of the preferred embodiments of enhancement, segmentation, and polishing algorithms described in FIG. 7. Each of the following greater detailed algorithms are either implemented on the transceiver 10 itself or are implemented on the host computer 52 or on the server 56 computer to which the ultrasound data is transferred.

FIG. 8A depicts the sub-algorithms of Image Enhancement. The sub-algorithms include a heat filter 514 to reduce noise and a shock filter 518 to sharpen edges. A combination of the heat and shock filters works very well at reducing noise and sharpening the data while preserving the significant discontinuities. First, the noisy signal is filtered using a 1D heat filter (Equation E1 below), which results in the reduction of noise and smoothing of edges. This step is followed by a shock-filtering step 518 (Equation E2 below), which results in the sharpening of the blurred signal. Noise reduction and edge sharpening is achieved by application of the following equations E1-E2. The algorithm of the heat filter 514 uses a heat equation E1. The heat equation E1 in partial differential equation (PDE) form for image processing is expressed as:

$$\frac{\partial u}{\partial t} = \frac{\partial^2 u}{\partial x^2} + \frac{\partial^2 u}{\partial y^2}, \quad \text{E1}$$

where u is the image being processed. The image u is 2D, and is comprised of an array of pixels arranged in rows along the x-axis, and an array of pixels arranged in columns along the y-axis. The pixel intensity of each pixel in the image u has an initial input image pixel intensity (I) defined as $u_0=I$. The value of I depends on the application, and commonly occurs within ranges consistent with the application. For example, I can be as low as 0 to 1, or occupy middle ranges between 0 to 127 or 0 to 512. Similarly, I may have values occupying higher ranges of 0 to 1024 and 0 to 4096, or greater. The heat equation E1 results in a smoothing of the image and is equivalent to the Gaussian filtering of the image. The larger the number of iterations that it is applied for the more the input image is smoothed or blurred and the more the noise that is reduced.

The shock filter 518 is a PDE used to sharpen images as detailed below. The two dimensional shock filter E2 is expressed as:

$$\frac{\partial u}{\partial t} = -F(l(u))\|\nabla u\|, \quad \text{E2}$$

where u is the image processed whose initial value is the input image pixel intensity (I): $u_0=I$ where the l(u) term is the Laplacian of the image u, F is a finction of the Laplacian, and $\|\nabla u\|$ is the 2D gradient magnitude of image intensity defined by equation E3.

$$\|\nabla u\| = \sqrt{u_x^2 + y^2}, \quad \text{E3}$$

where
$u^2_x$=the square of the partial derivative of the pixel intensity (u) along the x-axis,
$u^2_y$=the square of the partial derivative of the pixel intensity (u) along the y-axis,
the Laplacian t(u) of the image, u, is expressed in equation E4 as $$l(u) = u_{xx}u_x^2 + 2u_{xy}u_xu_y + u_{yy}u_y^2 \quad \text{E4}$$

where equation E4 relates to equation E1 as follows:
$u_x$ is the first partial derivative $$\frac{\partial u}{\partial x}$$

of u along the x-axis,
$u_y$ is the first partial derivative $$\frac{\partial u}{\partial y}$$

of u along the y-axis,
$u_x^2$ is the square of the first partial derivative $$\frac{\partial u}{\partial x}$$

of u along the x-axis,
$u_y^2$ is the square of the first partial derivative $$\frac{\partial u}{\partial y}$$

of u along the y-axis,
$u_{xx}$ is the second partial derivative $$\frac{\partial^2 u}{\partial x^2}$$

of u along the x-axis,
$u_{yy}$ is the second partial derivative $$\frac{\partial^2 u}{\partial y^2}$$

of u along the y-axis,
$u_{xy}$ is cross multiple first partial derivative $$\frac{\partial u}{\partial x dy}$$

of u along the x and y axes, and
the sign of the function F modifies the Laplacian by the image gradient values selected to avoid placing spurious edges at points with small gradient values:

$$F(l(u)) = 1, \text{ if } l(u) > 0 \text{ and } \|\nabla u\| > t$$
$$= -1, \text{ if } l(u) < 0 \text{ and } \|\nabla u\| > t$$
$$= 0, \text{ otherwise}$$

where t is a threshold on the pixel gradient value $\|\nabla u\|$.

The combination of heat filtering and shock filtering produces an enhanced image ready to undergo the intensity-based and edge-based segmentation algorithms as discussed below.

FIG. 8B depicts the sub-algorithms of Intensity-Based Segmentation (step 422 in FIG. 7). The intensity-based segmentation step 422 uses a "k-means" intensity clustering 522 technique where the enhanced image is subjected to a categorizing "k-means" clustering algorithm. The "k-means" algorithm categorizes pixel intensities into white, gray, and black pixel groups. Given the number of desired clusters or groups of intensities (k), the k-means algorithm is an iterative algorithm comprising four steps:

1. Initially determine or categorize cluster boundaries by defining a minimum and a maximum pixel intensity value for every white, gray, or black pixels into groups or k-clusters that are equally spaced in the entire intensity range.

2. Assign each pixel to one of the white, gray or black k-clusters based on the currently set cluster boundaries.

3. Calculate a mean intensity for each pixel intensity k-cluster or group based on the current assignment of pixels into the different k-clusters. The calculated mean intensity is defined as a cluster center. Thereafter, new cluster boundaries are determined as mid points between cluster centers.

4. Determine if the cluster boundaries significantly change locations from their previous values. Should the cluster boundaries change significantly from their previous values, iterate back to step 2, until the cluster centers do not change significantly between iterations. Visually, the clustering process is manifest by the segmented image and repeated iterations continue until the segmented image does not change between the iterations.

The pixels in the cluster having the lowest intensity value—the darkest cluster—are defined as pixels associated with amniotic fluid. For the 2D algorithm, each image is clustered independently of the neighboring images. For the 3D algorithm, the entire volume is clustered together. To make this step faster, pixels are sampled at 2 or any multiple sampling rate factors before determining the cluster boundaries. The cluster boundaries determined from the down-sampled data are then applied to the entire data.

FIG. 8C depicts the sub-algorithms of Edge-Based Segmentation (step 438 in FIG. 7) and uses a sequence of four sub-algorithms. The sequence includes a spatial gradients 526 algorithm, a hysteresis threshold 530 algorithm, a Region-of-Interest (ROI) 534 algorithm, and a matching edges filter 538 algorithm.

The spatial gradient 526 computes the x-directional and y-directional spatial gradients of the enhanced image. The Hysteresis threshold 530 algorithm detects salient edges. Once the edges are detected, the regions defined by the edges are selected by a user employing the ROI 534 algorithm to select regions-of-interest deemed relevant for analysis.

Since the enhanced image has very sharp transitions, the edge points can be easily determined by taking x- and y-derivatives using backward differences along x- and y-directions. The pixel gradient magnitude $\|\nabla I\|$ is then computed from the x- and y-derivative image in equation E5 as:

$$\|\nabla I\| \sqrt{I_x^2 + I_y^2} \qquad \text{E5}$$

Where
$I_x^2$=the square of x-derivative of intensity; and
$I_y^2$=the square of y-derivative of intensity along the y-axis.

Significant edge points are then determined by thresholding the gradient magnitudes using a hysteresis thresholding operation. Other thresholding methods could also be used. In hysteresis thresholding 530, two threshold values, a lower threshold and a higher threshold, are used. First, the image is thresholded at the lower threshold value and a connected component labeling is carried out on the resulting image. Next, each connected edge component is preserved which has at least one edge pixel having a gradient magnitude greater than the upper threshold. This kind of thresholding scheme is good at retaining long connected edges that have one or more high gradient points.

In the preferred embodiment, the two thresholds are automatically estimated. The upper gradient threshold is estimated at a value such that at most 97% of the image pixels are marked as non-edges. The lower threshold is set at 50% of the value of the upper threshold. These percentages could be different in different implementations. Next, edge points that lie within a desired region-of-interest are selected 534. This region of interest selection 534 excludes points lying at the image boundaries and points lying too close to or too far from the transceiver 10. Finally, the matching edge filter 538 is applied to remove outlier edge points and fill in the area between the matching edge points.

The edge-matching algorithm 538 is applied to establish valid boundary edges and remove spurious edges while filling the regions between boundary edges. Edge points on an image have a directional component indicating the direction of the gradient. Pixels in scanlines crossing a boundary edge location will exhibit two gradient transitions depending on the pixel intensity directionality. Each gradient transition is given a positive or negative value depending on the pixel intensity directionality. For example, if the scanline approaches an echo reflective bright wall from a darker region, then an ascending transition is established as the pixel intensity gradient increases to a maximum value, i.e., as the transition ascends from a dark region to a bright region. The ascending transition is given a positive numerical value. Similarly, as the scanline recedes from the echo reflective wall, a descending transition is established as the pixel intensity gradient decreases to or approaches a minimum value. The descending transition is given a negative numerical value.

Valid boundary edges are those that exhibit ascending and descending pixel intensity gradients, or equivalently, exhibit paired or matched positive and negative numerical values. The valid boundary edges are retained in the image. Spurious or invalid boundary edges do not exhibit paired ascending-descending pixel intensity gradients, i.e., do not exhibit paired or matched positive and negative numerical values. The spurious boundary edges are removed from the image.

For amniotic fluid volume related applications, most edge points for amniotic fluid surround a dark, closed region, with directions pointing inwards towards the center of the region. Thus, for a convex-shaped region, the direction of a gradient for any edge point, the edge point having a gradient direction approximately opposite to the current point represents the matching edge point. Those edge points exhibiting an assigned positive and negative value are kept as valid edge points on the image because the negative value is paired with its positive value counterpart. Similarly, those edge point candidates having unmatched values, i.e., those edge point candidates not having a negative-positive value pair, are deemed not to be true or valid edge points and are discarded from the image.

The matching edge point algorithm 538 delineates edge points not lying on the boundary for removal from the desired dark regions. Thereafter, the region between any two matching edge points is filled in with non-zero pixels to establish edge-based segmentation. In a preferred embodiment of the invention, only edge points whose directions are primarily oriented co-linearly with the scanline are sought to permit the detection of matching front wall and back wall pairs.

Returning to FIG. 7, once Intensity-Based 422 and Edge-Based Segmentation 438 is completed, both segmentation methods use a combining step that combines the results of intensity-based segmentation 422 step and the edge-based segmentation 438 step using an AND Operator of Images 442. The AND Operator of Images 442 is achieved by a pixel-wise Boolean AND operator 442 step to produce a segmented image by computing the pixel intersection of two images. The Boolean AND operation 442 represents the pixels as binary numbers and the corresponding assignment of an assigned intersection value as a binary number 1 or 0 by the combination of any two pixels. For example, consider any two pixels, say $pixel_A$ and $pixel_B$, which can have a 1 or 0 as assigned values. If $pixel_A$'s value is 1, and $pixel_B$'s value is 1, the assigned intersection value of $pixel_A$ and $pixel_B$ is 1. If the binary value of $pixel_A$ and $pixel_B$ are both 0, or if either $pixel_A$ or $pixel_B$ is 0, then the assigned intersection value of $pixel_A$ and $pixel_B$ is 0. The Boolean AND operation 542 takes the binary any two digital images as input, and outputs a third image with the pixel values made equivalent to the intersection of the two input images.

Figure 8D:
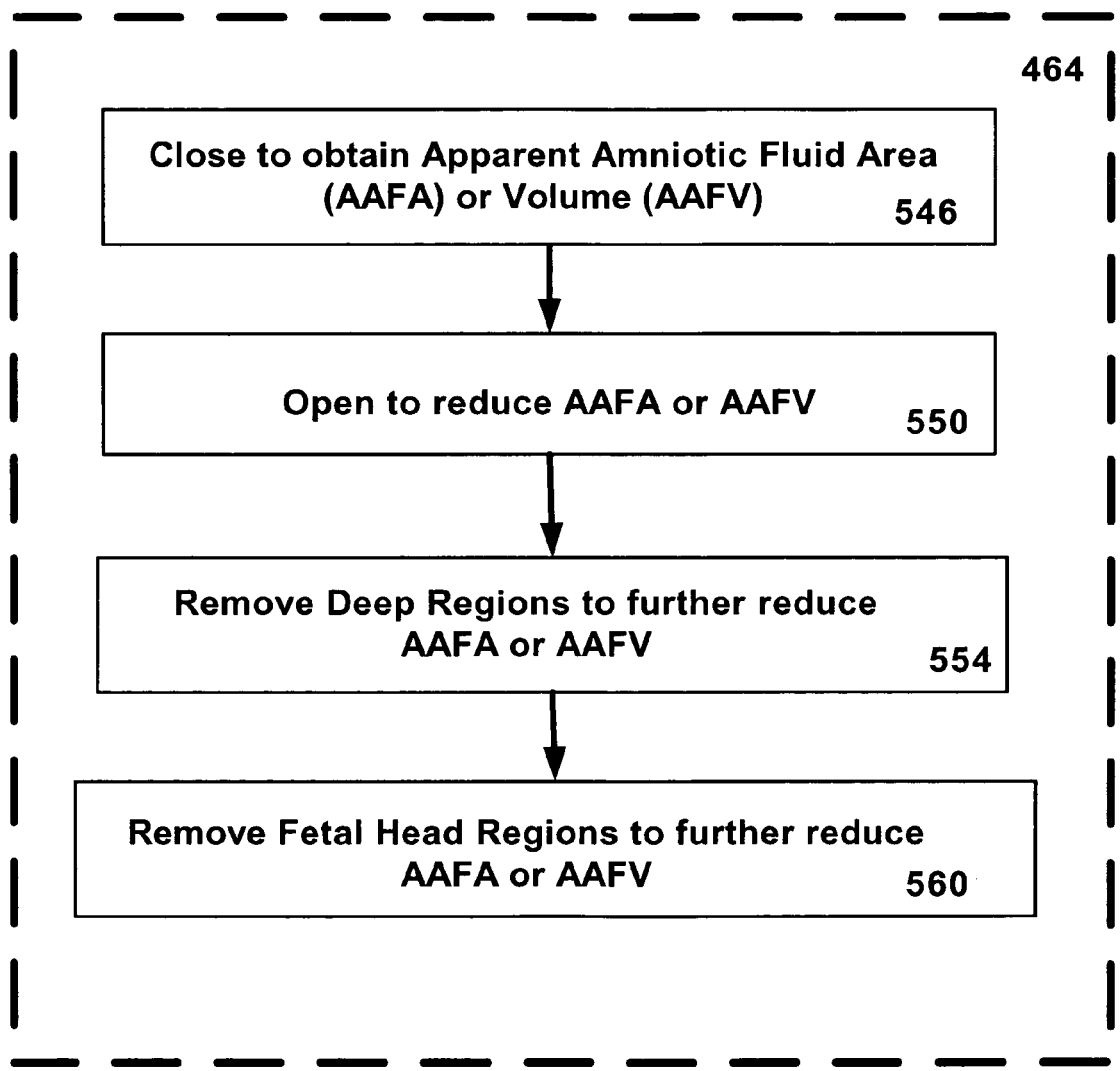
FIG. 8D depicts the sub-algorithms of the Polish algorithm, including Close, Open, Remove Deep Regions, and Remove Fetal Head Regions.

Upon completion of the AND Operator of Images 442 algorithm, the polish 464 algorithm of FIG. 7 is comprised of multiple sub-algorithms. FIG. 8D depicts the sub-algorithms of the Polish 464 algorithm, including a Close 546 algorithm, an Open 550 algorithm, a Remove Deep Regions 554 algorithm, and a Remove Fetal Head Regions 560 algorithm.

Closing and opening algorithms are operations that process images based on the knowledge of the shape of objects contained on a black and white image, where white represents foreground regions and black represents background regions. Closing serves to remove background features on the image that are smaller than a specified size. Opening serves to remove foreground features on the image that are smaller than a specified size. The size of the features to be removed is specified as an input to these operations. The opening algorithm 550 removes unlikely amniotic fluid regions from the segmented image based on a-priori knowledge of the size and location of amniotic fluid pockets.

Referring to FIG. 8D, the closing 546 algorithm obtains the Apparent Amniotic Fluid Area (AAFA) or Volume (AAFV) values. The AAFA and AAFV values are "Apparent" and maximal because these values may contain region areas or region volumes of non-amniotic origin unknowingly contributing to and obscuring what otherwise would be the true amniotic fluid volume. For example, the AAFA and AAFV values contain the true amniotic volumes, and possibly as well areas or volumes due to deep tissues and undetected fetal head volumes. Thus the apparent area and volume values require correction or adjustments due to unknown contributions of deep tissue and of the fetal head in order to determine an Adjusted Amniotic Fluid Area (AdAFA) value or Volume (AdAVA) value 568.

The AdAFA and AdAVA values obtained by the Close 546 algorithm are reduced by the morphological opening algorithm 550. Thereafter, the AdAFA and AdAVA values are further reduced by removing areas and volumes attributable to deep regions by using the Remove Deep Regions 554 algorithm. Thereafter, the polishing algorithm 464 continues by applying a fetal head region detection algorithm 560.

Figure 8E:
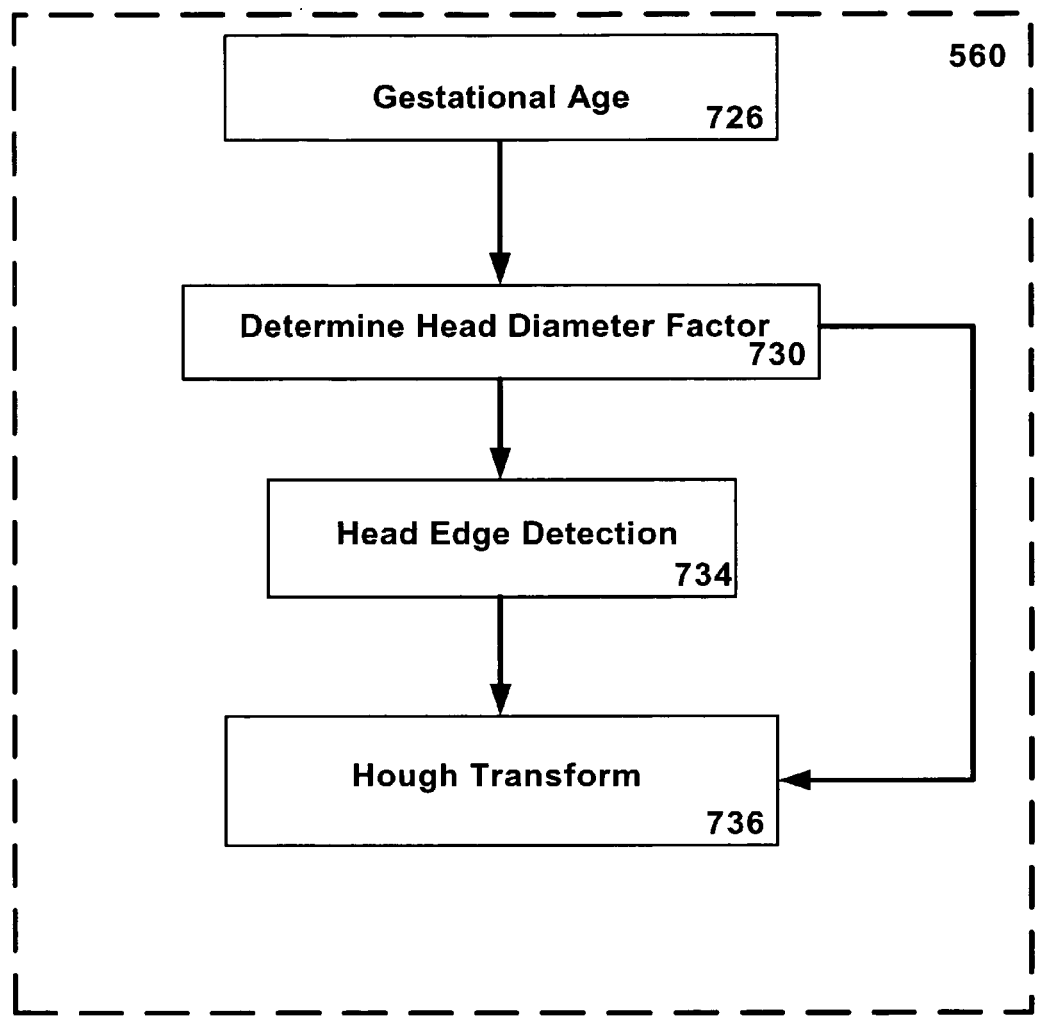
FIG. 8E depicts the sub-algorithms of the Remove Fetal Head Regions sub-algorithm.

FIG. 8E depicts the sub-algorithms of the Remove Fetal Head Regions sub-algorithm 560. The basic idea of the sub-algorithms of the fetal head detection algorithm 560 is that the edge points that potentially represent a fetal skull are detected. Thereafter, a circle finding algorithm to determine the best-fitting circle to these fetal skull edges is implemented. The radii of the circles that are searched are known a priori based on the fetus' gestational age. The best fitting circle whose fitting metric lies above a certain pre-specified threshold is marked as the fetal head and the region inside this circle is the fetal head region. The algorithms include a gestational Age 726 input, a determine head diameter factor 730 algorithm, a Head Edge Detection algorithm, 734, and a Hough transform procedure 736.

Fetal brain tissue has substantially similar ultrasound echo qualities as presented by amniotic fluid. If not detected and subtracted from amniotic fluid volumes, fetal brain tissue volumes will be measured as part of the total amniotic fluid volumes and lead to an overestimation and false diagnosis of oligo or poly-hyraminotic conditions. Thus detecting fetal head position, measuring fetal brain matter volumes, and deducting the fetal brain matter volumes from the amniotic fluid volumes to obtain a corrected amniotic fluid volume serves to establish accurately measure amniotic fluid volumes.

The gestational age input 726 begins the fetal head detection algorithm 560 and uses a head dimension table to obtain ranges of head bi-parietal diameters (BPD) to search for (e.g., 30 week gestational age corresponds to a 6 cm head diameter). The head diameter range is input to both the Head Edge Detection, 734, and the Hough Transform, 736. The head edge detection 734 algorithm seeks out the distinctively bright ultrasound echoes from the anterior and posterior walls of the fetal skull while the Hough Transform algorithm, 736, finds the fetal head using circular shapes as models for the fetal head in the Cartesian image (pre-scan conversion to polar form).

Scanplanes processed by steps 522, 538, 530, are input to the head edge detection step 734. Applied as the first step in the fetal head detection algorithm 734 is the detection of the potential head edges from among the edges found by the matching edge filter. The matching edge 538 filter outputs pairs of edge points potentially belonging to front walls or back walls. Not all of these walls correspond to fetal head locations. The edge points representing the fetal head are determined using the following heuristics:

(1) Looking along a one dimensional A-mode scan line, fetal head locations present a corresponding matching gradient in the opposing direction within a short distance approximately the same size as the thickness of the fetal skull. This distance is currently set to a value 1 cm.

(2) The front wall and the back wall locations of the fetal head are within a range of diameters corresponding to the expected diameter 730 for the gestational age 726 of the fetus. Walls that are too close or too far are not likely to be head locations.

(3) A majority of the pixels between the front and back wall locations of the fetal head lie within the minimum intensity cluster as defined by the output of the clustering algorithm 422. The percentage of pixels that need to be dark is currently defined to be 80%.

The pixels found satisfying these features are then vertically dilated to produce a set of thick fetal head edges as the output of Head Edge Detection, 734.

Figure 8F:
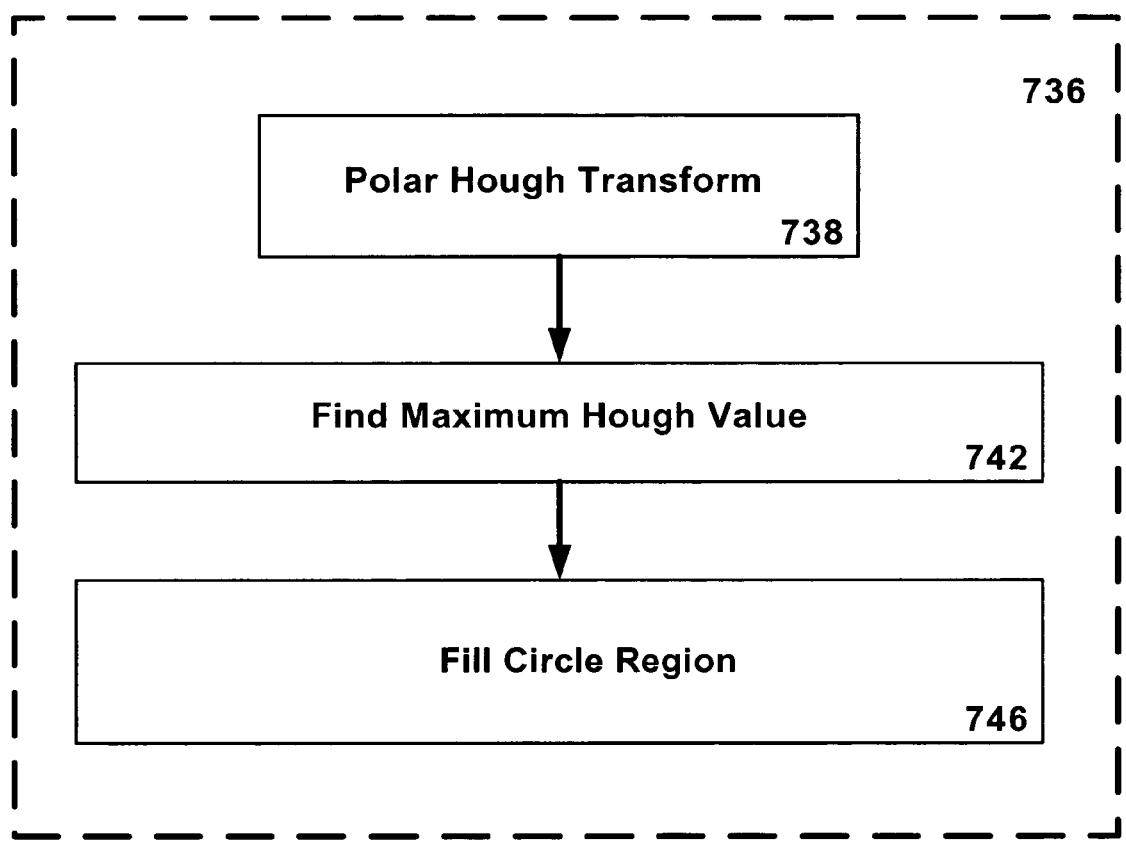
FIG. 8F depicts the sub-algorithms of the Hough Transform sub-algorithm.

FIG. 8F depicts the sub-algorithms of the Hough transform procedure 736. The sub-algorithms include a Polar Hough Transform 738 algorithm, a find maximum Hough value 742 algorithm 742, and a fill circle region 746. The Polar Hough Transform algorithm looks for fetal head structures in polar coordinate terms by converting from Cartesian coordinates using a plurality of equations. The fetal head, which appears like a circle in a 3D scan-converted Cartesian coordinate image, has a different shape in the pre-scan converted polar space. The fetal head shape is expressed in terms of polar coordinate terms explained as follows:

The coordinates of a circle in the Cartesian space (x,y) with center $(x_0, y_0)$ and radius R are defined for an angle 0 are derived and defined in equation E5 as:

$$x = R \cos \theta + x_0$$

$$y = R \sin \theta + y_0$$

$$\Rightarrow (x-x_0)^2 + (y-y_0)^2 = R^2 \qquad \text{E5}$$

In polar space, the coordinates $(r, \phi)$, with respect to the center $(r_0, \phi_0)$, are derived and defined in equation E6 as:

$$r \sin \phi = R \cos \theta + r_0 \sin \phi_0$$

$$r \cos \phi = R \sin \theta + r_0 \cos \phi_0$$

$$\Rightarrow (r \sin \phi - r_0 \sin \phi_0)^2 + (r \cos \phi - r_0 \cos \phi_0)^2 = R^2 \qquad \text{E6}$$

The Hough transform 736 algorithm using equations E5 and E6 attempts to find the best-fit circle to the edges of an image. A circle in the polar space is defined by a set of three parameters, $(r_0, \phi_0, R)$ representing the center and the radius of the circle.

The basic idea for the Hough transform 736 is as follows. Suppose a circle is sought having a fixed radius (say, R1) for which the best center of the circle is similarly sought. Now, every edge point on the input image lies on a potential circle whose center lays R1 pixels away from it. The set of potential centers themselves form a circle of radius R1 around each edge pixel. Now, drawing potential circles of radius R1 around each edge pixel, the point at which most circles intersect, a center of the circle that represents a best-fit circle to the given edge points is obtained. Therefore, each pixel in the Hough transform output contains a likelihood value that is simply the count of the number of circles passing through that point.

Figure 9:
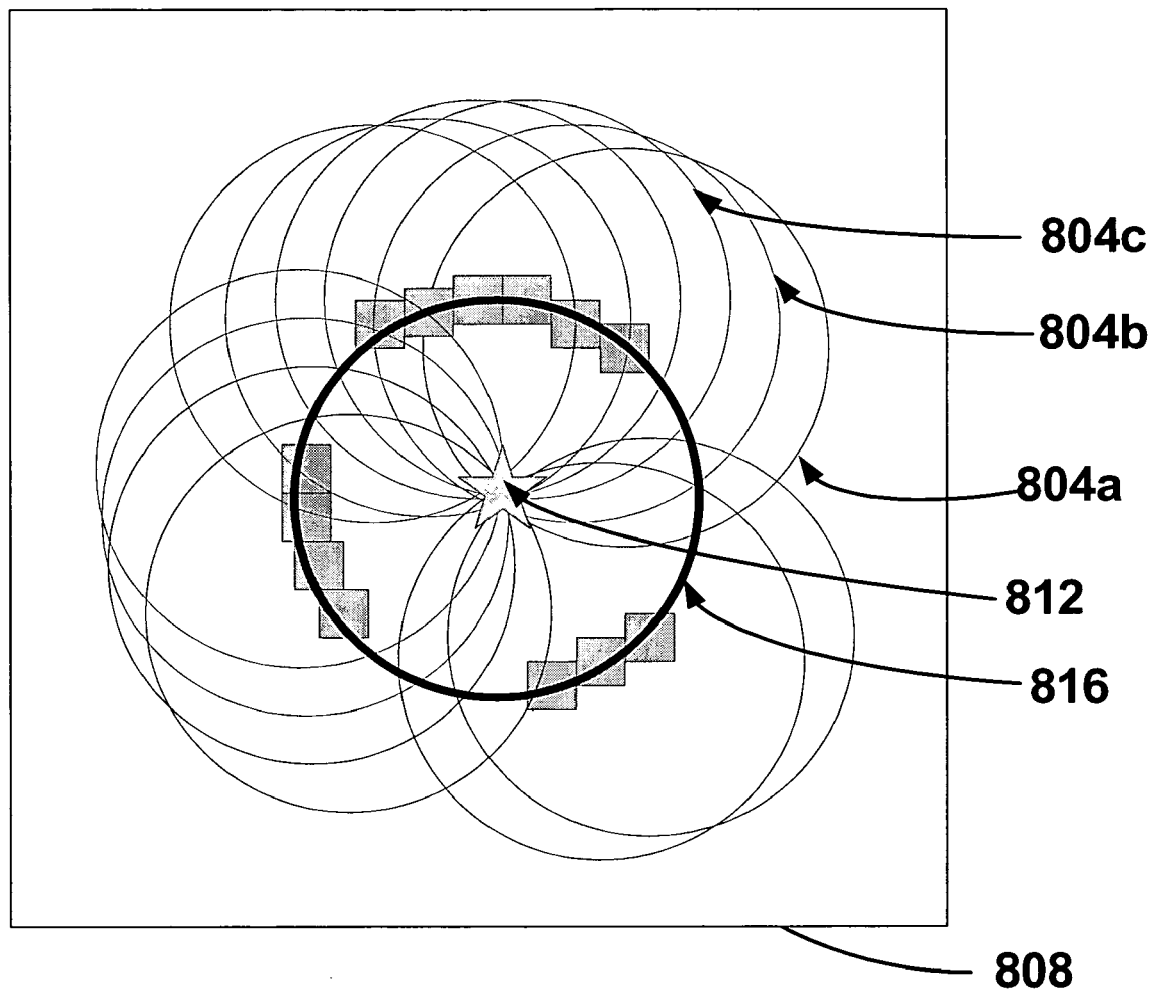
FIG. 9 depicts the operation of a circular Hough transform algorithm.

FIG. 9 illustrates the Hough Transform 736 algorithm for a plurality of circles with a fixed radius in a Cartesian coordinate system. A portion of the plurality of circles is represented by a first circle 804a, a second circle 804b, and a third circle 804c. A plurality of edge pixels are represented as gray squares and an edge pixel 808 is shown. A circle is drawn around each edge pixel to distinguish a center location 812 of a best-fit circle 816 passing through each edge pixel point; the point of the center location through which most such circles pass (shown by a gray star 812) is the center of the best-fit circle 816 presented as a thick dark line. The circumference of the best fit circle 816 passes substantially through is central portion of each edge pixel, represented as a series of squares substantially equivalent to the edge pixel 808.

This search for best fitting circles can be easily extended to circles with varying radii by adding one more degree of freedom—however, a discrete set of radii around the mean radii for a given gestational age makes the search significantly faster, as it is not necessary to search all possible radii.

The next step in the head detection algorithm is selecting or rejecting best-fit circles based on its likelihood, in the find maximum Hough Value 742 algorithm. The greater the number of circles passing through a given point in the Houghspace, the more likely it is to be the center of a best-fit circle. A 2D metric as a maximum Hough value 742 of the Hough transform 736 output is defined for every image in a dataset. The 3D metric is defined as the maximum of the 2D metrics for the entire 3D dataset. A fetal head is selected on an image depending on whether its 3D metric value exceeds a preset 3D threshold and also whether the 2D metric exceeds a preset 2D threshold. The 3D threshold is currently set at 7 and the 2D threshold is currently set at 5. These thresholds have been determined by extensive training on images where the fetal head was known to be present or absent.

Thereafter, the fetal head detection algorithm concludes with a fill circle region 746 that incorporates pixels to the image within the detected circle. The fill circle region 746 algorithm fills the inside of the best fitting polar circle. Accordingly, the fill circle region 746 algorithm encloses and defines the area of the fetal brain tissue, permitting the area and volume to be calculated and deducted via algorithm 554 from the apparent amniotic fluid area and volume (AAFA or AAFV) to obtain a computation of the corrected amniotic fluid area or volume via algorithm 484.

Figure 10:
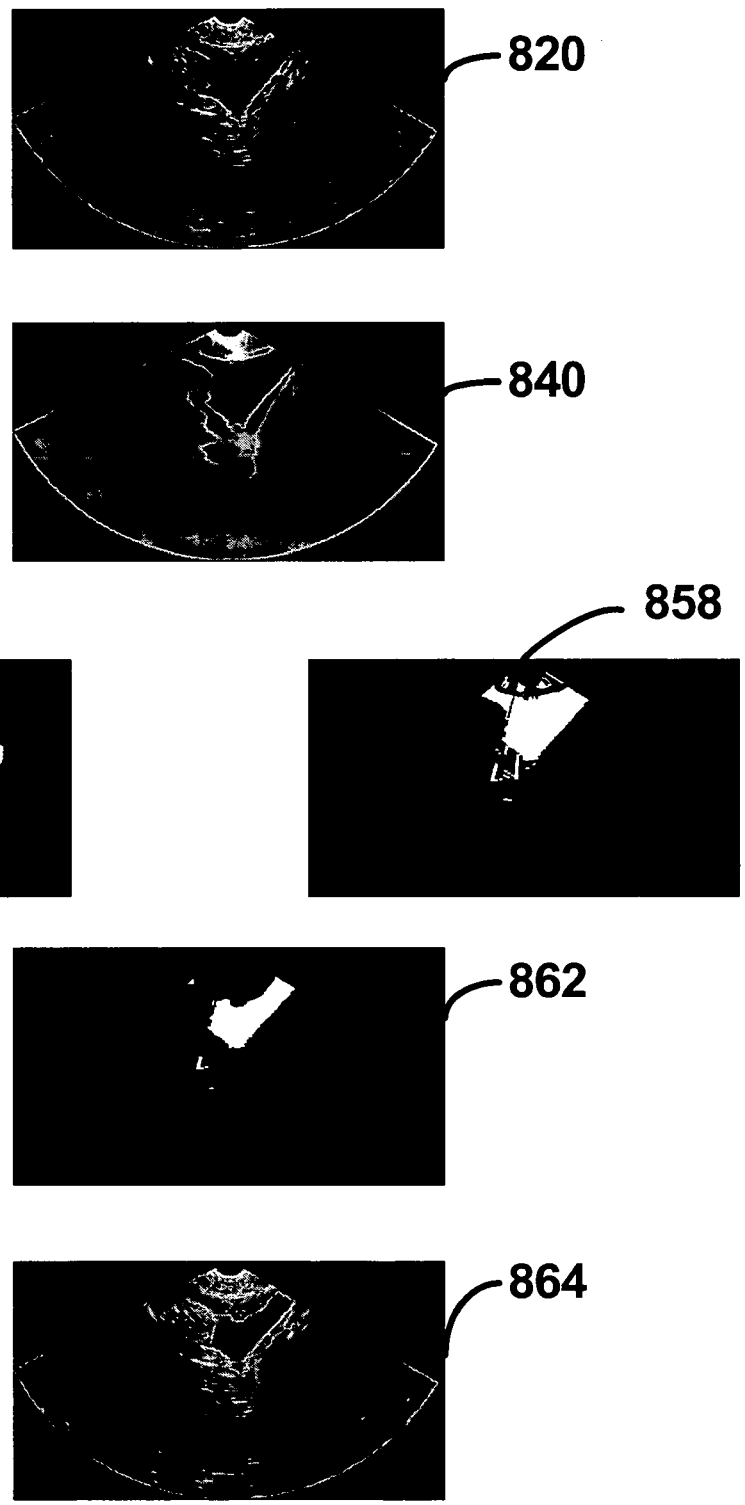
FIG. 10 shows results of sequentially applying the algorithm steps on a sample image.

FIG. 10 shows the results of sequentially applying the algorithm steps of FIGS. 7 and 8A-D on an unprocessed sample image 820 presented within the confines of a scanplane substantially equivalent to the scanplane 210. The results of applying the heat filter 514 and shock filter 518 in enhancing the unprocessed sample is shown in enhanced image 840. The result of intensity-based segmentation algorithms 522 is shown in image 850. The results of edge-based segmentation 438 algorithm using sub-algorithms 526, 530, 534 and 538 of the enhanced image 840 is shown in segmented image 858. The result of the combination 442 utilizing the Boolean AND images 442 algorithm is shown in image 862 where white represents the amniotic fluid area. The result of applying the polishing 464 algorithm employing algorithms 542, 546, 550, 554, 560, and 564 is shown in image 864, which depicts the amniotic fluid area overlaid on the unprocessed sample image 810.

Figure 11:
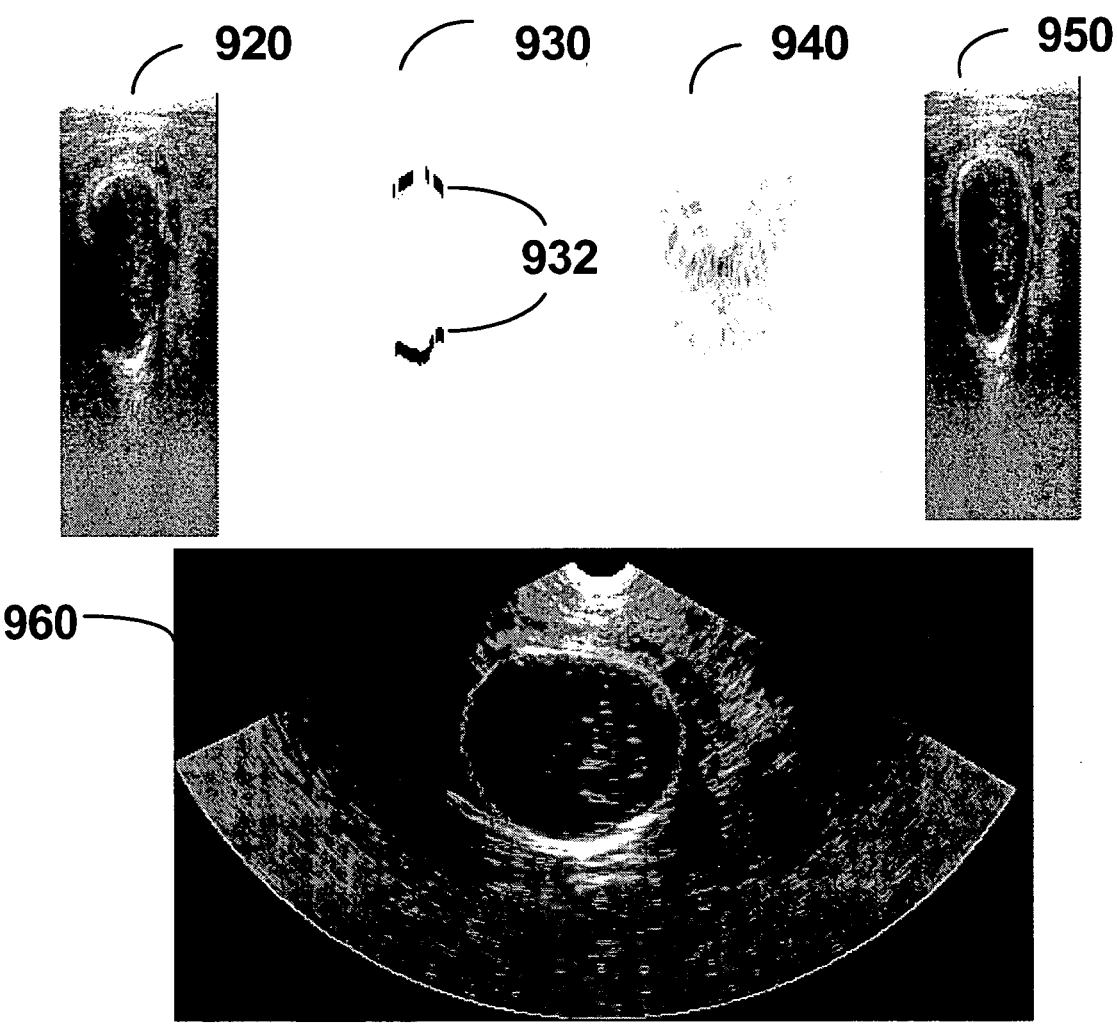
FIG. 11 illustrates a set of intermediate images of the fetal head detection process.

FIG. 11 depicts a series of images showing the results of the above method to automatically detect, locate, and measure the area and volume of a fetal head using the algorithms outlined in FIGS. 7 and 8A-F. Beginning with an input image in polar coordinate form 920, the fetal head image is marked by distinctive bright echoes from the anterior and posterior walls of the fetal skull and a circular shape of the fetal head in the Cartesian image. The fetal head detection algorithm 734 operates on the polar coordinate data (i.e., pre-scan version, not yet converted to Cartesian coordinates).

An example output of applying the head edge detection 734 algorithm to detect potential head edges is shown in image 930. Occupying the space between the anterior and posterior walls are dilated black pixels 932 (stacks or short lines of black pixels representing thick edges). An example of the polar Hough transform 738 for one actual data sample for a specific radius is shown in polar coordinate image 940.

An example of the best-fit circle on real data polar data is shown in polar coordinate image 950 that has undergone the find maximum Hough value step 742. The polar coordinate image 950 is scan-converted to a Cartesian data in image 960 where the effects of finding maximum Hough value 742 algorithm are seen in Cartesian format.

Figure 12:
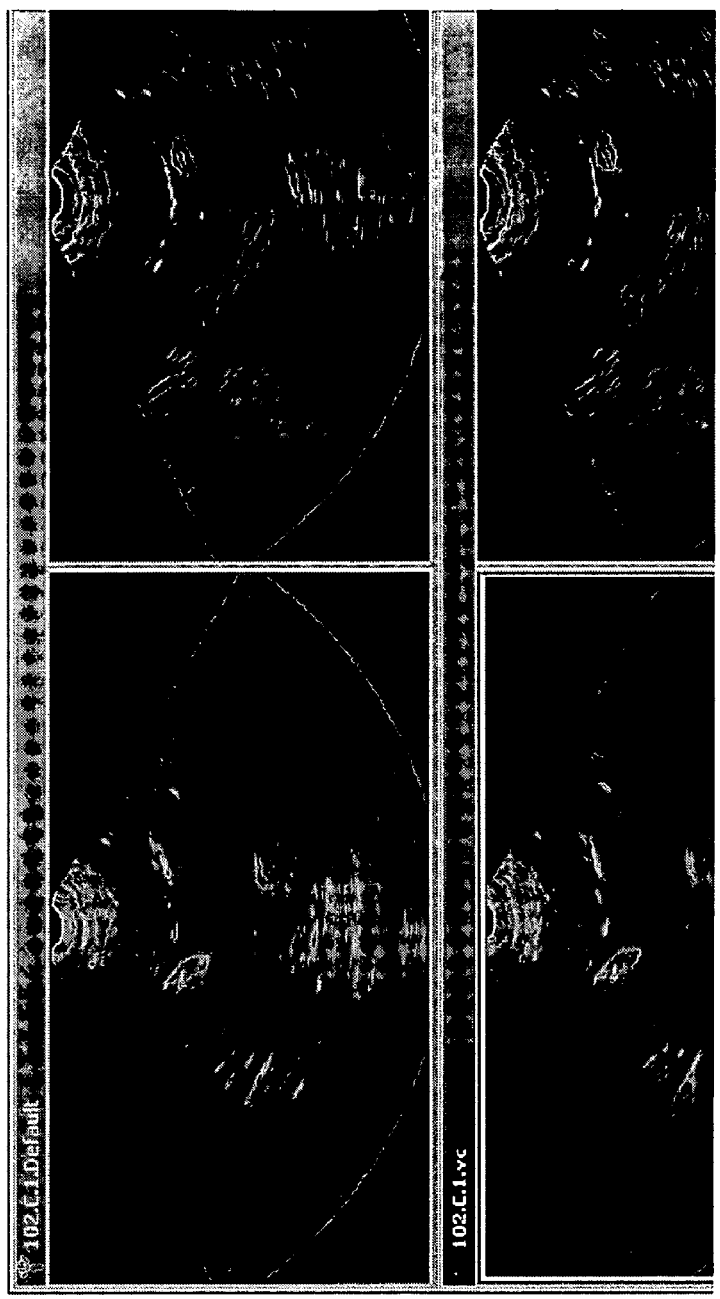
FIG. 12 presents a 4-panel series of sonographer amniotic fluid pocket outlines and the algorithm output amniotic fluid pocket outlines.

FIG. 12 presents a 4-panel series of sonographer amniotic fluid pocket outlines compared to the algorithm's output in a scanplane equivalent to scanplane 210. The top two panels depict the sonographer's outlines of amniotic fluid pockets obtained by manual interactions with the display while the bottom two panels show the resulting amniotic fluid boundaries obtained from the instant invention's automatic application of 2D algorithms, 3D algorithms, combination heat and shock filter algorithms, and segmentation algorithms.

After the contours on all the images have been delineated, the volume of the segmented structure is computed. Two specific techniques for doing so are disclosed in detail in U.S. Pat. No. 5,235,985 to McMorrow et al, herein incorporated by reference. This patent provides detailed explanations for non-invasively transmitting, receiving and processing ultrasound for calculating volumes of anatomical structures.

Multiple Image Cone Acquisition and Image Processing Procedures:

In some embodiments, multiple cones of data acquired at multiple anatomical sampling sites may be advantageous. For example, in some instances, the pregnant uterus may be too large to completely fit in one cone of data sampled from a single measurement or anatomical site of the patient (patient location). That is, the transceiver 10 is moved to different anatomical locations of the patient to obtain different 3D views of the uterus from each measurement or transceiver location.

Obtaining multiple 3D views may be especially needed during the third trimester of pregnancy, or when twins or triplets are involved. In such cases, multiple data cones can be sampled from different anatomical sites at known intervals and then combined into a composite image mosaic to present a large uterus in one, continuous image. In order to make a composite image mosaic that is anatomically accurate without duplicating the anatomical regions mutually viewed by adjacent data cones, ordinarily it is advantageous to obtain images from adjacent data cones and then register and subsequently fuse them together. In a preferred embodiment, to acquire and process multiple 3D data sets or images cones, at least two 3D image cones are generally preferred, with one image cone defined as fixed, and the other image cone defined as moving.

The 3D image cones obtained from each anatomical site may be in the form of 3D arrays of 2D scanplanes, similar to the 3D array 240. Furthermore, the 3D image cone may be in the form of a wedge or a translational array of 2D scanplanes. Alternatively, the 3D image cone obtained from each anatomical site may be a 3D scancone of 3D-distributed scanlines, similar to the scancone 300.

The term "registration" with reference to digital images means the determination of a geometrical transformation or mapping that aligns viewpoint pixels or voxels from one data cone sample of the object (in this embodiment, the uterus) with viewpoint pixels or voxels from another data cone sampled at a different location from the object. That is, registration involves mathematically determining and converting the coordinates of common regions of an object from one viewpoint to the coordinates of another viewpoint. After registration of at least two data cones to a common coordinate system, the registered data cone images are then fused together by combining the two registered data images by producing a reoriented version from the view of one of the registered data cones. That is, for example, a second data cone's view is merged into a first data cone's view by translating and rotating the pixels of the second data cone's pixels that are common with the pixels of the first data cone. Knowing how much to translate and rotate the second data cone's common pixels or voxels allows the pixels or voxels in common between both data cones to be superimposed into approximately the same x, y, z, spatial coordinates so as to accurately portray the object being imaged. The more precise and accurate the pixel or voxel rotation and translation, the more precise and accurate is the common pixel or voxel superimposition or overlap between adjacent image cones. The precise and accurate overlap between the images assures the construction of an anatomically correct composite image mosaic substantially devoid of duplicated anatomical regions.

To obtain the precise and accurate overlap of common pixels or voxels between the adjacent data cones, it is advantageous to utilize a geometrical transformation that substantially preserves most or all distances regarding line straightness, surface planarity, and angles between the lines as defined by the image pixels or voxels. That is, the preferred geometrical transformation that fosters obtaining an anatomically accurate mosaic image is a rigid transformation that doesn't permit the distortion or deforming of the geometrical parameters or coordinates between the pixels or voxels common to both image cones.

The preferred rigid transformation first converts the polar coordinate scanplanes from adjacent image cones into in x, y, z Cartesian axes. After converting the scanplanes into the Cartesian system, a rigid transformation, T, is determined from the scanplanes of adjacent image cones having pixels in common. The transformation T is a combination of a three-dimensional translation vector expressed in Cartesian as $t=(T_x, T_y, T_z)$, and a three-dimensional rotation R matrix expressed as a function of Euler angles $\theta_x$, $\theta_y$, $\theta_z$ around the x, y, and z axes. The transformation represents a shift and rotation conversion factor that aligns and overlaps common pixels from the scanplanes of the adjacent image cones.

In the preferred embodiment of the present invention, the common pixels used for the purposes of establishing registration of three-dimensional images are the boundaries of the amniotic fluid regions as determined by the amniotic fluid segmentation algorithm described above.

Figure 13:
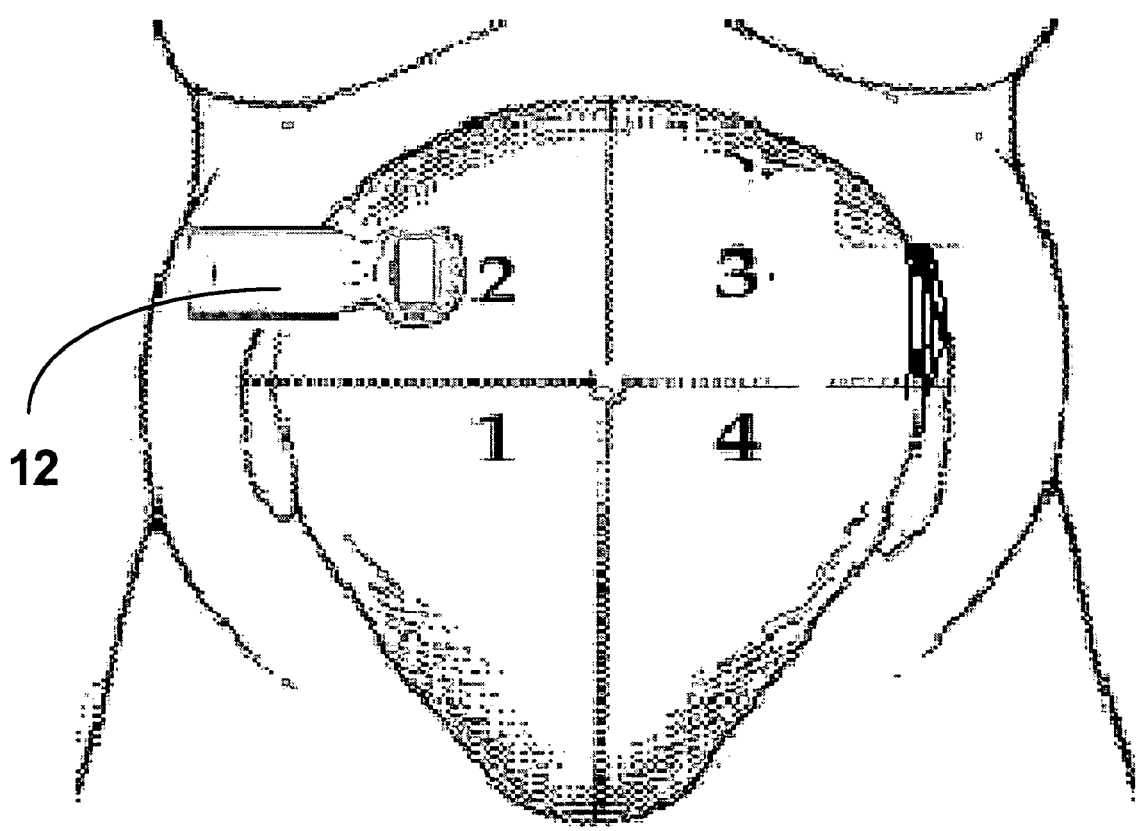
FIG. 13 illustrates a 4-quadrant supine procedure to acquire multiple image cones.
Figure 14:
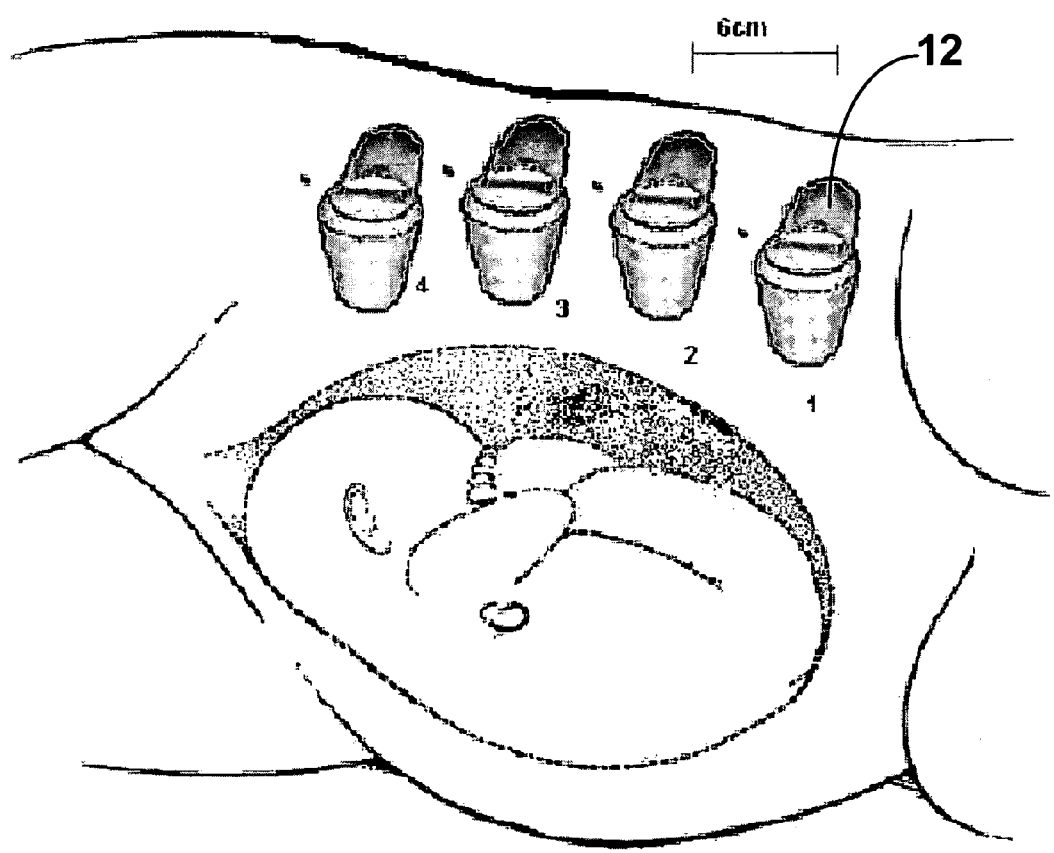
FIG. 14 illustrates an in-line lateral line procedure to acquire multiple image cones.

Several different protocols may be used to collect and process multiple cones of data from more than one measurement site are described in FIGS. 13-14.

FIG. 13 illustrates a 4-quadrant supine procedure to acquire multiple image cones around the center point of uterine quadrants of a patient in a supine procedure. Here the patient lies supine (on her back) displacing most or all of the amniotic fluid towards the top. The uterus is divided into 4 quadrants defined by the umbilicus (the navel) and the lineanigra (the vertical center line of the abdomen) and a single 3D scan is acquired at each quadrant. The 4-quadrant supine protocol acquires four different 3D scans in a two dimensional grid, each corner of the grid being a quadrant midpoint. Four cones of data are acquired by the transceiver 10 along the midpoints of quadrant 1, quadrant 2, quadrant 3, and quadrant 4. Thus, one 3D data cone per uterine quadrant midpoint is acquired such that each quadrant midpoint is mutually substantially equally spaced from each other in a four-corner grid array.

FIG. 14 illustrates a multiple lateral line procedure to acquire multiple image cones in a linear array. Here the patent lies laterally (on her side), displacing most or all of the amniotic fluid towards the top. Four 3D images cones of data are acquired along a line of substantially equally space intervals. As illustrated, the transceiver 10 moves along the lateral line at position 1, position 2, position 3, and position 4. As illustrated in FIG. 14, the inter-position distance or interval is approximately 6 cm.

The preferred embodiment for making a composite image mosaic involves obtaining four multiple image cones where the transceiver 10 is placed at four measurement sites over the patient in a supine or lateral position such that at least a portion of the uterus is ultrasonically viewable at each measurement site. The first measurement site is originally defined as fixed, and the second site is defined as moving and placed at a first known inter-site distance relative to the first site. The second site images are registered and fused to the first site images After fusing the second site images to the first site images, the third measurement site is defined as moving and placed at a second known inter-site distance relative to the fused second site now defined as fixed. The third site images are registered and fused to the second site images Similarly, after fusing the third site images to the second site images, the fourth measurement site is defined as moving and placed at a third known inter-site distance relative to the fused third site now defined as fixed. The fourth site images are registered and fused to the third site images The four measurement sites may be along a line or in an array. The array may include rectangles, squares, diamond patterns, or other shapes. Preferably, the patient is positioned such that the baby moves downward with gravity in the uterus and displaces the amniotic fluid upwards toward the measuring positions of the transceiver 10.

The interval or distance between each measurement site is approximately equal, or may be unequal. For example in the lateral protocol, the second site is spaced approximately 6 cm from the first site, the third site is spaced approximately 6 cm from the second site, and the fourth site is spaced approximately 6 cm from the third site. The spacing for unequal intervals could be, for example, the second site is spaced approximately 4 cm from the first site, the third site is spaced approximately 8 cm from the second site, and the third is spaced approximately 6 cm from the third site. The interval distance between measurement sites may be varied as long as there are mutually viewable regions of portions of the uterus between adjacent measurement sites.

For uteruses not as large as requiring four measurement sites, two and three measurement sites may be sufficient for making a composite 3D image mosaic. For three measurement sites, a triangular array is possible, with equal or unequal intervals. Furthermore, is the case when the second and third measurement sites have mutually viewable regions from the first measurement site, the second interval may be measured from the first measurement site instead of measuring from the second measurement site.

For very large uteruses not fully captured by four measurement or anatomical sites, greater than four measurement sites may be used to make a composite 3D image mosaic provided that each measurement site is ultrasonically viewable for at least a portion of the uterus. For five measurement sites, a pentagon array is possible, with equal or unequal intervals. Similarly, for six measurement sites, a hexagon array is possible, with equal or unequal intervals between each measurement site. Other polygonal arrays are possible with increasing numbers of measurement sites.

The geometrical relationship between each image cone must be ascertained so that overlapping regions can be identified between any two image cones to permit the combining of adjacent neighboring cones so that a single 3D mosaic composite image is produced from the 4-quadrant or in-line laterally acquired images.

The translational and rotational adjustments of each moving cone to conform with the voxels common to the stationary image cone is guided by an inputted initial transform that has the expected translational and rotational values. The distance separating the transceiver 10 between image cone acquisitions predicts the expected translational and rotational values. For example, as shown in FIG. 14, if 6 cm separates the image cones, then the expected translational and rotational values are proportionally estimated. For example, the $(T_x, T_y, T_z)$ and $(\theta_x, \theta_y, \theta_z)$ Cartesian and Euler angle terms fixed images p voxel values are defined respectively as (6 cm, 0 cm, 0 cm) and (0 deg, 0 deg, 0 deg).

Figure 15:
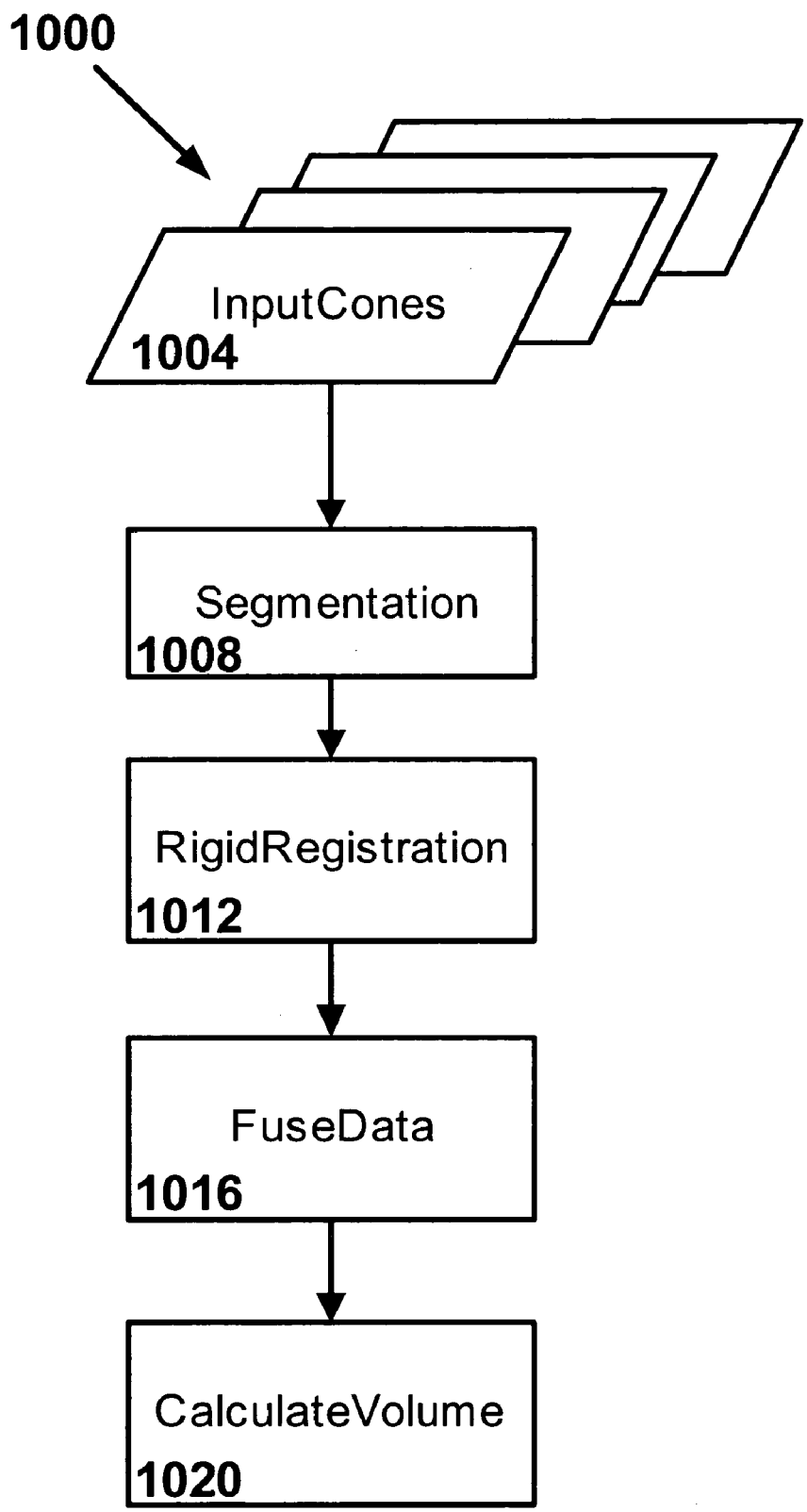
FIG. 15 is a block diagram overview of the rigid registration and correcting algorithms used in processing multiple image cone data sets.

FIG. 15 is a block diagram algorithm overview of the registration and correcting algorithms used in processing multiple image cone data sets. The algorithm overview 1000 shows how the entire amniotic fluid volume measurement process occurs from the multiply acquired image cones. First, each of the input cones 1004 is segmented 1008 to detect all amniotic fluid regions. The segmentation 1008 step is substantially similar to steps 418-480 of FIG. 7. Next, these segmented regions are used to align (register) the different cones into one common coordinate system using a Rigid Registration 1012 algorithm. Next, the registered datasets from each image cone are fused with each other using a Fuse Data 1016 algorithm to produce a composite 3D mosaic image. Thereafter, the total amniotic fluid volume is computed 1020 from the fused or composite 3D mosaic image.

Figure 16:
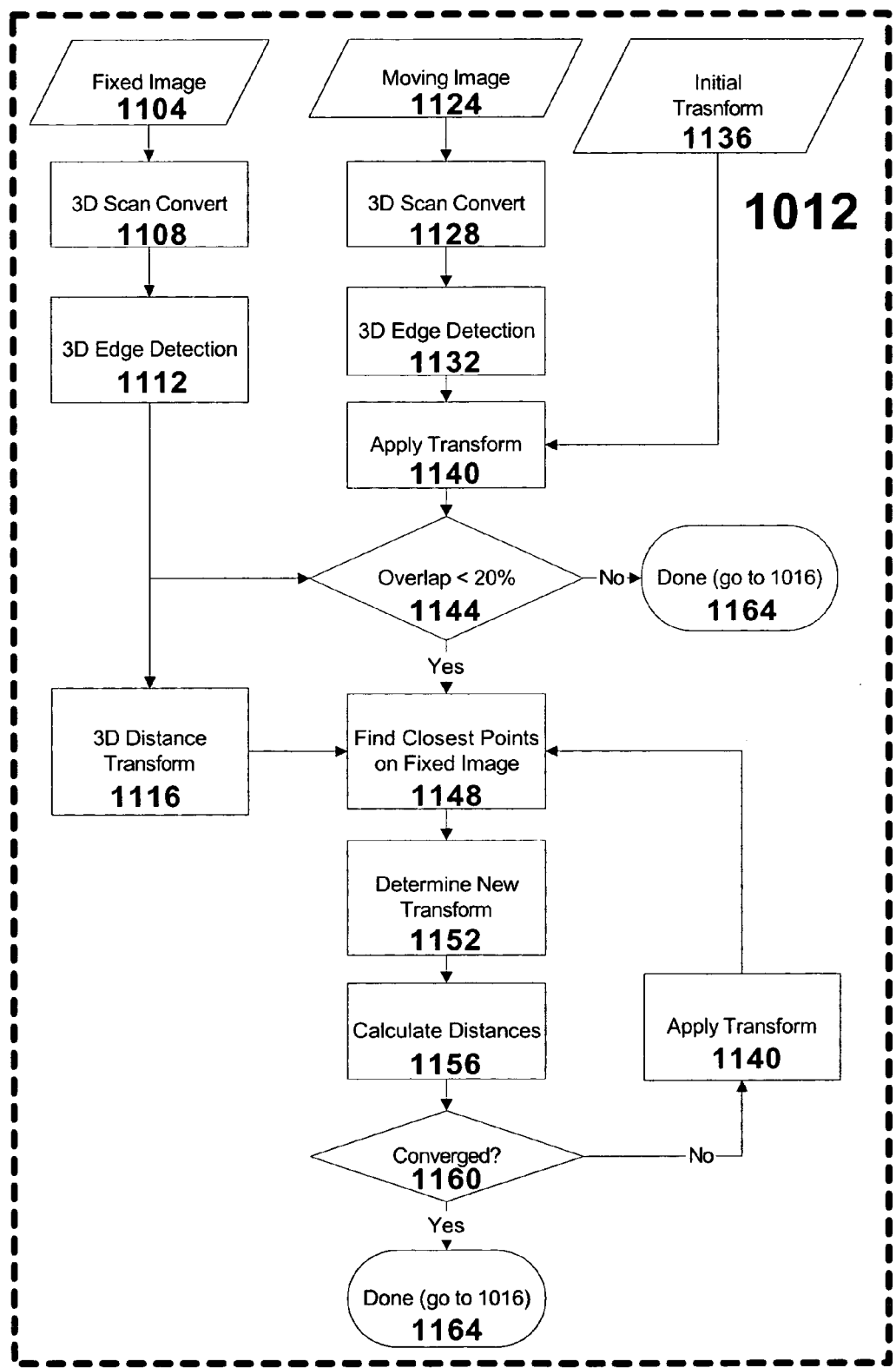
FIG. 16 is a block diagram of the steps in the rigid registration algorithm.

FIG. 16 is a block diagram of the steps of the rigid registration algorithm 1012. The rigid algorithm 1012 is a 3D image registration algorithm and is a modification of the Iterated Closest Point (ICP) algorithm published by P J Besl and N D McKay, in "A Method for Registration of 3-D Shapes," *IEEE Trans. Pattern Analysis & Machine Intelligence*, vol. 14, no. 2, February 1992, pp. 239-256. The steps of the rigid registration algorithm 1012 serves to correct for overlap between adjacent 3D scan cones acquired in either the 4-quadrant supine grid procedure or lateral line multi data cone acquisition procedures. The rigid algorithm 1012 first processes the fixed image 1104 in polar coordinate terms to Cartesian coordinate terms using the 3D Scan Convert 1108 algorithm. Separately, the moving image 1124 is also converted to Cartesian coordinates using the 3D Scan Convert 1128 algorithm. Next, the edges of the amniotic fluid regions on the fixed and moving images are determined and converted into point sets p and q respectively by a 3D edge detection process 1112 and 1132. Also, the fixed image point set, p, undergoes a 3D distance transform process 1116 which maps every voxel in a 3D image to a number representing the distance to the closest edge point in p. Pre-computing this distance transform makes subsequent distance calculations and closest point determinations very efficient.

Next, the known initial transform 1136, for example, (6, 0, 0) for the Cartesian $T_x$, $T_y$, $T_z$ terms and (0, 0, 0) for the $\theta_x$, $\theta_y$, $\theta_z$ Euler angle terms for an inter-transceiver interval of 6 cm, is subsequently applied to the moving image by the Apply Transform 1140 step. This transformed image is then compared to the fixed image to examine for the quantitative occurrence of overlapping voxels. If the overlap is less than 20%, there are not enough common voxels available for registration and the initial transform is considered sufficient for fusing at step 1016.

If the overlapping voxel sets by the initial transform exceed 20% of the fixed image p voxel sets, the q-voxels of the initial transform are subjected to an iterative sequence of rigid registration.

A transformation T serves to register a first voxel point set p from the first image cone by merging or overlapping a second voxel point set q from a second image cone that is common to p of the first image cone. A point in the first voxel point set p may be defined as $p_i=(x_i,y_i,z_i)$ and a point in the second voxel point set q may similarly be defined as $q_j=(x_j,y_j,z_j)$, If the first image cone is considered to be a fixed landmark, then the T factor is applied to align (translate and rotate) the moving voxel point set q onto the fixed voxel point set p.

The precision of T is often affected by noise in the images that accordingly affects the precision of t and R, and so the variability of each voxel point set will in turn affect the overall variability of each matrix equation set for each point. The composite variability between the fixed voxel point set p and a corresponding moving voxel point set q is defined to have a cross-covariance matrix $C_{pq}$, more fully described in equation E8 as:

$$C_{pq} = \frac{1}{n}\sum_{i=1...n}(p_i - \bar{p})(q_i - \bar{q})^T \qquad E8$$

where, n is the number of points in each point set and $\bar{p}$ and $\bar{q}$ are the central points in the two voxel point sets. How strong the correlation is between two sets data is determined by statistically analyzing the cross-covariance $C_{pq}$. The preferred embodiment uses a statistical process known as the Single Value Decomposition (SVD) originally developed by Eckart and Young (G. Eckart and G. Young, 1936, *The Approximation of One Matrix by Another of Lower Rank*, Pychometrika 1, 211-218). When numerical data is organized into matrix form, the SVD is applied to the matrix, and the resulting SVD values are determined to solve for the best fitting rotation transform R to be applied to the moving voxel point set q to align with the fixed voxel point set p to acquire optimum overlapping accuracy of the pixel or voxels common to the fixed and moving images.

Equation E9 gives the SVD value of the cross-covariance $C_{pq}$:

$$C_{pq}=UDV^t \qquad E9$$

where D is a 3×3 diagonal matrix and U and V are orthogonal 3×3 matrices

Equation E10 further defines the rotational R description of the transformation T in terms of U and V orthogonal 3×3 matrices as:

$$R=UV^T \qquad E10$$

Equation E11 further defines the translation transform t description of the transformation T in terms of $\bar{p},\bar{q}$ and R as:

$$t=\bar{p}-R\bar{q} \qquad E11$$

Equations E8 through E11 present a method to determine the rigid transformation between two point sets p and q—this process corresponds to step 1152 in FIG. 17.

The steps of the registration algorithm are applied iteratively until convergence. The iterative sequence includes a Find Closest Points on Fixed Image 1148 step, a Determine New Transform 1152 step, a Calculate Distances 1156 step, and Converged decision 1160 step.

In the Find Closest Points on Fixed Image 1148 step, corresponding q points are found for each point in the fixed set p. Correspondence is defined by determining the closest edge point on q to the edge point of p. The distance transform image helps locate these closest points. Once p and closest −q pixels are identified, the Determine New Transform 1152 step calculates the rotation R via SVD analysis using equations E8-E10 and translation transform t via equation E11. If, at decision step 1160, the change in the average closest point distance between two iterations is less than 5%, then the predicted-q pixel candidates are considered converged and suitable for receiving the transforms R and t to rigidly register the moving image Transform 1136 onto the common voxels p of the 3D Scan Converted 1108 image. At this point, the rigid registration process is complete as closest proximity between voxel or pixel sets has occurred between the fixed and moving images, and the process continues with fusion at step 1016.

If, however, there is >5% change between the predicted-q pixels and p pixels, another iteration cycle is applied via the Apply Transform 1140 to the Find Closest Points on Fixed Image 1148 step, and is cycled through the converged 1160 decision block. Usually in 3 cycles, though as many as 20 iterative cycles, are engaged until is the transformation T is considered converged.

Figure 17A:
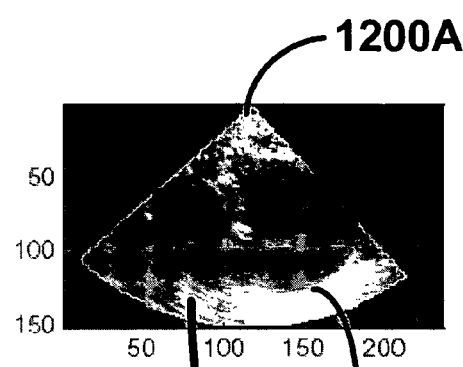
FIG. 17A is an example image showing a first view of a fixed scanplane.
Figure 17B:
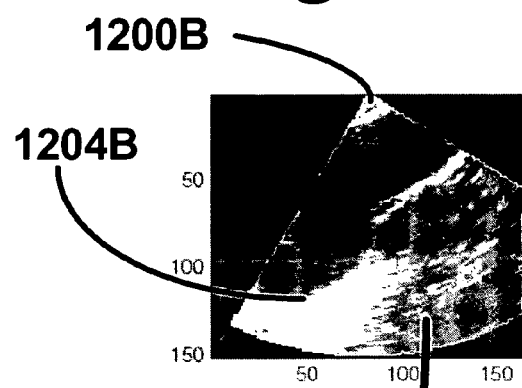
FIG. 17B is an example image showing a second view view of a moving scanplane having some voxels in common with the first scanplane.
Figure 17C:
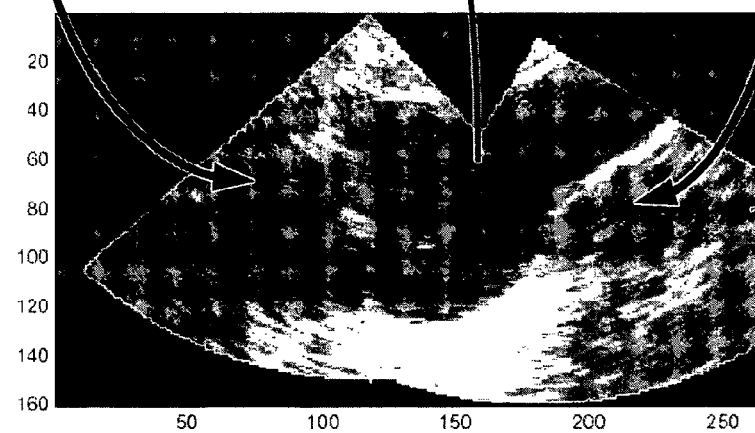
FIG. 17C is a composite image of the first (fixed) and second (moving) images.

A representative example for the application of the preferred embodiment for the registration and fusion of a moving image onto a fixed image is shown in FIGS. 17A-17C.

FIG. 17A is a first measurement view of a fixed scanplane 1200A from a 3D data set measurement taken at a first site. A first pixel set p consistent for the dark pixels of AFV is shown in a region 1204A. The region 1204A has approximate x-y coordinates of (150, 120) that is closest to dark edge.

FIG. 17B is a second measurement view of a moving scanplane 1200B from a 3D data set measurement taken at a second site. A second pixel set q consistent for the dark pixels of AFV is shown in a region 1204B. The region 1204B has approximate x-y coordinates of (50, 125) that is closest to dark edge.

FIG. 17C is a composite image 1200C of the first (fixed) 1200A and second (moving) 1200B images in which common pixels 1204B at approximate coordinates (50,125) is aligned or overlapped with the voxels 1204A at approximate coordinates (150, 120). That is, the region 1204B pixel set q is linearly and rotational transformed consistent with the closest edge selection methodology as shown in FIGS. 13A and 13B from employing the 3D Edge Detection 1112 step. The composite image 1200C is a mosaic image from scanplanes having approximately the same $\phi$ and rotation $\theta$ angles.

The registration and fusing of common pixel sets p and q from scanplanes having approximately the same $\phi$ and rotation $\theta$ angles can be repeated for other scanplanes in each 3D data set taken at the first (fixed) and second (moving) anatomical sites. For example, if the composite image 1200C above was for scanplane #1, then the process may be repeated for the remaining scanplanes #2-24 or #2-48 or greater as needed to capture a completed uterine mosaic image. Thus an array similar to the 3D array 240 from FIG. 5B is assembled, except this time the scanplane array is made of composite images, each composited image belonging to a scanplane having approximately the same $\phi$ and rotation $\theta$ angles.

If a third and a fourth 3D data sets are taken, the respective registration, fusing, and assembling into scanplane arrays of composited images is undertaken with the same procedures. In this case, the scanplane composite array similar to the 3D array 240 is composed of a greater mosaic number of registered and fused scanplane images.

A representative example the fusing of two moving images onto a fixed image is shown in FIGS. 18A-18D.

Figures 18A, 18B, 18C, 18D:
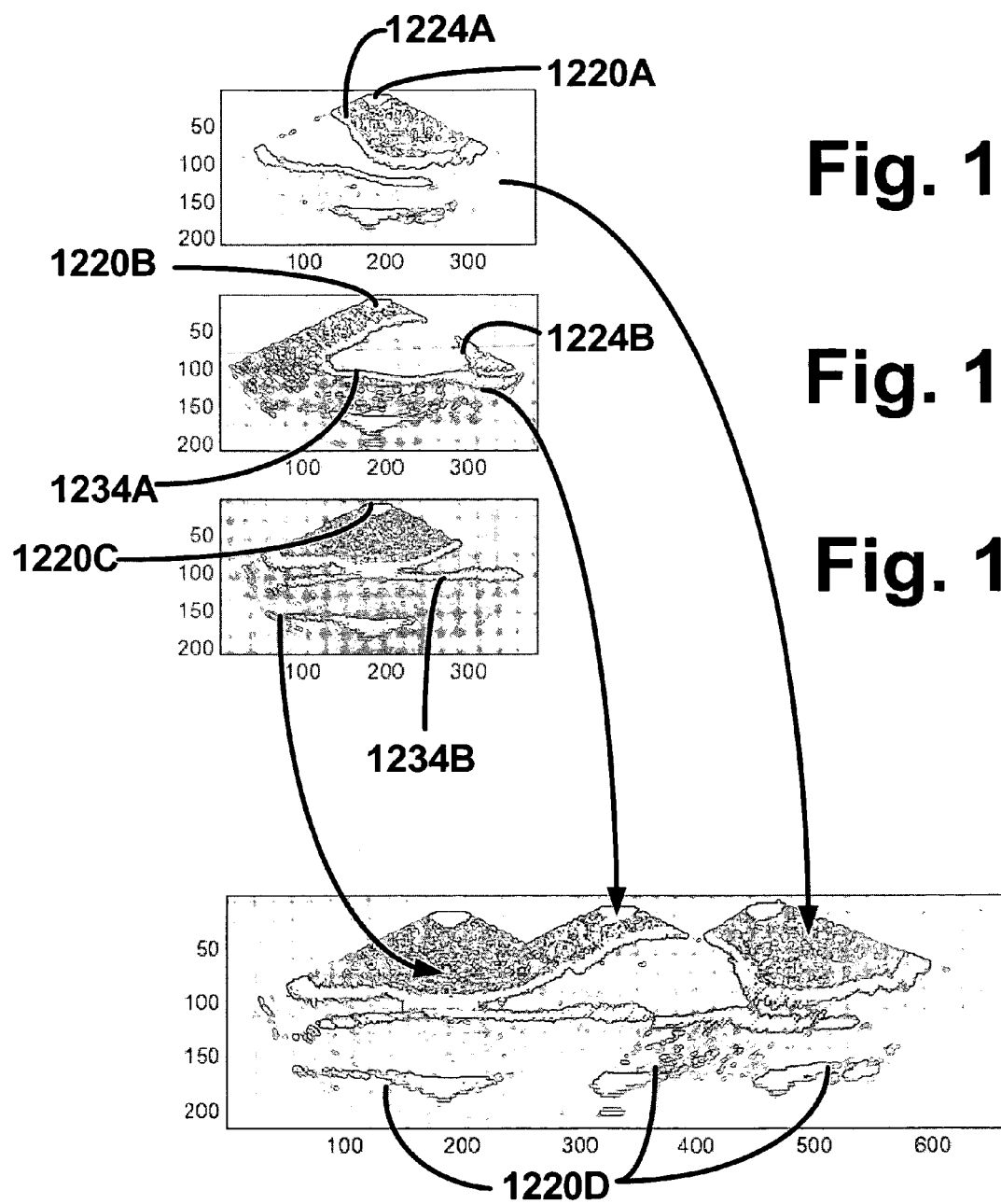
FIG. 18A is an example image showing a first view of a fixed scanplane.
FIG. 18B is an example image showing a second view of a moving scanplane having some voxels in common with the first view and a third view.
FIG. 18C is a third view of a moving scanplane having some voxels in common with the second view.
FIG. 18D is a composite image of the first (fixed), second (moving), and third (moving) views.

FIG. 18A is a first view of a fixed scanplane 1220A. Region 1224A is identified as p voxels approximately at the coordinates (150, 70).

FIG. 18B is a second view of a first moving scanplane 1220B having some q voxels 1224B at x-y coordinates (300, 100) common with the first measurements p voxels at x-y coordinates (150, 70). Another set of voxels 1234A is shown roughly near the intersection of x-y coordinates (200, 125). As the transceiver 10 was moved only translationally, The scanplane 1220B from the second site has approximately the same tilt $\phi$ and rotation $\theta$ angles of the fixed scanplane 1220A taken from the first lateral in-line site.

FIG. 18C is a third view of a moving scanplane 1220C. A region 1234B is identified as q voxels approximately at the x-y coordinates (250, 100) that are common with the second views q voxels 1234A. The scanplane 1220c from the third lateral in-line site has approximately the same tilt $\phi$ and rotation $\theta$ angles of the fixed scanplane 1220A taken from the first lateral in-line site and the first moving scanplane 1220B taken from the second lateral in-line site.

FIG. 18D is a composite mosaic image 1220D of the first (fixed) 1220A image, the second (moving) 1220B image, and the third (moving) 1220C image representing the sequential alignment and fusing of q voxel sets 1224B to 1224A, and 1234B with 1234A.

A fourth image similarly could be made to bring about a 4-image mosaic from scanplanes from a fourth 3D data set acquired from the transceiver 10 taking measurements at a fourth anatomical site where the fourth 3D data set is acquired with approximately the same tilt $\phi$ and rotation $\theta$ angles.

The transceiver 10 is moved to different anatomical sites to collect 3D data sets by hand placement by an operator. Such hand placement could create the acquiring of 3D data sets under conditions in which the tilt $\phi$ and rotation $\theta$ angles are not approximately equal, but differ enough to cause some measurement error requiring correction to use the rigid registration 1012 algorithm. In the event where the 3D data sets between anatomical sites, either between a moving supine site in relation to its beginning fixed site, or between a moving lateral site with its beginning fixed site, cannot be acquired with the tilt $\phi$ and rotation $\theta$ angles being approximately the same, then the built-in accelerometer measures the changes in tilt $\phi$ and rotation $\theta$ angles and compensates accordingly so that acquired moving images are presented if though they were acquired under approximately equal tilt $\phi$ and rotation $\theta$ angle conditions.

Figure 19:
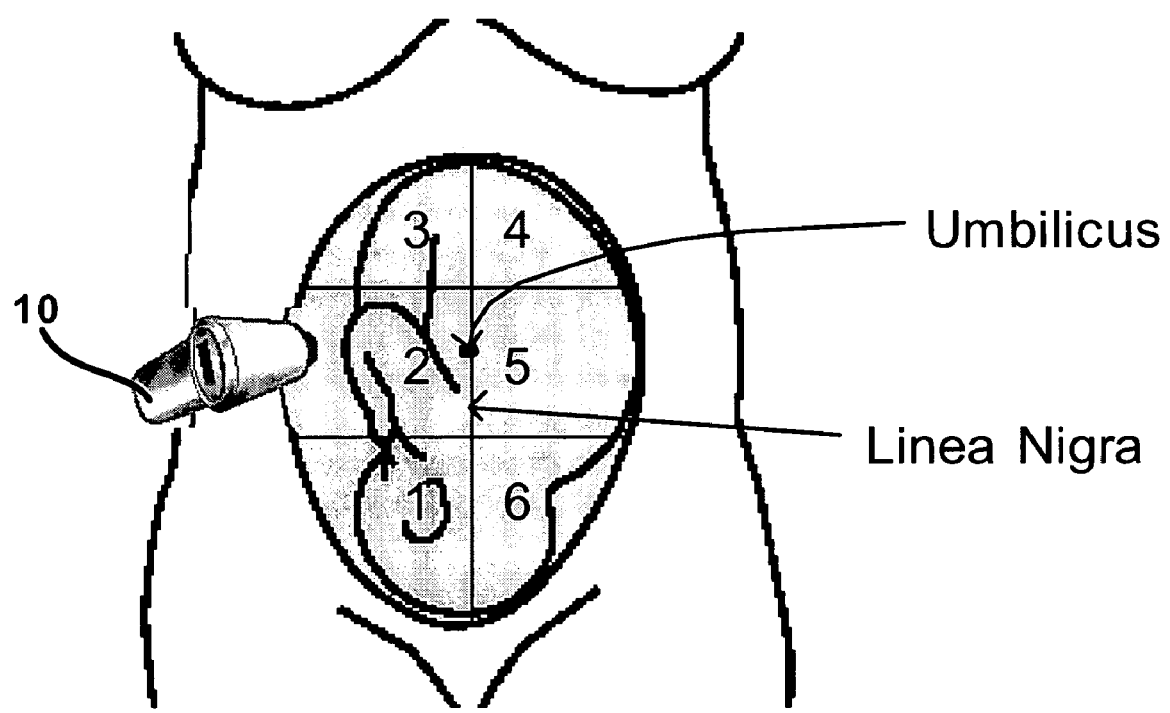
FIG. 19 illustrates a 6-section supine procedure to acquire multiple image cones around the center point of uterus of a patient in a supine procedure.

FIG. 19 illustrates a 6-section supine procedure to acquire multiple image cones around the center point of a uterus of a patient in a supine position. Each of the 6 segments are scanned in the order indicated, starting with segment 1 on the lower right side of the patient. The display on the scanner 10 is configured to indicate how many segments have been scanned, so that the display shows "0 of 6," "1 of 6," ... "6 of 6." The scans are positioned such that the lateral distances between each scanning position (except between positions 3 and 4) are approximately about 8 cm.

To repeat the scan, the top button of the scanner 10 is repetitively depressed, so that it returns the scan to "0 of 6," to permit a user to repeat all six scans again. Finally, the scanner 10 is returned to the cradle to upload the raw ultrasound data to computer, intranet, or Internet as depicted in FIGS. 2C, 3, and 4 for algorithmic processing, as will be described in detail below. Within a predetermined time period, a result is generated that includes an estimate of the amniotic fluid volume.

As with the quadrant and the four in-line scancone measuring methods described earlier, the six-segment procedure ensures that the measurement process detects all amniotic fluid regions. The transceiver 10 projects outgoing ultrasound signals, in this case into the uterine region of a patient, at six anatomical locations, and receives incoming echoes reflected back from the regions of interest to the transceiver 10 positioned at a given anatomical location. An array of scanplane images are obtained for each anatomical location based upon the incoming echo signals. Image enhanced and segmented regions for the scanplane images are determined for each scanplane array, which may be a rotational, wedge, or translationally configured scanplane array. The segmented regions are used to align or register the different scancones into one common coordinate system. Thereafter, the registered datasets are merged with each other so that the total amniotic fluid volume is computed from the resulting fused image.

Figure 20:
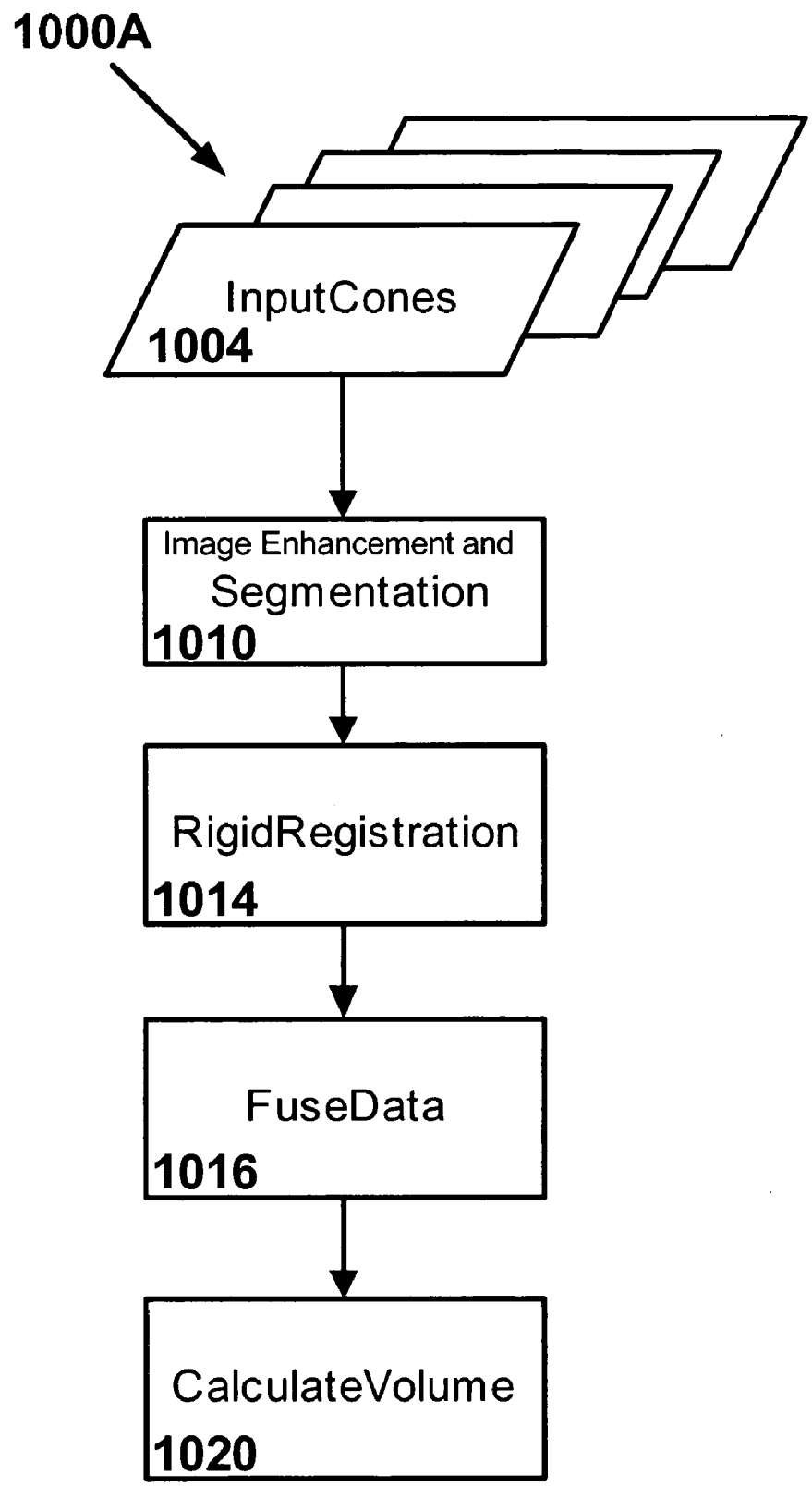
FIG. 20 is a block diagram algorithm overview of the registration and correcting algorithms used in processing the 6-section multiple image cone data sets depicted in FIG. 19.

FIG. 20 is a block diagrammatic overview of an algorithm for the registration and correction processing of the 6-section multiple image cone data sets depicted in FIG. 19. A six-section algorithm overview 1000A includes many of the same blocks of algorithm overview 1000 depicted in FIG. 15. However, the segmentation registration procedures are modified for the 6-section multiple image cones. In the algorithm overview 1000A, the subprocesses include the InputCones block 1004, an Image Enhancement and Segmentation block 1010, a RigidRegistration block 1014, the FuseData block 1016, and the Calculate Volume block 1020. Generally, the Image Enhanced and Segmentation block 1010 reduces the effects of noise, which may include speckle noise, in the data while preserving the salient edges on the image. The enhanced images are then segmented by an edge-based and intensity-based method, and the results of each segmentation method are then subsequently combined. The results of the combined segmentation method are then cleaned up to fill gaps and to remove outliers. The area and/or the volume of the segmented regions is then computed.

Figure 21:
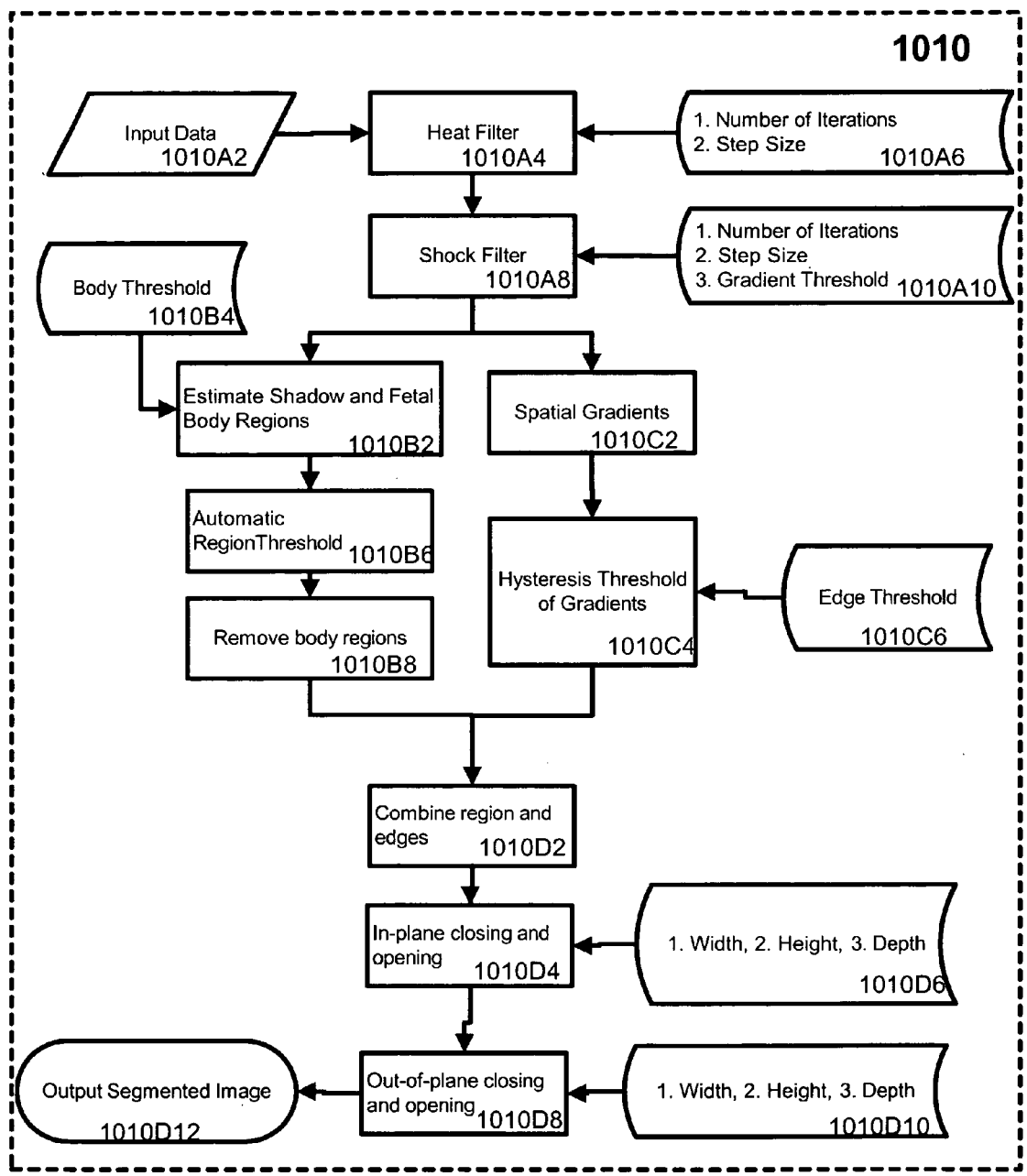
FIG. 21 is an expansion of the Image Enhancement and Segmentation block 1010 of FIG. 20.

FIG. 21 is a more detailed view of the Image Enhancement and Segmentation block 1010 of FIG. 20. Very similar to the algorithm processes of Image Enhancement 418, Intensity-based segmentation 422, and Edge-based segmentation 438 explained for FIG. 7, the enhancement-segmentation block 1010 begins with an input data block 1010A2, wherein the signals of pixel image data are subjected to a blurring and speckle removal process followed by a sharpening or deblurring process. The combination of blurring and speckle removal followed by sharpening or deblurring enhances the appearance of the pixel-based input image.

Figure 23:
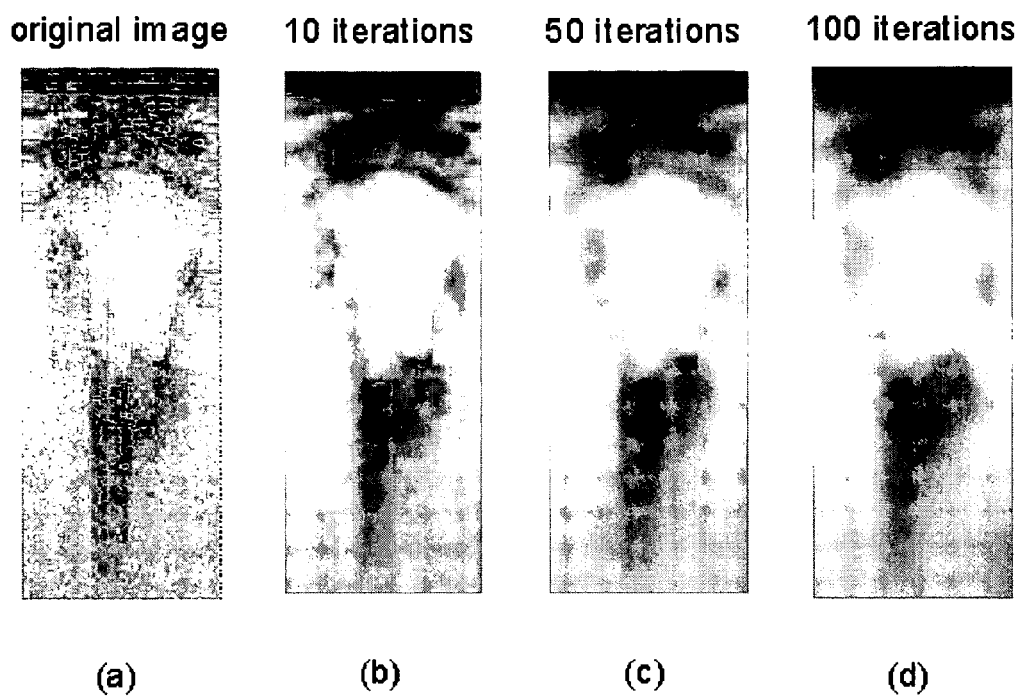
FIG. 23 is a 4-panel image set that shows the effect of multiple iterations of the heat filter applied to an original image.

The blurring and deblurring is achieved by a combination of heat and shock filters. The inputed pixel related data from process 1010A2 is first subjected to a heat filter process block 1010A4. The heat filter block 1010A4 is a Laplacian-based filtering and results in reduction of the speckle noise and smooths or otherwise blurs the edges in the image. The heat filter block 1010A4 is modified via a user-determined stored data block 1010A6 wherein the number of heat filter iterations and step sizes are defined by the user and are applied to the inputed data 1010A2 in the heat filter process block 1010A4. The effect of heat iteration number in progressively blurring and removing speckle from an original image as the number of iteration cycles is increased is shown in FIG. 23. Once the pixel image data has been heat filter processed, the pixel image data is further processed by a shock filter block 1010A8. The shock filter block 1010A8 is subjected to a user-determined stored data block 1010A10 wherein the number shock filter iterations, step sizes, and gradient threshold are specified by the user. The foregoing values are then applied to heat filtered pixel data in the shock filter block 1010A8. The effect of shock iteration number, step sizes, and gradient thresholds in reducing the blurring is seen in signal plots (a) and (b) of FIG. 24. Thereafter, a heat and shock-filtered pixel data is parallel processed in two algorithm pathways, as defined by blocks 1010B2-6 (Intensity-Based Segmentation Group) and blocks 1010C2-4 (Edge-Based Segmentation Group).

The Intensity-based Segmentation relies on the observation that amniotic fluid is usually darker than the rest of the image. Pixels associated with fluids are classified based upon a threshold intensity level. Thus pixels below this intensity threshold level are interpreted as fluid, and pixels above this intensity threshold are interpreted as solid or non-fluid tissues. However, pixel values within a dataset can vary widely, so a means to automatically determine a threshold level within a given dataset is required in order to distinguish between fluid and non-fluid pixels. The intensity-based segmentation is divided into three steps. A first step includes estimating the fetal body and shadow regions, a second step includes determining an automatic thresholding for the fluid region after removing the body region, and a third step includes removing the shadow and fetal body regions from the potential fluid regions.

The Intensity-Based Segmentation Group includes a fetal body region block 1010B2, wherein an estimate of the fetal shadow and body regions is obtained. Generally, the fetal body regions in ultrasound images appear bright and are relatively easily detected. Commonly, anterior bright regions typically correspond with the dome reverberation of the transceiver 10, and the darker appearing uterus is easily discerned against the bright pixel regions formed by the more echogenic fetal body that commonly appears posterior to the amniotic fluid region. In fetal body region block 1010B2, the fetal body and shadow is found in scanlines that extend between the bright dome reverberation region and the posterior bright-appearing fetal body. A magnitude of the estimate of fetal and body region is then modified by a user-determined input parameter stored in a body threshold data block 1010B4, and a pixel value is chosen by the user. For example, a pixel value of 40 may be selected by the user. An example of the image obtained from blocks 1010B2-4 is panel (c) of FIG. 25. Once the fetal body regions and the shadow has been estimated, an automatic region threshold block 1010B6 is applied to this estimate to determine which pixels are fluid related and which pixels are non-fluid related. The automatic region threshold block 1010B6 uses a version of the Otsu algorithm (R M Haralick and L G Shaprio, Computer and Robot Vision, vol. 1, Addison Wesley 1992, page 11, incorporated by reference). Briefly, and in general terms, the Otsu algorithm determines a threshold value from an assumed bimodal pixel value histogram that generally corresponds to fluid and some soft tissue (non-fluid) such as placental or other fetal or maternal soft tissue. All pixel values less than the threshold value as determined by the Otsu algorithm are designated as potential fluid pixels. Using the Otsu algorithm determined threshold value, the first pathway is completed by a removing body regions above this threshold value in block 1010B8 so that the amniotic fluid regions are isolated. An example of the effect of the Intensity-based segmentation group is shown in panel (d) of FIG. 25. The isolated amniotic fluid region image thus obtained from the intensity-based segmentation process is then processed for subsequent combination with the end result of the second edge-based segmentation method.

Referring now to the second pathway or the Edge-Based Segmentation Group, the procedural blocks find pixel points on an image having high spatial gradient magnitudes. The edge-based segmentation process begins processing the shock filtered 1010A8 pixel data via a spatial gradients block 1010C2 in which the gradient magnitude of a given pixel neighborhood within the image is determined. The gradient magnitude is determined by the taking the X and Y derivatives using the difference kernels shown in FIG. 26. The gradient magnitude of the image is given by Equation E7:

$$\|\nabla I\| = \sqrt{I_x^2 + I_y^2}$$

$$I_x = I * K_x$$

$$I_y = I * K_y \qquad \text{E7}$$

where * is the convolution operator.

Once the gradient magnitude is determined, pixel edge points are determined by a hysteresis threshold of gradients process block 1010C4. In block 1010C4, a lower and upper threshold value is selected. The image is then thresholded using the lower value and a connected component labeling is carried out on the resulting image. The pixel value of each connected component is measured to determine which pixel edge points have gradient magnitude pixel values equal to or greater than the upper threshold value. Those pixel edge points having gradient magnitude pixel values equal to or exceeding the upper threshold are retained. This retention of pixels having strong gradient values serves to retain selected long connected edges which have one or more high gradient points.

Thereafter, the image is thresholded using the upper value, and a connected component labeling is carried out on the resulting image. The hysteresis threshold 1010C4 is modified by a user-determined edge threshold block 1010C6. An example of an application of the second pathway will be shown in panels (b) for the spatial gradients block 1010C2 and (c) for the threshold of gradients process block 1010C4 of FIG. 27. Another example of application of the edge detection block group for blocks 1010C2 and 1010C4 can also be seen in panel (e) of FIG. 25.

Figure 25:
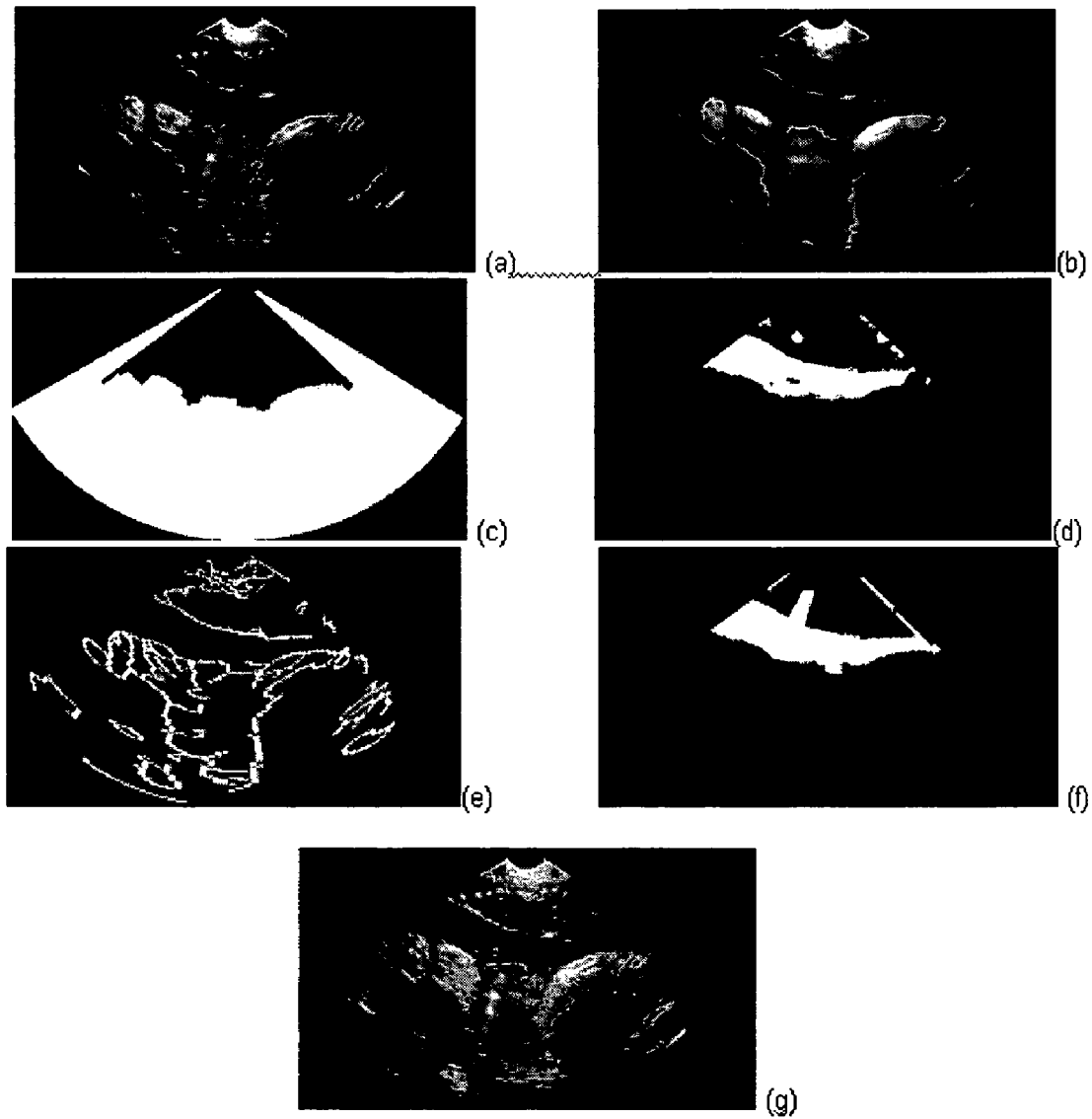
FIG. 25 is a 7-panel image set progressively receiving application of the image enhancement and segmentation algorithms of FIG. 21.

Referring again to FIG. 21, the first and second pathways are merged at a combine region and edges process block 1010D2. The combining process avoids erroneous segmentation arising from either the intensity-based or edge-based segmentation processes. The goal of the combining process is to ensure that good edges are reliably identified so that fluid regions are bounded by strong edges. Intensity-based segmentation may underestimate fluid volume, so that the boundaries need to be corrected using the edge-based segmentation information. In block 1010D2, the beginning and end of each scanline within the segmented region is determined by searching for edge pixels on each scanline. If no edge pixels are found in the search region, the segmentation on that scanline is removed. If edge pixels are found, then the region boundary locations are moved to the location of these edge pixels. Panel (f) of FIG. 25 illustrates the effects of the combining block 1010D2.

The segmentation resulting from the combination of region and edge information occasionally includes extraneous regions or even holes. A cleanup stage helps ensure consistency of segmented regions in a single scanplane and between scanplanes. The cleanup stage uses morphological operators (such as erosion, dilation, opening, closing) using the Markov Random Fields (MRFs) as disclosed in Forbes et al. (Florence Forbes and Adrian E. Raftery, "Bayesian morphology: Fast Unsupervised Bayesian Image Analysis," *Journal of the American Statistical Association*, June 1999, herein incorporated by reference). The combined segmentation images receive the MRFs by being subjected to an In-plane Closing and Opening process block 1010D4. The In-plane opening-closing block 1010D4 block is a morphological operator wherein pixel regions are opened to remove pixel outliers from the segmented region, or that fills in or "closes" gaps and holes in the segmented region within a given scanplane. Block 1010D4 uses a one-dimensional structuring element extending through five scanlines. The closing-opening block is affected by a user-determined width, height, and depth parameter block 1010D6. Thereafter, an Out-of-plane Closing and Opening processing block 1010D8 is applied. The block 1010D8 applies a set of out-of-plane morphological closings and openings using a one-dimensional structuring element extending through three scanlines. Pixel inconsistencies are accordingly removed between the scanplanes. Panel (g) of FIG. 25 illustrates the effects of the blocks 1010D4-8.

Figure 22:
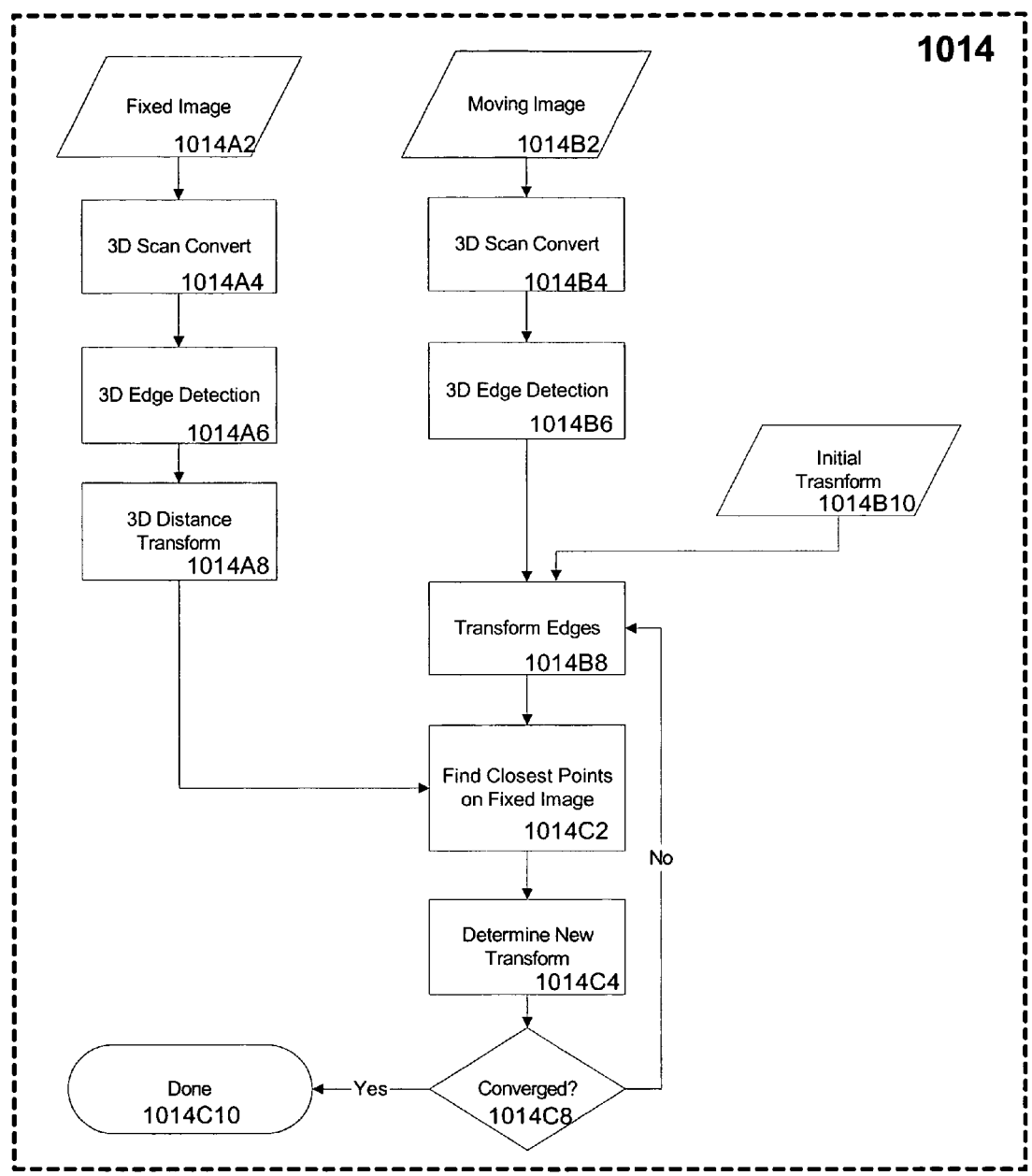
FIG. 22 is an expansion of the RigidRegistration block 1014 of FIG. 20.

FIG. 22 is an expansion of the RigidRegistration block 1014 of FIG. 20. Similar in purpose and general operation using the previously described ICP algorithm as used in the RigidRegistration block 1012 of FIG. 16, the block 1014 begins with parallel inputs of a fixed Image 1014A, a Moving Image 1014B, and an Initial Transform input 1014B10.

The steps of the rigid registration algorithm 1014 correct any overlaps between adjacent 3D scan cones acquired in the 6-section supine grid procedure. The rigid algorithm 1014 first converts the fixed image 1104A2 from polar coordinate terms to Cartesian coordinate terms using the 3D Scan Convert 1014A4 algorithm. Separately, the moving image 1014B2 is also converted to Cartesian coordinates using the 3D Scan Convert 1014B4 algorithm. Next, the edges of the amniotic fluid regions on the fixed and moving images are determined and converted into point sets p and q, respectively by a 3D edge detection process 1014A6 and 1014B6. Also, the fixed image point set, p, undergoes a 3D distance transform process 1014B8 which maps every voxel in a 3D image to a number representing the distance to the closest edge point in p. Pre-computing this distance transform makes subsequent distance calculations and closest point determinations very efficient.

Next, the known initial transform 1014B10, for example, (6, 0, 0) for the Cartesian $T_x$, $T_y$, $T_z$ terms and (0, 0, 0) for the $\theta_x$, $\theta_y$, $\theta_z$ Euler angle terms, for an inter-transceiver interval of 6 cm, is subsequently applied to the moving image by the transform edges 1014B8 block. This transformed image is then subjected to the Find Closest Points on Fixed Image block 1014C2, similar in operation to the block 1148 of FIG. 16. Thereafter, a new transform is determined in block 1014C4, and the new transform is queried for convergence at decision diamond 1014C8. If conversion is attained, the RigidRegistration 1014 is done at terminus 1014C10. Alternatively, if conversion is not attained, then a return to the transform edges block 1014B8 occurs to start another iterative cycle.

The RigidRegistration block 1014 typically converges in less than 20 iterations. After applying the initial transformation, the entire registration process is carried out in case there are any overlapping segmented regions between any two images. Similar to the process described in connection with FIG. 16, an overlap threshold of approximately 20% is currently set as an input parameter.

FIG. 23 is a 4-panel image set that shows the effect of multiple iterations of the heat filter applied to an original image. The effect of shock iteration number in progressively blurring and removing speckle from an original image as the number of iterations increases is shown in FIG. 23. In this case the heat filter is described by process blocks 1010A4 and A6 of FIG. 21. In this example, an original image of a bladder is shown in panel (a) having visible speckle spread throughout the image. Some blurring is seen with the 10 iteration image in panel (b), followed by more progressive blurring at 50 iterations in panel (c) and 100 iterations in panel (d). As the blurring increases with iteration number, the speckle progressively decreases.

Figure 24:
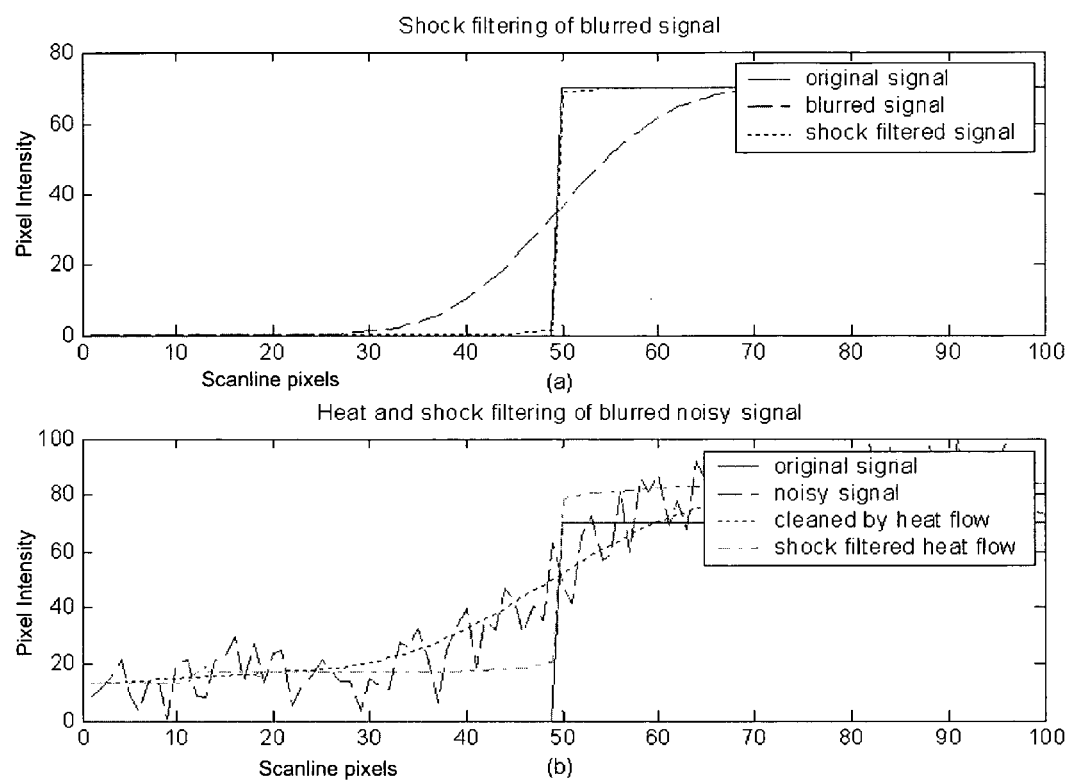
FIG. 24 shows the affect of shock filtering and a combination heat-and-shock filtering to the pixel values of the image.

FIG. 24 shows the effect of shock filtering and a combination heat-and-shock filtering to the pixel values of the image. The effect of shock iteration number, step sizes, and gradient thresholds on the blurring of a heat filter is seen in ultrasound signal plots (a) and (b) of FIG. 24. Signal plot (a) depicts a smoothed or blurred signal gradient as a sigmoidal long dashed line that is subsequently shock filtered. As can be seen by the more abrupt or steep stepped signal plots after shock filtering, the magnitude of the shock filtered signal (short dashed line) approaches that of the original signal (solid line) without the choppy or noisy pattern associated with speckle. For the most part there is virtually a complete overlap of the shock filtered signal with the original signal through the pixel plot range.

Similarly, ultrasound signal plot (b) depicts the effects of applying a shock filter to a noisy (speckle rich) signal line (sinuous long dash line) that has been smooth or blurred by the heat filter (short dashed line with sigmoidal appearance). In operation the shock filter results in a generally deblurring or sharpening of the edges of the image that were previously blurred. Adjacent with, but not entirely overlapping with the original signal (solid line) throughout the pixel plot range, the shock filtered plot substantially overlaps the vertical portion of the original signal, but is stay elevated in the low and high pixel ranges. Like in (a), a more abrupt or steep stepped signal plot after shock filtering is obtained without significant removal of speckle. Dependent on the gradient threshold, step size, and iteration number imposed by block 1010A10 upon shock block 1010A8, different overlapping levels of the shock filtered line to that of the original is obtained.

FIG. 25 is a 7-panel image set generated by the image enhancement and segmentation algorithms of FIG. 21. Panel (a) is an image of the original uterine image. Panel (b) is the image that is produced from the image enhancement processes primarily described in blocks 1010A4-6 (heat filters)

and blocks 1010A8-10 (shock filters) of FIG. 21. Panel (c) shows the effects of the processing obtained from blocks 1010B2-4 (Estimate Shadow and Fetal Body Regions/Body Threshold). Panel (d) is the image when processed by the Intensity-Based Segmentation Block Group 1010B2-8. Panel (e) results from application of the Edge-Based Segmentation Block Group 1010C2-6. Thereafter, the two Intensity-based and Edge-based block groups are combined (combining block 1010D2) to result in the image shown in panel (f). Panel (g) illustrates the effects of the blocks In-plane and Out-of-plane opening and closing processing blocks 1010D4-8.

FIG. 26 is a pixel difference kernel for obtaining X and Y derivatives to determine pixel gradient magnitudes for edge-based segmentation. As illustrated, a simplest case convolution is obtained for a first derivative computation where $K_x$ and $K_y$ are convolution constants.

FIG. 27 is a 3-panel image set showing the progressive demarcation or edge detection of organ wall interfaces arising from edge-based segmentation algorithms. Panel (a) is the enhanced input image. Panel (b) is the image result when the enhanced input image is subjected to the spatial gradients block 1010C2. Panel (c) is the image result when the enhanced and spatial gradients 1010C2 processed image is further processed by the threshold of gradients process block 1010C4.

Demonstrations of the algorithmic manipulation of pixels of the present invention are provided in Appendix 1: Examples of Algorithmic Steps. Source code of the algorithms of the present invention is provided in Appendix 2: Matlab Source Code.

While the preferred embodiment of the invention has been illustrated and described, as noted above, many changes can be made without departing from the spirit and scope of the invention. For example, other uses of the invention include determining the areas and volumes of the prostate, heart, bladder, and other organs and body regions of clinical interest. Accordingly, the scope of the invention is not limited by the disclosure of the preferred embodiment.

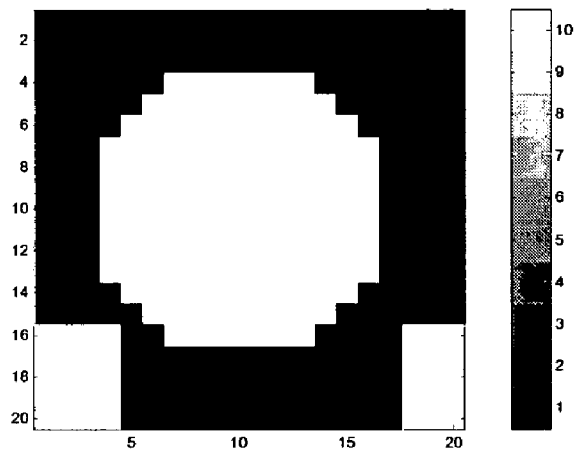
Figure A: Example input image with 20 rows and 20 columns.

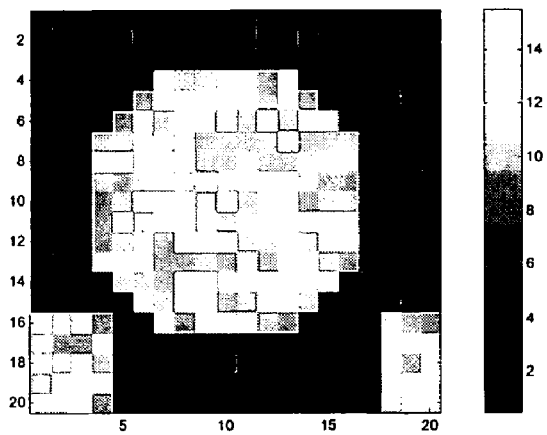
Figure B: Noisy image generated by adding random values to every pixel of the example image shown in Figure A.

The Laplacian of the example image is computed and this is shown in Figure C(1). Notice the negative values on the inside of the bright areas and positive values on the outside of the bright areas at the edges of the regions. The Laplacian is zero an pixels far from edges.

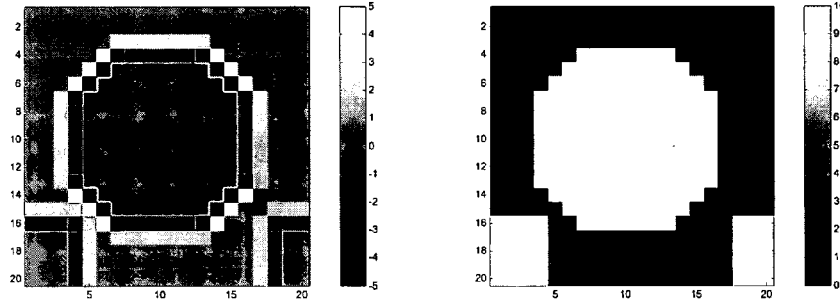

(1)                                        (2)

Figure C (1): The Laplacian of the example image shown in Figure A. (2) The Laplacian added back to the input image.

When this Laplacian is added back to the input image, after multiplying with a step size parameter, it results in blurring of the edges since the bright areas are reduced in brightness and the dark areas are increased in brightness – this output is shown in Figure C(2). This is the output of a single iteration of the heat filter. The heat filter outputs after 4 iterations and after 20 iterations are shown in (1)                              (2)
Figure D. Notice the progressive blurring of the image as you apply more iterations.

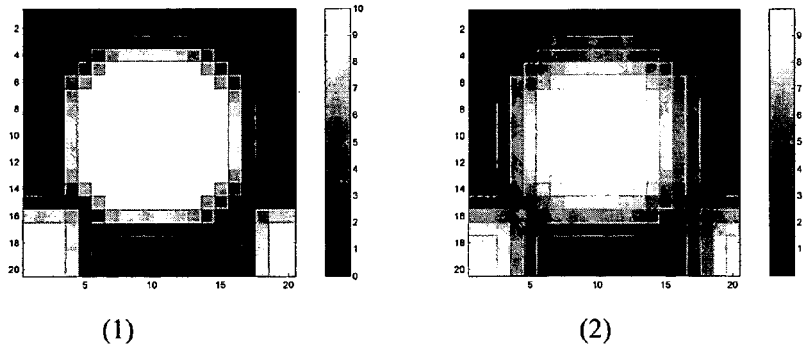

(1)                                        (2)

Figure D: Heat filter outputs after 4 iterations (1) and after 20 iterations (2) on the image shown in Figure A.

Applying 20 iterations of the heat filter to the noisy image from Figure B results in a reduction of noise and a blurring of the image. This output is shown in Figure E.

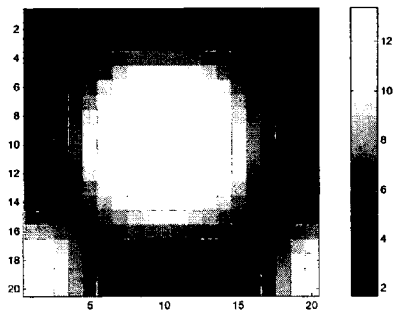

Figure E: The result of applying heat filter to a noisy image.

Note that in this image, the noise has been significantly removed, although the image is very blurred. This image looks very similar to the heat filtered version of the noiseless image shown in Figure D(2).

SHOCK FILTER – 518

The application of the shock filtered to the blurred image is shown in Figure E to sharpen this image. For purposes of the shock filter, the Laplacian of an image (Equation E4) is computed as:

$$\ell(u) = u_{xx}u_x^2 + 2u_{xy}u_x u_y + u_{yy}u_y^2.$$

This is computed for the blurred image and is shown below in shown in Figure F(1). Again, notice the negative values on the inside of the bright areas and positive values on the outside of the bright areas at the edges of the regions.

The gradient magnitude of the blurred image (Equation E3) is:

$$\|\nabla u\| = \sqrt{u_x^2 + u_y^2}$$

This is computed for the blurred image and is shown in Figure F(2) below. Note that the gradient magnitude is highest at the edges and zero in smooth regions.

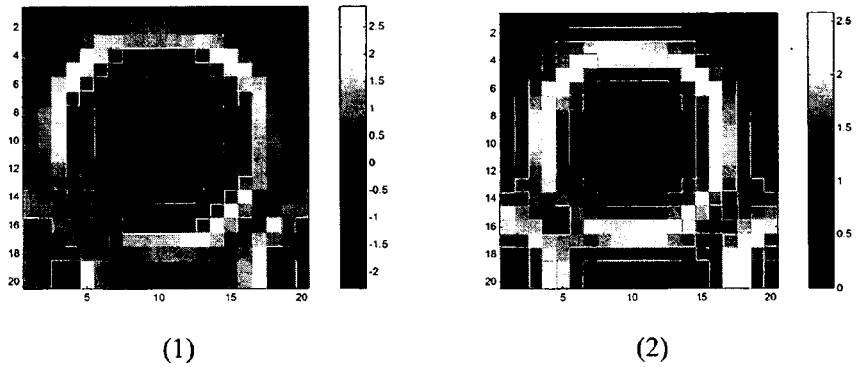

Figure F (1) The Laplacian of the blurred image. (2) The gradient magnitude of the blurred image.

Using a threshold value, t, on pixel gradient to be 0.7 we can compute the F function, which is positive where the Laplacian is greater than zero and the gradient magnitude is greater than a threshold, negative where the Laplacian is less than zero and the gradient magnitude is greater than the threshold and zero elsewhere:

$$F(\ell(u)) = 1, \text{ if } \ell(u) > 0 \text{ and } \|\nabla u\| > t$$
$$= -1, \text{ if } \ell(u) < 0 \text{ and } \|\nabla u\| > t$$
$$= 0, \text{ otherwise}$$

This F image is shown in Figure G(1) below. Note that as with the Laplacian image, everything outside the original white regions at the edge is 1, everything inside the original white regions at the edge is −1. The boundaries of the original region can be seen as the transition between the negative and the positive F values (the zero crossings).

Now, the right hand side of the shock filter equation E2, is the negative of the product of the F function image Figure G(1) and the gradient magnitude image shown in Figure F(2):

$$- F(\ell(u))\|\nabla u\|$$

This right hand side of the shock filter equation is shown in Figure G(2). If we add this image to the original blurred image we can see that it has the opposite effect of the heat filter. The dark pixels in Figure G(2) are subtracted from the blurred image and the bright pixels are added to the blurred image basically, thereby making the blurred image more crisp.

The addition of this image to the input blurred image is basically what constitutes a single iteration of the shock filter – this addition is shown in Figure H(1). After 20 iterations, a crisper output as shown in Figure H(2) is obtained. While this image is not identical to the input noiseless image of Figure A, it is quite similar to it and much more noise free as compared to the noisy version shown in Figure B.

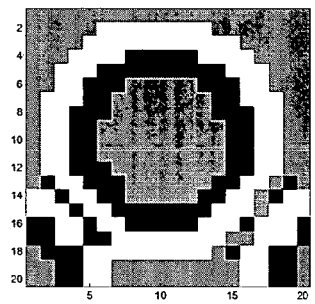 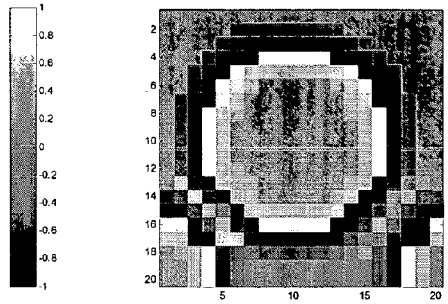

(1) (2)

Figure G: (1) The F function computed from the Laplacian and the gradient. (2) The negative of the product of the F function and the gradient.

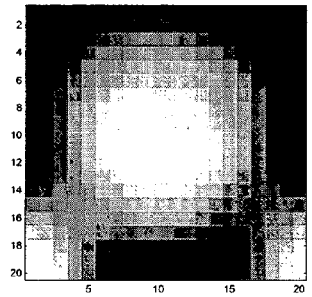 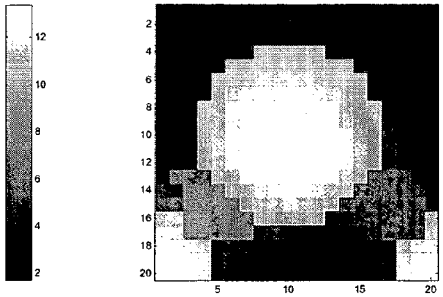

Figure H(1) The output of 1 iteration of the shock filter on the blurred image from Figure E. (2) The output of 20 iterations of the shock filter on the same blurred image.

INTENSITY CLUSTERING – 422

In intensity clustering, the enhanced image is subject to the k-means clustering algorithm. In this example, the enhanced image, shown in Figure H(2), is clustered into 4 clusters.

The minimum and maximum intensity values are 1.69 and 13.40. We divide that range into 4 partitions and get the following initial cluster boundaries.

1.19   4.12   7.04   9.98   13.90

With this partition, all pixels with values between 1.19 and 4.12 are assigned into cluster 1, all between 4.12 and 7.04 are assigned into cluster 2, etc. This initial assignment of every pixel to the 4 clusters is shown in Figure I(1) . Based on this assignment new cluster centers are found and new partition boundaries found accordingly – after this first iteration, the cluster boundaries move slightly and they are now at:

1.19   4.08   6.30   9.57   13.90.

In the next iteration, the pixel assignment based on these partition boundaries is shown in Figure I(2). Finally, after 6 iterations, the partition boundaries change very little between iterations and are set to:

1.19   3.65   5.646   9.25   13.90

The final assignment of pixels to the 4 clusters is shown in Figure I(3). For this example, the output of the clustering step is the set of pixels assigned to the brightest cluster. This output is shown in Figure I(4).

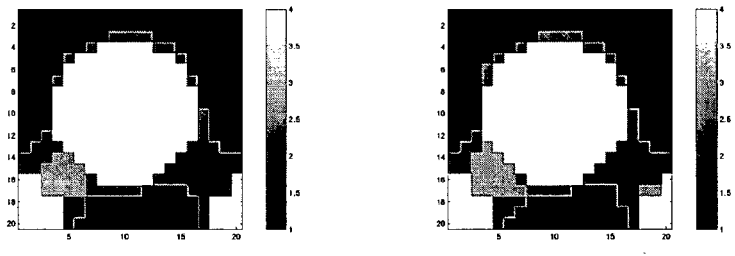

(1)                                    (2)

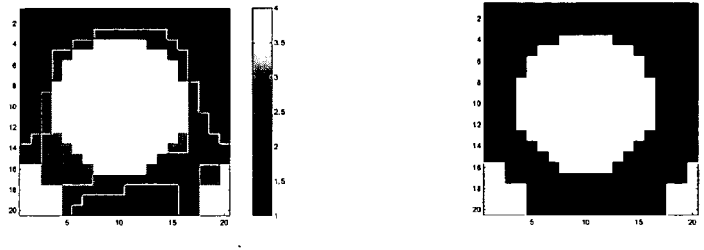

(3)                  (4)

Figure I: The output of clustering at different iterations of the k-means clustering process. (1) Initial assignment (2) After the first iteration (3) Final assignment after 6 iterations. (4) The one brightest cluster representing the region of interest.

SPATIAL GRADIENT – 526

To compute the gradient magnitude of the enhanced image shown in Figure H(2), the x-derivative $u_x$ and the y-derivative $u_y$ of the image is calculated and then the sum of squares of the two images is calculated to get the gradient magnitude -- $\|\nabla u\| = \sqrt{u_x^2 + u_y^2}$. The x- and y-derivatives and the gradient magnitudes of the enhanced image are shown in Figure J.

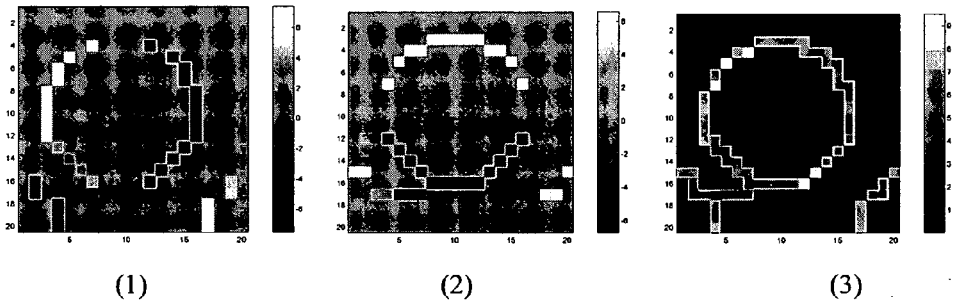

(1)           (2)           (3)

Figure J: Spatial gradients of the image shown in Figure H(2): (1) x-derivative of image (2) y-derivative of image (3) gradient magnitude of image.

HYSTERESIS THRESHOLD – 530

In the hysteresis threshold, two threshold values based on the percentage of non-edge pixels desired and the ratio of the two thresholds is determined. In this example, the percentage non-edge pixels desired is set to 90% and the lower to upper threshold ratio is set to 0.5.

The upper threshold is first computed by looking at the histogram and the cumulative histogram of the gradient magnitude image shown in Figure J(3). The histogram of the gradient magnitude image is shown in Figure K(1). The histogram shows the count of pixels of different gradient values on the image. The cumulative histogram calculated by cumulatively adding up the bins of the histogram is shown in Figure K(2). The cumulative histogram shows the count of all pixels less than a given value in the gradient magnitude image. The horizontal line shown in Figure K(2) corresponds to a y-value of 90% of the image pixels (0.90 * 20 * 20 = 360). The intersection of this line with the cumulative histogram gives the threshold at which 90% of the image pixels will be marked as non-edge and 10% will be marked as edge. From the graph, we can see that a threshold of 7 satisfies that condition. The lower threshold is set to 0.5 times the upper threshold of 7, which gives 3.5.

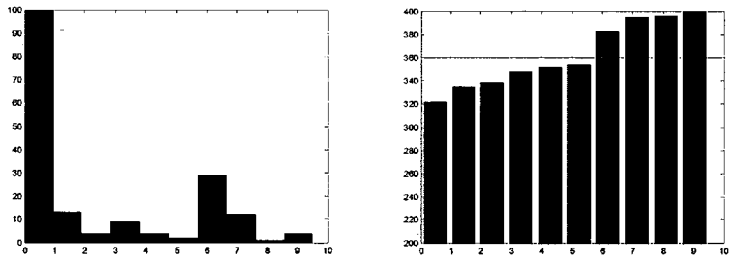

Figure K: Histogram and cumulative histogram of the gradient magnitude image.

For the hysteresis threshold, the threshold of the image at the two threshold values of 3.5 and at 7 is set and then all edge segments from the lower threshold image is selected that have at least one higher threshold pixel. The two thresholded images and the output of the Hysteresis threshold step are shown in Figure L. In this example, note that one edge segment – (row 15, column 2) has no pixel greater than the higher threshold and is therefore removed from the output. All other edge segments from Figure L(1) are retained in the output.

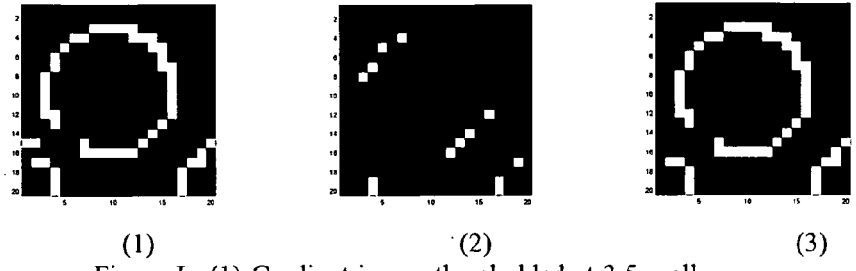

(1)            (2)            (3)

Figure L: (1) Gradient image thresholded at 3.5 – all pixels greater than 3.5 are shown as white (2) gradient image thresholded at 7, (3) Output of hysteresis threshold.

MATCHING EDGES FILTER – 538

The matching edges filter selects pairs of matching edges from among all the edges found by the hysteresis threshold step (Figure L(3)). The y-derivative image, shown in Figure J(2) is used in this step to help find the vertical matching edges. The matching edges found by this step of the algorithm are shown in Figure M(1) and the filled region between the leading the trailing edges are shown in Figure M(2). Note that this step gets rid of edges of regions on the periphery of the image since it cannot find matching trailing edges for those regions. Also, note that in the output filled image we have some unfilled lines where the gradient was primarily horizontal or where the matching edges did not exist.

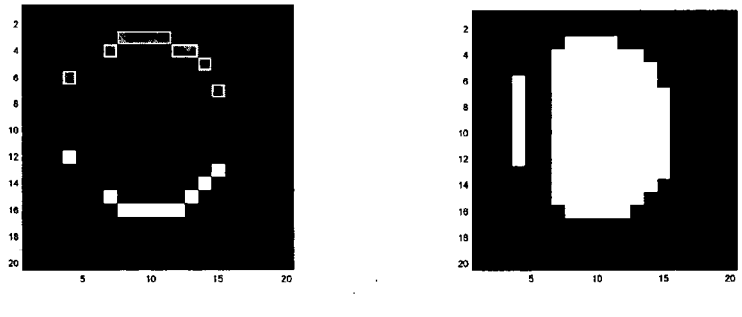

(1)            (2)

Figure M: (1) Matching edges found by the algorithm – leading edges shown in gray and lagging edges shown in white. (2) The region between the leading the lagging edges filled by white pixels.

AND IMAGES – 442

The two images shown in Figure I(4) and Figure M(2) represent the segmentation of the input noisy image shown in Figure B. Neither of them represents a perfect output. The region-based algorithm finds extraneous regions while the edge-based algorithm misses part of the desired region. The two images are combined using a Boolean AND operator and the output is shown in Figure N.

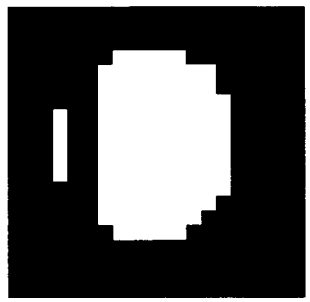

Figure N: Combining the region-based and edge-based segmentation.

CLOSE AND OPEN – 546 & 550

Using a structuring element shaped like a line of width 5 pixels, we close the output of AND images and this gives us a single region representing the structure of interest as shown in Figure O.

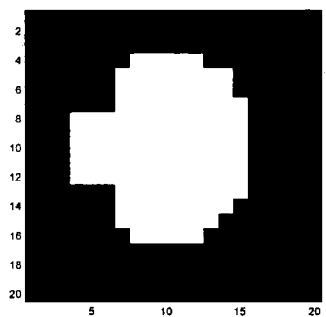

Figure O: Result of closing the image from Figure N.

Opening this image does not change the result — however, Figure P shows an example of opening on another image. The input image, Figure P(1), contains two regions, one large region and one small region. The large region is 10 pixels in width and height while the small region is 4 pixels in width and height. Using a structuring element shaped like a line of length 5 pixels and applying morphological opening to the input image results in an image shown in Figure P(2) where the smaller region whose width was smaller than the structuring element was removed from the image.

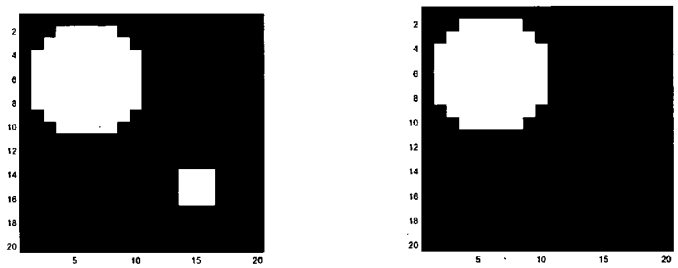

(1) (2)

Figure P: (1) Input image containing two foreground regions. (2) Output image after opening where the smaller region was removed because it was smaller than the structuring element.

FILTER DEEP REGIONS – 554

This filtering step is used to remove regions from a segmented image that start at a location deeper than a user specified depth threshold. This filtering is illustrated in Figure Q, where the input image contains two regions -- one region starts at row 2 and the other region starts at row 14. For each region on the input image, the starting row is determined after doing a connected component labeling — then using a depth threshold of 12, the regions where the starting row depth is greater than the depth threshold are removed from the input image.

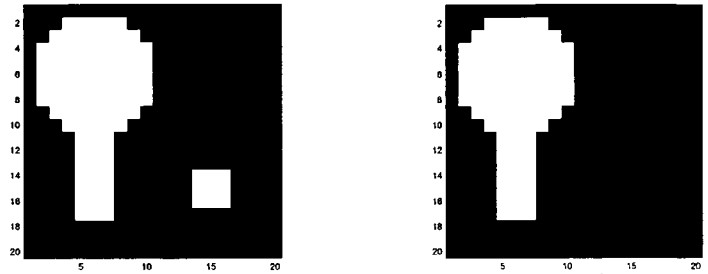

Figure Q: (1) Input image containing two foreground regions. (2) Output image after removing the region whose starting row is greater than the depth threshold of 12.

HEAD DIAMETER RANGE – 730

For a gestational age of 20 weeks, the bi-parietal diameter (BPD) is typically 46 mm. The calculated Head Diameter search range, which ranges from -30% to +30% of the typical BPD value, is found to be:

32.2   36.8   41.4   46.0   50.6   55.2   59.8

For a gestational age of 36 weeks, the bi-parietal diameter (BPD) is typically 88 mm. The calculated Head Diameter search range, which ranges from -30% to +30% of the typical BPD value, is found to be:

61.6   70.4   79.2   88.0   96.8   105.6   114.4

POLAR HOUGH TRANSFORM – 738

To illustrate the polar Hough transform, an exemplary image is generated of a circle in the Cartesian coordinates using the circle equations, E5. This circle image was then dilated to result in a disk like shape and then a few rows of data were set to zero. This input image is shown in Figure R(1). The goal of the circular Hough transform is to find the circle that best fits the white pixels in this input image.

Next, this Cartesian input image was converted to polar domain by inverse scan conversion and the resulting image is shown in Figure R(2). To this polar coordinate image, the polar Hough transform for a circle was applied, where for each white pixel on the image a polar circle of a known radius was drawn. The output of the Hough transform is the sum of all such circles and this is shown in Figure R(3). The center of the best-fit circle has the most points passing through it. So, to determine the best-fit circle, we simply found the pixel on the Hough output with the maximum value. The point with the maximum value represents the center of the best-fit circle.

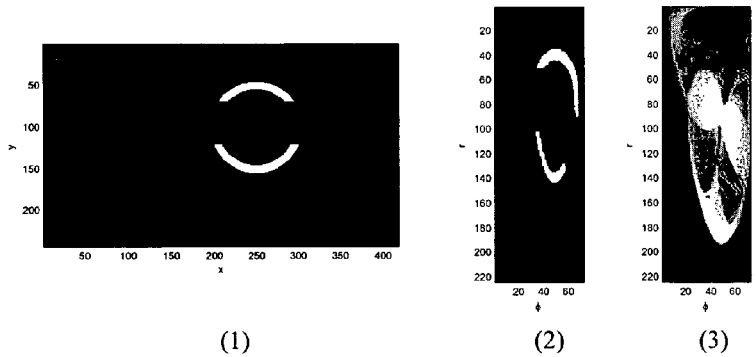

(1) (2) (3)

Figure R: (1) The input Cartesian coordinate partial circle (2) The partial circle converted to polar coordinates, (3) The Hough transform output showing the sum of polar circles drawn around each white pixel of the input image.

The best-fit circle determined by this Hough transform procedure is overlaid on the polar coordinate image and the Cartesian coordinate image and the two drawings are shown in Figure S.

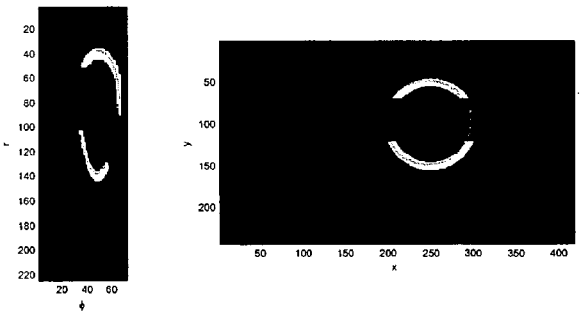

Figure S: The best fit circle found using a Polar coordinate Hough transform (1) overlaid on the polar coordinate input data and (2) overlaid on the Cartesian coordinate input data.

FILL CIRCLE REGION – 746

A circle region in Cartesian space has a somewhat different shape in the Polar coordinate space. To illustrate this polar coordinate circle, we use both Cartesian coordinate and polar coordinate circles. First, a Cartesian coordinate circle of radius 50 pixels and a center (120,250) is drawn using the circle equation, E5, $(x-x_0)^2 + (y-y_0)^2 = R^2$ -- this circle is shown in Figure T(1).

Now, the Cartesian center coordinates $(x_0, y_0)$ are converted from Cartesian to polar center $(r_0, \phi_0)$ using the scan conversion equations:

$$r_0^2 = (x_0^2 + y_0^2),$$
$$\phi_0 = \tan^{-1}(y_0 / x_0)$$

Next, the polar coordinate circle drawing and filling equation, E6, $(r\sin\phi - r_0\sin\phi_0)^2 + (r\cos\phi - r_0\cos\phi_0)^2 = R^2$, is applied to draw and fill the same circle of radius R=50, in polar coordinates. This circle in the polar coordinates is shown in Figure T(2).

Finally, to verify that this polar coordinate circle in indeed a representation of the Cartesian coordinate circle, the polar circle image is scan-converted to generate the representative Cartesian coordinate circle image. This scan-converted circle is shown in Figure T(3). Comparing Figure T(1) and Figure T(3), it can be seen that while the two circles are not identical, they are fairly similar. The differences are due to the fact that the polar coordinate data cannot represent Cartesian data completely.

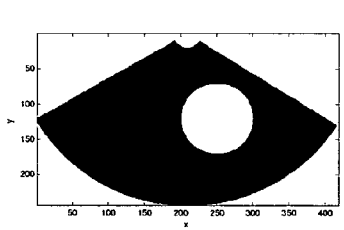
(1)

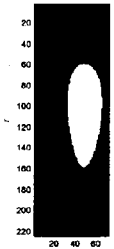
(2)

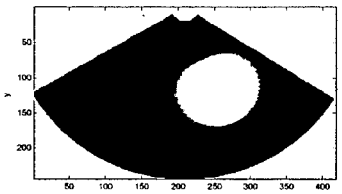
(3)

Figure T Polar coordinate circle filling. (1) A filled circle in a Cartesian coordinate image (2) The equivalent filled circle in polar coordinate image, (3) The scan converted polar coordinate filled circle image.

APPENDIX 2: MATLAB SOURCE CODE

HEAT FILTER – 514

```
function out = heat_flow2D( I, num_iter, time_step )
% heat_flow2D: 2D heat flow filter same as Gaussian filtering.
%
% out = heat_flow2D( I, num_iter, time_step )
%    * I is the input image
%    * num_iter is the number of iterations for which to run the filter
%    * time_step is the size of the time step between iterations.
%    * out is the output smoothed image
%
%    The heat flow equation is I(t+1) = I(t) + time_step * Laplacian(I)
%    Gaussian standard deviation (sigma) = sqrt( 2 * num_iter * time_step )
%    or, if time_step = 0.25, num_iter = 2 * sigma^2.

[m n] = size(I);
update = zeros(m, n);
rows = 1:m;
cols = 1:n;

prev_rows = rows - 1;
prev_rows(1) = 1;
next_rows = rows + 1;
next_rows(m) = m;

prev_cols = cols - 1;
prev_cols(1) = 1;
next_cols = cols + 1;
next_cols(n) = n;

for iter = 1:num_iter
    update = (I(rows, next_cols) + I(next_rows,cols) - 4*I(rows,cols) + I(prev_rows, cols) + I(rows, prev_cols))/4;
    I = I + time_step * update;
end out = I;
```

SHOCK FILTER – 518

```
function out = shock_filter_grad2D( I, num_iter, time_step, grad_thresh )
%-- 2D shock filter
%-- the equation is I(t+1) = I(t) - sign(Ixx) . | grad( I ) |
```

```
%-- sign(Ixx) is the laplace and grad(I) is the updwind derivative
% here instead of using Ixx for edges, we use magnitude of grad(I) as edge.

[m n] = size(I);
update = zeros(m, n);
diff = zeros(m,n);
gradmat = zeros(m, n);
gradmag = zeros(m, n);
laplace  = zeros(m, n);
diffpos = zeros(m, n);
diffneg = zeros(m, n);
dplus = zeros( m, n);
dminus = zeros( m, n);
cond1 = zeros( m, n);
cond2 = zeros( m, n);

rows = 1:m;
cols = 1:n;

prev_rows = rows - 1;
prev_rows(1) = 1;
next_rows = rows + 1;
next_rows(m) = m;

prev_cols = cols - 1;
prev_cols(1) = 1;
next_cols = cols + 1;
next_cols(n) = n;

for iter = 1:num_iter
    %laplace = (I(rows, next_cols) + I(next_rows,cols) - 4*I(rows,cols) + I(prev_rows, cols) + I(rows, prev_cols))/4;
    laplace = laplace2( I );

% instead of centered diff - lets use upwind
    %gradmat = 0.5*abs(I(next_rows, cols) - I(prev_rows, cols));

%row derivative forward
    diff = I(next_rows,cols) - I(rows,cols);
    cond1 = diff >= 0;
    cond2 = diff < 0;
    diffpos( cond1 ) = diff( cond1 );
    diffpos( cond2 ) = 0;
    diffneg( cond2 ) = diff( cond2 );
    diffneg( cond1 ) = 0;
```

```
dplus  = diffneg .* diffneg;
dminus = diffpos .* diffpos;

%row derivative backward
diff = I(rows,cols) - I(prev_rows,cols);
cond1 = diff >= 0;
cond2 = diff < 0;
diffpos( cond1 ) = diff( cond1 );
diffpos( cond2 ) = 0;
diffneg( cond2 ) = diff( cond2 );
diffneg( cond1 ) = 0;

dplus  = dplus + diffpos .* diffpos;
dminus = dminus + diffneg .* diffneg;

%col derivative forward
diff = I(rows,next_cols) - I(rows,cols);
cond1 = diff >= 0;
cond2 = diff < 0;
diffpos( cond1 ) = diff( cond1 );
diffpos( cond2 ) = 0;
diffneg( cond2 ) = diff( cond2 );
diffneg( cond1 ) = 0;

dplus  = dplus + diffneg .* diffneg;
dminus = dminus + diffpos .* diffpos;

%col derivative backward
diff = I(rows,cols) - I(rows,prev_cols);
cond1 = diff >= 0;
cond2 = diff < 0;
diffpos( cond1 ) = diff( cond1 );
diffpos( cond2 ) = 0;
diffneg( cond2 ) = diff( cond2 );
diffneg( cond1 ) = 0;

dplus  = dplus + diffpos .* diffpos;
dminus = dminus + diffneg .* diffneg;

dplus = sqrt( dplus );
dminus = sqrt( dminus );

gradmat( laplace >= 0 ) = dplus( laplace >= 0 );
gradmat( laplace < 0 )  = dminus ( laplace < 0 );
```

```
  gradmat(gradmat < grad_thresh) = 0;

laplace( laplace > 0 ) = 1;
  laplace( laplace < 0 ) = -1;

update = -gradmat .* laplace;
  I = I + time_step .* update;
end out = I;
```

INTENSITY CLUSTERING – 422

```
function min_img = cluster_image( in_img, num_clusters, sample_factor, num_iterations )
% cluster_image: Cluster an intensity image using the k-means algorithm.
%
%  out_img = cluster_image( in_img, num_clusters, sample_factor, num_iterations )
%   * in_img is the input intensity image to be clustered
%   * num_clusters is the number of output clusters desired
%   * sample_factor is a factor by which to downsample the input data. If 1, then no
sampling, if 2, then reduces
%     input data by half.
%   * num_iterations is the maximum number of iterations that the algorithm should be run
if it does not converge.
%     usually it converges in about 2-6 iterations - so you can set this to be about 20.
%   * min_img is the output image consisting of pixels lying on the cluster with the
minimum mean.
%
% A simple k-means algorithm is used for this clustering.

convergence_threshold = 0.05;

in_data = downsample( in_img(:), sample_factor );

minval = min( in_data );
maxval = max( in_data );

incval = ( maxval - minval )/num_clusters;

%cluster boundaries
boundaries = zeros(1, num_clusters + 1 );
boundaries(1) = (minval-0.5);
boundaries(num_clusters+1) = (maxval+0.5);
for i = 2:num_clusters
   boundaries(i) = boundaries(i-1) + incval;
```

```
end a = 1; b = [0.5 0.5];
centers = zeros( 1, num_clusters );
centers = filter( b, a, boundaries );
centers = centers( 2:end );
old_centers = centers;

for iter = 1:num_iterations

%lets quantize the data according to the boundaries
    for j = 1:num_clusters
        cdata = in_data( in_data <= boundaries(j+1) & in_data > boundaries(j) );
        centers(j) = mean(cdata);
    end %lets recompute the boundaries
    newb = filter( b, a, centers );
    newb( 1 ) = (minval-0.5);
    boundaries = [newb, (maxval+0.5)];

%centers
    diff = norm( ( centers - old_centers ) ./ old_centers );
    if ( diff <= convergence_threshold )
        %disp(sprintf('converged in %d iterations', iter ));
        break;
    end old_centers = centers;
end min_thresh1 = boundaries( 1 );
min_thresh2 = boundaries( 2 );
min_img = ( in_img <= min_thresh2 ) & ( in_img > min_thresh1 );

min_img = reshape( min_img, size( in_img ) );
```

SPATIAL GRADIENTS – 526

```
function [xgrad,ygrad,grad_mag] = spatial_gradients( in_img )
% spatial_gradients: Compute spatial gradients of the 2D input image
%
% [xgrad,ygrad,grad_mag] = spatial_gradients( in_img )
%    * in_img is the input input image
%    * xgrad is the x-direction gradient
```

```
%    * ygrad is the y-direciton gradient
%    * grad_mag is the gradient magnitude
% kernx = [-1  1];
kerny = [-1; 1];

xgrad = imfilter( in_img, kernx );
ygrad = imfilter( in_img, kerny );
grad_mag = sqrt( xgrad .^ 2 + ygrad .^ 2 );
```

HYSTERESIS THRESHOLD – 530

```
function out = hysteresis_threshold( grad_mag, PercentNonEdge, FractionLow )
% hysteresis_threshold: Perform hysteresis thresholding by automatically computing two
thresholds
%
% out = hysteresis_threshold( grad_mag, PercentNonEdge, FractionLow )
%    * grad_mag is gradient magnitude image to be thresholded
%    * PercentNonEdge is the percentage of non-edge pixels desired (0.97 works good)
%    * FractionLow is the ratio between the lower and the upper threshold (0.5 works good)

%lets try to figure out the thresholds
maxgrad = max( grad_mag(:) );
[c x] = hist( grad_mag(:), ceil( maxgrad ) );
[m n] = size( grad_mag );
high_thresh = min( find( cumsum( c ) > PercentNonEdge * m * n ) );

%lets threshold the gradients
out = hysteresis_threshold_core( grad_mag, FractionLow * high_thresh, high_thresh );

function out = hysteresis_threshold_core( img, t1, t2 )
%do a hystersis theresholding of an image at a lower threshold of t1 and an upper threshold
of t2
%basically, we first do a thresholding at the lower value
%then we do a connected component
%then we pick those components which have at least one value above t2
%here, we are going to do it a little differently,
%  1. we will first threshold at t2
%  2. we will select one point each from t2
%  3. then we will threshold at t1
%  4. for each point from t2, we will use bwlabel/bwselect to find the component on the t1
image
%
```

```
%lets first threshold at higher threshold t2
t2_thresh = img > t2;

[r c] = find( t2_thresh );

%lets now threshold at lower thresh t1
t1_thresh = img > t1;

out = bwselect( t1_thresh, c, r, 8 );
```

MATCHING EDGES FILTER - 538

```
function [out_filled, out_edg2] = find_matching_vertical_edges( in_edg, ygrad )
% find_matching_vertical_edges: Find mataching edges in the vertical direction
%
% out_filled = find_matching_vertical_edges( in_edg, ygrad )
% * in_edg is the input edge image
% * ygrad is the y-direction gradient
% * out_filled is the output filled region between edges
% out_ygrad = ygrad;
out_ygrad( in_edg == 0 ) = 0;

dist_thresh = 5;

%for every line, select the closest edge pairs
[npts nline] = size( in_edg );
out_edg2 = zeros( size( in_edg ) );
out_filled = out_edg2;

for line = 1:nline
   fw_pts = find( out_ygrad(:,line) < 0 );
   bw_pts = find( out_ygrad(:,line) > 0 );
   lfw = length( fw_pts );
   lbw = length( bw_pts );
   if ( lfw == 0 | lbw == 0 )
      continue;
   end
   if ( ( lfw == 1 ) & ( lbw == 1 ) )
      if ( bw_pts(1) > fw_pts(1) )
         out_edg2( fw_pts(1), line ) = 1;
         out_edg2( bw_pts(1), line ) = 2;
         out_filled( fw_pts(1):bw_pts(1), line ) = 1;
```

```
        end
        continue;
end votes_fw = zeros( size( fw_pts ) );
votes_bw = zeros( size( bw_pts ) );

%for every front wall point find the closest backwall point
for fw = 1:lfw
    curr_fw = fw_pts( fw );
    min_bw = 0;
    min_dist = 1000000;
    for bw = 1:lbw
        curr_dist = bw_pts( bw ) - curr_fw;
        if ( curr_dist > dist_thresh & curr_dist < min_dist )
            min_bw = bw;
            min_dist = curr_dist;
        end
    end
    if ( min_bw > 0 )
        votes_fw( fw ) = votes_fw( fw ) + 1;
        votes_bw( min_bw ) = votes_bw( min_bw ) + 1;
    end
end %for every bacak wall point find the closest frontwall point
for bw = 1:lbw
    curr_bw = bw_pts( bw );
    min_fw = 0;
    min_dist = 1000000;
    for fw = 1:lfw
        curr_dist = curr_bw - fw_pts( fw );
        if ( curr_dist > dist_thresh & curr_dist < min_dist )
            min_fw = fw;
            min_dist = curr_dist;
        end
    end
    if ( min_fw > 0 )
        votes_fw( min_fw ) = votes_fw( min_fw ) + 1;
        votes_bw( bw ) = votes_bw( bw ) + 1;
    end
end %at this point, the fw and bw with votes greater than 1 should be matching
good_fw_pts = fw_pts( votes_fw > 1 );
good_bw_pts = bw_pts( votes_bw > 1 );
```

```
if ( length( good_fw_pts ) ~= length( good_bw_pts ) )
    disp('match not found' );
else
    for i = 1:length( good_fw_pts )
        out_edg2( good_fw_pts(i), line ) = 1;
        out_edg2( good_bw_pts(i), line ) = 2;
        out_filled( good_fw_pts(i):good_bw_pts(i), line ) = 1;
    end
end end
```

CLOSE & OPEN – 546 & 550

```
function out = close3D_brick( in, size1, size2, size3 )

tmp = dilate3D_brick(in, size1, size2, size3 );
    out = erode3D_brick(in, size1, size2, size3 );

function out = open3D_brick( in, size1, size2, size3 )

tmp = erode3D_brick(in, size1, size2, size3 );
    out = dilate3D_brick(in, size1, size2, size3 );

function out = erode3D_brick( in, size1, size2, size3 )
    % erode3D_brick: Erode a binary image with a brick shaped structuring element.
    %
    % out_img = erode3D_brick( in, size1, size2, size3 )
    %  * in_img is the input binary image to be dilated
    %  * size1 is the size of the brick along the row dimension
    %  * size2 is the size of the brick along the column dimension
    %  * size3 is the size of the brick along the slice dimension
    %
    % A seprable order-statistic filter with the ordinal as min is used.

[nr nc np] = size( in );
    out = in;

for p = 1:np
        %lets first do the dilation along rows
        out(:,:,p) = ordfilt2( out(:,:,p), 1, ones( size1, 1 ) );

%lets first do the dilation along columns
        out(:,:,p) = ordfilt2( out(:,:,p), 1, ones( 1, size2 ) );
    end
```

```
        %now lets do it along the third dimension
        %first permute dimension
        tmp = permute( out, [3, 2, 1] );
        for r = 1:nr
            tmp(:,:,r) = ordfilt2( tmp(:,:,r), 1, ones( size3, 1 ) );
        end out = permute( tmp, [3, 2, 1] );

function out = dilate3D_brick( in, size1, size2, size3 )
    % dilate3D_brick: Dilate a binary image with a brick shaped structuring element
    %
    % out_img = dilate3D_brick( in, size1, size2, size3 )
    %   * in_img is the input binary image to be dilated
    %   * size1 is the size of the brick along the row dimension
    %   * size2 is the size of the brick along the column dimension
    %   * size3 is the size of the brick along the slice dimension
    %
    % A seprable order-statistic filter with the ordinal as max is used.

[nr nc np] = size( in );
    out = in;

for p = 1:np
        %lets first do the dilation along rows
        out(:,:,p) = ordfilt2( out(:,:,p), size1, ones( size1, 1 ) );

%lets first do the dilation along columns
        out(:,:,p) = ordfilt2( out(:,:,p), size2, ones( 1, size2 ) );
    end %now lets do it along the third dimension
    %first permute dimension
    tmp = permute( out, [3, 2, 1] );
    for r = 1:nr
        tmp(:,:,r) = ordfilt2( tmp(:,:,r), size3, ones( size3, 1 ) );
    end out = permute( tmp, [3, 2, 1] );
```

FILTER DEEP REGIONS – 554

```
function out = filter_deep_regions( in, depthThreshold )
% filter_deep_regions: Filter out regions that start beyond the depth threshold
```

```
%
% out = filter_deep_regions( in, depthThreshold )
%   * in is the input binary image
%   * depthThreshold is the threshold beyond which regions are not acceptable
%   * out is the output filtered binary image

[ccmp n] = bwlabel( in );
props = regionprops( ccmp, 'BoundingBox' );
out = zeros( size(in) );
j = 0;
for i = 1:n
    if ( props(i).BoundingBox(2) < depthThreshold )
        out = out + ( ccmp == i );
        j = j+1;
    end
end
```

HEAD DIAMETER RANGE – 730

```
function rad_range = radrange_lookup( age, imgParams )
%lookup the radius range in pixels given the gestational age and the
%resolution mean_bpd = bpd_lookup( age );
mean_rad = 0.5 * mean_bpd / imgParams.AxialResolution;
rad_range = [mean_rad - ( 0.3 * mean_rad )
        mean_rad - ( 0.2 * mean_rad ),
        mean_rad - ( 0.1 * mean_rad ),
        mean_rad,
        mean_rad + ( 0.1 * mean_rad ),
        mean_rad + ( 0.2 * mean_rad )
        mean_rad + ( 0.3 * mean_rad )];

function bpd_out = bpd_lookup( age )
    %lookup the bpd in mm given the gestational age %BPD Table   wks; BPD in mm
    bpd_table = [14, 26;
            15, 30;
            16, 33.5;
            17, 36.5;
            18, 40;
            19, 43;
            20, 46;
            21, 49.5;
            22, 52.5;
```

```
        23, 55.5;
        24, 58;
        25, 61;
        26, 64;
        27, 66.5;
        28, 69;
        29, 72;
        30, 74;
        31, 76.5;
        32, 79;
        33, 81;
        34, 83.5;
        35, 86;
        36, 88;
        37, 90;
        38, 92;
        39, 94;
        40, 96;
    ];

bpd_out = 0;
if ( age < 14 )
   return;
end bpd_out = 100;
if ( age > 40 )
   return;
end index = round( age - 14 + 1 );
bpd_out = bpd_table(index,2);
```

HEAD EDGE DETECTION – 734

```
function edg2 = find_head_regions( in_edg, ygrad, wall_edg, region_img, radrange )
%use ygrads to find head regions IntenThresh = 15;
DistThresh = 12;

ygrad( in_edg == 0 ) = 0;

[npts nline] = size( ygrad );
edg2 = wall_edg;
```

```
%lets go over each line and find potential head locations
%potential head locations will have
%  a. good front wall and back wall pairs identified by the wall_edg input
%  b. a matching positive gradient before the front wall - within a short distance
%  c. a matching negative gradient after the back wall - within a short distance
for line = 1:nline neg_grad_pts = find( ygrad(:,line) < 0 );
  pos_grad_pts = find( ygrad(:,line) > 0 );
  ln = length( neg_grad_pts );
  lp = length( pos_grad_pts );

fw = find( wall_edg(:,line) == 1 );
  bw = find( wall_edg(:,line) == 2 );
  lfw = length(fw);
  lbw = length(bw);

if ( lfw > 0 & lbw > 0 & lfw == lbw )
    for i = 1:lfw
      dist = bw(i) - fw(i);
      %if distance is beyond the rad range, set to zero
      if ( dist < 2*radrange(1) | dist > 2*radrange(end) )
        edg2(fw(i),line) = 0;
        edg2(bw(i),line) = 0;
        continue;
      end %if mean intensity is not at least 80% dark
      if ( mean( region_img(fw(i):bw(i), line ) ) < 0.8 )
        edg2(fw(i),line) = 0;
        edg2(bw(i),line) = 0;
        continue;
      end %if within DistThresh of front wall is not a postive gradient point - else expand
      diffs = fw(i) - pos_grad_pts;
      if ( sum( diffs > 0 & diffs < DistThresh ) == 0 )
        edg2(fw(i),line) = 0;
      else
        if ( fw(i) > 3 & fw(i) < npts - 3 )
          edg2( (fw(i)-3):(fw(i)+3), line ) = 1;
        end
      end %if within DistThresh of back wall is not a negative gradient point
```

```
        diffs = neg_grad_pts - bw(i);
        if ( sum( diffs > 0 & diffs < DistThresh ) == 0 )
            edg2(bw(i),line) = 0;
        else
            if ( bw(i) > 3 & bw(i) < npts - 3 )
                edg2( (bw(i)-3):(bw(i)+3), line) = 2;
            end
        end
    end
    else
        edg2(:,line) = 0;
    end
end
```

POLAR HOUGH TRANSFORM – 738

```
function out = hough_circle_polar( edg_img, radii, xducerOffset, phiAngles )
%compute a hough transform for circle finding on a pre-scan converted image
%the function goes throgh every edge pixel on the image and adds an accumulator
corresponding to every radii nradii = length( radii );
[nrow ncol] = size( edg_img );

out = zeros( nrow, ncol, nradii );

angles = 0:18:360;
angles = pi*angles/180;
cosa = cos( angles );
sina = sin( angles );

prows = cosa;
pcols = cosa;

len = length( angles );
hlen = len / 2;

%go over every edge pixel
for row = 1:nrow
    for col = 1:ncol
        curr_edg = edg_img( row, col );
        if ( curr_edg > 0 )
            for rad = 1:nradii
                [prows, pcols] = draw_polar_circle( row, col, radii(rad), cosa, sina, xducerOffset, phiAngles, 0 );
                %xcoor = round(col + cosrad(rad,:));
```

```
            %ycoor = round(row + sinrad(rad,:));

for i = 1:len
                if ( prows(i) > 0 & prows(i) <= nrow & pcols(i) > 0 & pcols(i) <= ncol )
                    curr_out = out( prows(i), pcols(i), rad );
                    %out( prows(i), pcols(i), rad ) = curr_out + 1;

%if it is the front wall, then the center should be below it - on the lower half
of the circle
                    if ( curr_edg == 1 & prows(i) > row )
                        out( prows(i), pcols(i), rad ) = curr_out + 1;
                    end %if it is the back wall, then the center should be above it - on the upper half of
the circle
                    if ( curr_edg == 2 & prows(i) < row )
                        out( prows(i), pcols(i), rad ) = curr_out + 1;
                    end
                end %if
            end % for i
        end % for rad
    end % if curr_edg
  end %for col
end %for row function [prows, pcols] = draw_polar_circle( pcent_row, pcent_col, rad, costheta, sintheta,
xducerOffset, phiAngles, draw )
%draw a circle in polar coordiantes
% given a center row and column in polar coordinates, a radius in
% cartesian, and cosine and sines of theta angles
% yoff is the transducer offset
% phiAngles is the list of phiAngles if( draw )
    x1 = rad * costheta + ( pcent_row + xducerOffset ) * sin( phiAngles( pcent_col ) );
    y1 = rad * sintheta + ( pcent_row + xducerOffset ) * cos( phiAngles( pcent_col ) );
else
    x1 = -rad * costheta + ( pcent_row + xducerOffset ) * sin( phiAngles( pcent_col ) );
    y1 = -rad * sintheta + ( pcent_row + xducerOffset ) * cos( phiAngles( pcent_col ) );
end %now convert to polar
rads = sqrt( x1.^2 + y1 .^2 );
phis = atan2( x1, y1 );
```

```
prows = round(rads - xducerOffset );
pcols = interp1( phiAngles, 1:length(phiAngles), phis, 'nearest' );
```

FILL CIRCLE REGION - 746

```
function out_image = fill_polar_circle( pcent_row, pcent_col, rad, xducerOffset, phiAngles, nrow, ncol )
% fill the inside of a cirlce in polar coordiantes
% given a center row and column in polar coordinates, a radius in
% cartesian, and cosine and sines of theta angles
% yoff is the transducer offset
% phiAngles is the list of phiAngles out_image = zeros( nrow, ncol );
sinc = sin( phiAngles( pcent_col ) );
cosc = cos( phiAngles( pcent_col ) );
rad2 = rad^2;
lhs = 0;

for x = 1:nrow
    for y = 1:(ncol-1)
        lhs = x^2 + pcent_row^2 - 2 * x * pcent_row * ( sin(phiAngles(y))*sinc + cos(phiAngles(y))*cosc );
        if ( lhs <= rad2 )
            out_image( x, y ) = 1;
        end
    end
end
end
```

We claim:

1. A method to determine amniotic fluid volume, the method comprising:
   positioning an ultrasound transceiver to probe at least a portion of a uterus of a patient, the transceiver configured to obtain a plurality of scanlines;
   enhancing the images of the amniotic fluid regions in the scanline plurality with a plurality of algorithms;
   registering the plurality of scanlines;
   associating the registered scan lines into a composite array, and
   determining the amniotic fluid volume of the amniotic fluid regions within the composite array.

2. The method of claim 1, wherein transceiver positioning and re-positioning acquires the first plurality of scanlines confined within a conically shaped field emanating from the transceiver.

3. The method of claim 1, wherein the plurality of algorithms includes algorithms for image enhancement, segmentation, and polishing.

4. The method of claim 3, wherein segmentation further includes an intensity clustering step, a spatial gradients step, a hysteresis threshold step, a Region-of-Interest selection step, and a matching edges filter step.

5. The method of claim 4, wherein the intensity clustering step is performed in a first parallel operation, and the spatial gradients, hysteresis threshold, Region-of-Interest selection, and matching edges filter steps are performed in a second parallel operation, and further wherein the results from the first parallel operation are combined with the results from the second parallel operation.

6. The method of claim 3, wherein image enhancement further includes applying a heat filter and a shock filter to the digital images.

7. The method of claim 6 wherein the heat filter is applied to the digital images followed by application of the shock filter to the digital images.

8. The method of claim 1, wherein the amniotic fluid volume is adjusted for underestimation or overestimation.

9. The method of claim 8, wherein the amniotic fluid volume is adjusted for underestimation by probing with adjustable ultrasound frequencies to penetrate deep tissues and to repositioning the transceiver to establish that deep tissues are exposed with probing ultrasound of sufficient strength to provide a reflecting ultrasound echo receivable by the transceiver, such that at least a portion of the plurality of scanlines penetrate to detect deep tissue and regions of the fetal head.

10. The method of claim 8, wherein amniotic fluid volume is adjusted for overestimation by automatically determining fetal head volume contribution to amniotic fluid volume and deducting it from the amniotic fluid volume.

11. The method of claim 10, wherein the steps to adjust for overestimated amniotic fluid volumes include a 2D clustering step, a matching edges step, an all edges step, a gestational age factor step, a head diameter step, an head edge detection step, and a Hough transform step.

12. The method of claim 11, wherein the Hough transform step includes a polar Hough Transform step, a Find Maximum Hough value step, and a fill circle region step.

13. The method of claim 12, wherein the polar Hough Transform step includes a first Hough transform to look for lines of a specified shape, and a second Hough transform to look for fetal head structures.

14. The method of claim 1, wherein positioning further includes lateral and transverse.

15. A method to determine amniotic fluid volume, the method comprising:
   positioning an ultrasound transceiver to probe a first portion of a uterus of a patient, the transceiver configured to obtain a first plurality of scanlines;
   re-positioning the ultrasound transceiver to probe at least one other portion of the uterus to obtain a second plurality of scanlines;
   enhancing the images of the amniotic fluid regions in the scanlines with a plurality of algorithms;
   registering the scan lines of the first plurality and the second plurality;
   associating the registered scanlines into a composite array, and
   determining the amniotic fluid volume of the amniotic fluid regions within the composite array.

16. The method of claim 15, wherein transceiver positioning and re-positioning acquires the first and second plurality of scanlines confined within conically shaped fields emanating from the transceiver.

17. The method of claim 15, wherein the plurality of algorithms includes algorithms for image enhancement, segmentation, and polishing.

18. The method of claim 17, wherein segmentation further includes an intensity clustering step, a spatial gradients step, a hysteresis threshold step, a Region-of-Interest selection step, and a matching edges filter step.

19. A method to determine amniotic fluid volume, the method comprising:
   positioning an ultrasound transceiver to probe a first portion of a uterus of a patient, the transceiver configured to obtain a first plurality of scanlines;
   re-positioning the ultrasound transceiver to probe a second through sixth portion of the uterus to obtain a second through sixth plurality of scanlines;
   enhancing the images of the amniotic fluid regions in the scanlines with a plurality of algorithms;
   registering the scan lines of the first through sixth plurality;
   associating the registered scanlines into a composite array, and
   determining the amniotic fluid volume of the amniotic fluid regions within the composite array.

20. The method of claim 19, wherein transceiver positioning and re-positioning acquires the first through the sixth plurality of scanlines confined within conically shaped fields emanating from the transceiver.

* * * * *